(12) United States Patent
Campos-Neto et al.

(10) Patent No.: US 7,087,713 B2
(45) Date of Patent: Aug. 8, 2006

(54) COMPOUNDS AND METHODS FOR DIAGNOSIS AND IMMUNOTHERAPY OF TUBERCULOSIS

(75) Inventors: Antonio Campos-Neto, Bainbridge Island, WA (US); Yasir Skeiky, Seattle, WA (US); Pamela Ovendale, Everett, WA (US); Shyian Jen, Seattle, WA (US); Michael Lodes, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 34 days.

(21) Appl. No.: 09/793,306

(22) Filed: Feb. 26, 2001

(65) Prior Publication Data

US 2002/0098200 A1   Jul. 25, 2002

Related U.S. Application Data

(60) Provisional application No. 60/185,037, filed on Feb. 25, 2000, provisional application No. 60/223,828, filed on Aug. 8, 2000.

(51) Int. Cl.
*A61K 38/00*   (2006.01)
*A61K 39/40*   (2006.01)
*A61K 39/04*   (2006.01)
*C12Q 1/00*    (2006.01)
*C12P 1/00*    (2006.01)

(52) U.S. Cl. .................. 530/324; 530/300; 424/168.1; 424/248.1; 435/4; 435/41

(58) Field of Classification Search ............. 424/168.1, 424/248.1; 435/6, 7.1, 252.1, 253.1, 253.3, 435/320.1, 325; 536/300; 530/300
See application file for complete search history.

(56) References Cited

U.S. PATENT DOCUMENTS

| | | |
|---|---|---|
| 5,504,005 A | 4/1996 | Bloom et al. |
| 5,583,112 A | 12/1996 | Kensil et al. |
| 5,783,386 A | 7/1998 | Jacobs, Jr. et al. |
| 6,350,456 B1 * | 2/2002 | Reed et al. ............. 424/248.1 |

OTHER PUBLICATIONS

Cirillo et al, Molecular Microbiology, 1994, 11(4), 629-639.*
Sequence alignment for SEQ ID No:163 and Cirillo et al.*
Kalinowski et al, Molecular Microbiology, 11, 629-639, 1994.*
Wiegeshaus, E.H. et al, Reviews of Infectious Diseases, vol. 11, Suppl. 2, (Mar.-Apr. 1989, p. S484-S490.*
Griffin et al, Trends in Microbiology, vol. 3, No. 11, Nov. 1995.*
Sequence alignment for *Corynebacterium glutamicum*.*
Sequence alignment for *Mycobacterium smegmatis*, EMBL-EBI, Accession No. P41403, created Nov. 1995.*
Kozak et al, Microbiological Review, Mar. 1983, p. 1-45.*
Lewin, Genes IV, Oxford University Press, 1990, Chapter 7.*
Wiegeshaus, E.H. et al, Reviews of Infectious Diseases, vol. 11, Suppl. 2, (Mar. - Apr. 1989, p. S484-S490).*
Griffin et al, Trends in Microbiology, vol. 3, No. 11, Nov. 1995.*

* cited by examiner

*Primary Examiner*—Lynette R. F. Smith
*Assistant Examiner*—Vanessa L. Ford
(74) *Attorney, Agent, or Firm*—Townsend and Townsend and Crew LLP

(57) ABSTRACT

Compounds and methods for diagnosing tuberculosis or for inducing protective immunity against tuberculosis are disclosed. The compounds provided include polypeptides that contain at least one immunogenic portion of one or more *Mycobacterium* proteins and DNA molecules encoding such polypeptides. Diagnostic kits containing such polypeptides or DNA sequences and a suitable detection reagent may be used for the detection of *Mycobacterium* infection in patients and biological samples. Antibodies directed against such polypeptides are also provided. In addition, such compounds may be formulated into vaccines and/or pharmaceutical compositions for immunization against *Mycobacterium* infection.

14 Claims, 11 Drawing Sheets

>mTCC#3His.seq
ATGCATCACCATCACCATCACATGAATTATTCGGTGTTGCCGCCGGAGATTAATTCGTTGCGGATG
TTTACCGGTGCGGG
GTCTGCGCCGATGCTTGCGGCATCGGTGGCTTGGGATGGTTTGGCCGCGGAGTTGGCGGTGGCGGC
GTCCTCGTTTGGGT
CGGTGACTTCGGGGTTGGCGGGTCAGTCCTGGCAGGGTGCGGCGGCGGCGGCGATGGCCGCGGCGG
CGGCGCCGTATGCG
GGGTGGTTGGCTGCTGCGGCGGCGCGGGCCGCTGGCGCGTCGGCTCAGGCCAAGGCGGTGGCCAGT
GCGTTTGAGGCGGC
GCGGGCGGCGACGGTGCATCCGATGCTGGTGGCGGCCAACCGTAATGCGTTTGTGCAGTTGGTGTT
GTCGAATCTGTTTG
GGCAGAATGCGCCGGCGATCGCGGCCGCTGAGGCGATGTATGAACAGATGTGGGCCGCCGATGTGG
CCGCGATGGTGGGC
TATCACGGCGGGGCATCGGCGGCCGCGGCGCAGCTGTCGTCGTGGTCAATTGGTCTGCAGCAGGCG
TTGCCAGCTGCGCC
ATCGGCGCTGGCCGCCGCGATCGGCCTCGGCAACATCGGCGTCGGGAACCTGGGCGGCGGGAACAC
CGGTGACTACAATC
TGGGCAGCGGAAATTCCGGCAACGCCAACGTAGGTAGCGGAAACTCCGGCAACGCCAATGTGGGCA
GCGGAAATGACGGT
GCCACGAATTTGGGCAGCGGAAATATCGGCAACACCAATCTCGGCAGCGGAAACGTTGGCAATGTC
AATCTGGGCAGCGG
AAACCGAGGCTTTGGAAACCTCGGCAACGGAAACTTTGGCAGTGGGAACCTGGGCAGTGGAAACAC
CGGAAGTACCAACT
TCGGCGGCGGAAATCTCGGTTCCTTCAACTTGGGCAGTGGAAACATCGGCTCCTCCAACATCGGTT
TCGGAAACAACGGC
GACAATAACCTCGGCCTCGGGAACAATGGCAACAACAACATCGGTTTTGGGCTCACCGGCGACAAC
TTGGTGGGCATTGG
CGCGCTGAACTCGGGCATCGGGAATCTAGGTTTCGGGAACTCGGGTAACAACAACATCGGTTTCTT
CAACTCTGGCAACA
ACAACGTGGGCTTCTTCAATTCGGGCAACAACAACTTCGGCTTTGGAAACGCGGGCGACATCAACA
CGGGCTTCGGAAAC
GCCGGCGACACCAACACGGGCTTCGGAAACGCCGGCTTCTTCAATATGGGCATCGGGAACGCGGGC
AACGAAGACATGGG
CGTCGGGAACGGCGGTTCCTTTAACGTGGGCGTTGGCAATGCGGGCAACCAAAGTGTGGGCTTTGG
CAACGCGGGCACCC
TAAACGTGGGCTTCGCAAACGCGGGCAGTATCAATACGGGATTCGCGAACTCGGGCAGCATCAATA
CGGGCGGTTTCGAC
TCGGGCGACCGGAACACCGGGTTTGGAAGCTCGGTCGACCAATCCGTTTCGAGCTCGGGCTTCGGC
AACACCGGCATGAA
TTCCTCAGGCTTCTTTAACACGGGCAATGTTTCGGCTGGCTATGGGAACAACGGTGACGTTCAGTC
GGGCATCAATAACA
CCAACTCCGGCGGCTTCAACGTCGGCTTCTATAACTCGGGTGCCGGCACCGTGGGCATCGCAAACT
CTGGCCTGCAGACC
ACAGGCATTGCGAACTCGGGCACCCTCAACACGGGTGTGGCGAACACGGGTGACCACAGCTCGGGG
GGCTTCAATCAGGG
CAGTGACCAGTCGGGCTTCTTCGGTCAGCCCTAA

FIG. 3.

>mTCC#3-His.pro
MHHHHHHMNYSVLPPEINSLRMFTGAGSAPMLAASVAWDGLAAELAVAASSFGSVTSGLAGQSWQG
AAAAAMAAAAAPYA
GWLAAAAARAAGASAQAKAVASAFEAARAATVHPMLVAANRNAFVQLVLSNLFGQNAPAIAAAEAM
YEQMWAADVAAMVG
YHGGASAAAAQLSSWSIGLQQALPAAPSALAAAIGLGNIGVGNLGGGNTGDYNLGSGNSGNANVGS
GNSGNANVGSGNDG
ATNLGSGNIGNTNLGSGNVGNVNLGSGNRGFGNLGNGNFGSGNLGSGNTGSTNFGGGNLGSFNLGS
GNIGSSNIGFGNNG
DNNLGLGNNGNNNIGFGLTGDNLVGIGALNSGIGNLGFGNSGNNNIGFFNSGNNNVGFFNSGNNNF
GFGNAGDINTGFGN
AGDTNTGFGNAGFFNMGIGNAGNEDMGVGNGGSFNVGVGNAGNQSVGFGNAGTLNVGFANAGSINT
GFANSGSINTGGFD
SGDRNTGFGSSVDQSVSSSGFGNTGMNSSGFFNTGNVSAGYGNNGDVQSGINNTNSGGFNVGFYNS
GAGTVGIANSGLQT
TGIANSGTLNTGVANTGDHSSGGFNQGSDQSGFFGQP.

*FIG. 4.*

```
ggatccgaat tctgcacgag ggkygacgac gamctttgca cacgagcgat  50
ggcaaccctc acgtccgcgc aaaccccgcg cgaggccgta gagcaattcg 100
tcgagctgat ggtcgacgat ccggtgcgcg ggcgcgtgct gttgctggcg 150
ccggcggtag aaccggccct gacccggtcg ggcgcggagt ggatgcccaa 200
cttcatcgag ttgctgcaac gcaagttgtc ccgcatcgtt gatccagttc 250
tgcagaaact ggtcgccacc agcttgatcg gcgctcttac cggtctgttc 300
accgcatatc tgaacggacg gctgggagcc acccgcaagc aattcatcga 350
ctactgcgtc aacatgttgc tcagcaccgc cgcacctacg caccgcaccg 400
cgagcgggga gaatccgaac a                                421
```
*FIG. 5.*

```
gatccgaatt cggcacgagt cgaggccacc gcttccatgg ccaggccacg  50
atyttgatcg gcgtggtggc cacgcccggt gtgaagtgct gttggccgtg 100
atgtcggatt acagtctcgg cgtgcccgac gagacaggcc ttggtgctga 150
cgcggcgcgc gcgtgaagtg gcgctgacac agcacattgg ggtatccgcg 200
gagaccgatc gggccgtcgt ccccaagctg cgccaggcct atgacagcct 250
ggtgtgcggt cgccgccggc ttggcgccat ggagccgag atcgagaacg 300
cggtggccca tcagcgcgcg ctgggccttg acacccggc cggtgcccgt 350
aacttctccc ggtttctcgc caccaaagca cacgacatca cgcgagtgct 400
ggcagcaacc gccgcggaat cccaggccgg cgcggcgcgg ttgcgatccc 450
tggcttcgtc ctatcaggct gtgggatttg gccccaaacc ccaggagccg 500
cctccggatc cagtgccatt tccgccctac cagccgaagg tgtgggcggc 550
gtgccgggcg cgtggccaag acccggacaa ggtcgtcagg acgttccatc 600
acgcgccgat gagcgcgaga ttccgctcgc ttactcgtgc cgaattsgga 650
tctgatatcg ccatggcctt gtcgt                            675
```
*FIG. 6.*

```
tgatcggtca atgcgcagta ctggtgacct agcgccgccg cggtggccat  50
catctcctcg atcggcgcgg acccgtccga ccagttcgaa tgcagatgca 100
gatccccgcg caatgcggca cggatcgccc ctccaccgag atcctcagcg 150
tcagcgcgta attcagccag caggtccggc tcgcggccag accaggcctg 200
ggcgatgact ttcgcggttt tgggaccgat acccgccagc gactgccagc 250
tgttggcctg gccgtgccgc tgccgc                          276
```

FIG. 7.

```
ggatccgaat tctgcacgag gangaagtca tactgccgtc atacacnttt  50
gtctytaccg ccaacgcctt cgtgttgcgc ggtggtgtgc cagtctttgt 100
cgataggcgg cccgacacgc tcaacattga tgaaactcgc atcgtagacg 150
ccatcacccc gcgaaccaag gccatcgtcc ccgttcacta tgccggcgtg 200
gcctgcgaga tggacgcgat catgaagatc gccacgcacc acaacctggc 250
ggtggtcgaa gacgcggccc aaggcgcgat ggcgtcgtat cgtgggcggg 300
cgctcggcag catcggcgac ctgggagcgc tctcatttca cgagaccaag 350
aatgtgattt ccggcgaagg cggcgccctg cttgtcaact cataagactt 400
cctgctccgg gcagakattc tcagggaaaa gggcaccaat mrcagccngc 450
ttcctt                                                456
```

FIG. 8.

```
gatatcggat cggaattcgg cacgaggtgc ccntgggggg acaactggtg  50
cacaagaggt tcgtccgtcc cggtcctntc gtatagggac aggtttcctc 100
aagtttctga cgcgcgcggc ggatagagac cgaactgtct cacgacgttc 150
taaacccagc tcgcgtgccg ctttaatggg cgaacagccc aacccttggg 200
acctgctcca gccccaggat gcgacgagcc gacatcgagg tgccaaacca 250
tcccgtcgat atggactctt ggggaagatc agcctgttat ccccggggta 300
ccttttatcc gttgagcgac acccccttcca ctcggggggtg c         341
```

FIG. 9.

```
gatccgaatt cagagcggcg acccgtgctc caagctcctt cagcgtcgtc  50
acgggctcat cctatccggc agatcagcag gcggttcctc cgcaaagtgc 100
ggctgcaacc taccgacttc gtgcgcggcg aggaacgcgc ccctgggggg 150
tatccgcccg cgtcagacaa cagtgcctcg gtctgatcgg taataggcga 200
ccgcctcgag gtccacatcc gccacctgct cgaaacgtca ggtcttgggg 250
tgcggggtgt accggacggt atgcgcccag atcgtgccgt ctcggaatac 300
gaaagtatcg actccgtcgt cgactcggct gaccgcggaa ttcgcggtcc 350
actccaggaa cagtatgtcg ccctcgaaga tttgggtctt taagtc      396
```

FIG. 10.

```
ggatccgaat tcggcacgag gagtatcagc agaggtcgga gaaggtgctg  50
accgaataca acaacaaggc agccctggaa ccggtaaacc cgccgaagcc 100
tccccccgcc atcaagatcg acccgccccc gcctccgcaa gagcagggat 150
tgatccctgg cttcctgatg cc                              172
```

FIG. 11.

```
ggatccgaat tcggcacgag ccagaacctc gcckgccccg ggcggcagng  50
acaccaactg gscaccacgc cgcggatcgg cmgagcagcg cc           92
```

FIG. 12.

```
gatccgaatt cggcacgaga agaatntgac ccnncnccng tggctgatgc  50
gagagcttnc ttntttcttc cccccantgg ttggacgggg tcgtcacagc 100
gggcattcta agtcccgcgg gccacaaaag gcagtgccgc ggaacttctt 150
ggcccaaacg ggcacccggc tacgtgcgca ccgcgaccgt cgacaactgg 200
tcggcgagcc ggtccgggga atccaccatc gagaacgtcc gtgctccctc 250
gattacctcg aaacgggcgc gcgggatggt cgcggcgagc cgttgaccgt 300
tctcgagtgc gaagaacacg tcatccgccg accacgcgat gagcgccggc 350
ttgtcgaatt caggcagccg ggcggcgact gcggtggtga cttcggtgcg 400
cagcgatagc gagagctgac gcaggtcttc ggcgatggcc gggttggata 450
gcgccggacg aacccaggcc cgggtgagat ggtcgatgtt gtggtgcgac 500
aaaccggcat acgcgcggtt tacgcgcggc cggtgcccgc atcacctgga 550
tcgcggcccg gaacagggtg gccgatttcg cggncaggat cacctgnttt 600
gaggatcgg                                              609
```

FIG. 13.

```
ggatccgaat tcggcacgag tgcggtgcct atctgcgttg gccagtacct  50
cgcggacctg gcgagtgcgg acgcgcaggc tatcgaagtg ggcctaaaga 100
cggcggacgt ggcgcccgtt gccgtacgac ctgcagcggc gccgccgttg 150
cgtgagtctg ccgcggtgcg accggaggcc aggctggtgt cggcggtggc 200
gccagctccc gcgggcacgt cggcgtcggt gctggcttcg gatcggggtg 250
ccggcgtgtt gggtttgcc gggaccgctg gcaaggantc cnttgggcgt 300
c                                                      301
```

FIG. 14.

```
ggctgctgcg cgcactcgcg ggtctgctgg acgagtggac gccggtgatc  50
gccggcgccg aactgggcga gcaccctac acgccgatca cgccggagtc 100
gatccggcgg gccgcgcagc tcggcgacga cctaccggtg gcgtggaagc 150
accgcagcga gcgctacacc gagaagctgg ccaccccga caccagcgtc 200
gccgacctgg tcggcgacgt cgacccgatc aaggttgccg agggccgcag 250
cctcggggat c                                           261
```

FIG. 15.

PREDICTED PROTEIN SEQUENCE (SEQ ID NO: 161)

VRHHEGHVAADDDQPQCASFGALTGVIEDIAENQRNAHHQKWRHGRCVEEVHLPVDVGEPRQPTGA
VADQDHRITPVPAHKHTPPRVCQDWHRQPPHRGRADQHLGLDARLCAAACNVLLVDGVQHRPQRHG
PGPRFGFPRVVVACGIRQARVEVERFGGVVPERAHGVGQRNNRVATDRLTDRMPIDRGLGREPRSV
GGQIDRERDQPQRIPAGKHVTPHCPQPRALHLVLTSRRHVERQRHRAEEQHEVHAGPLGGASQSQQ
HPGAEPPPAHTHPRSPHGGGAAAGQQSDVHPFANLIAVDDERAERRDDEERQEAVQQRGPRGDEAD
PVADQQHPGDGADQCRPADPPHDPHHQRHQDHTQQGAGEPPAESVVTEDGLPDRDQLLTDRRVNHQ
AVPGVVFHPMVVQHLPGLGCVMLLVEDGGAGIGQRAQVQEPGHRGQQRDQAGHDPAA

NECLEOTIDE SEQUENCE (SEQ ID NO: 160)

TGAGATTGGCAGACCGGTGAGCACCGGATACAGCCACGCAAAGTTCGTCACCACGAGGGCCACGTA
GCAGCAGACGACGATCAGCCCCAGTGTGCGTCGTTCGGAGCCCTGACCGGGGTGATAGAGGATATC
GCCGAGAACCAGCGAAATGCCCATCACCAGAAATGGCGCCATGGTCGCTGCGTAGAAGAAGTACAT
CTGCCGGTCGATGTCGGCGAACCACGGCAGCCAACCGGCGCAGTAGCCGACCAGGACCACCGCATA
ACGCCAGTCCCGGCGCACAAACATACGCCACCCCGCGTATGCCAGGACTGGCACCGCCAGCCACCA
CATCGCGGGCGTGCCGACCAGCATCTCGGCCTTGACGCACGACTGTGCGCCGCAGCCTGCAACGTC
TTGCTGGTCGATGGCGTACAGCACCGGCCGCAACGACATGGGCCAGGTCCACGGTTTGGATTCCCA
AGGGTGGTAGTTGCCTGCGGAATTCGTCAGGCCCGCGTGGAAGTGGAACGCTTTGGCGGTGTAGTG
CCAGAGCGAGCGCACGGCGTCGGGCAGCGGAACAACCGAGTTGCGACCGACCGCTTGACCGACCGC
ATGCCGATCGATCGCGGTCTCGGACGCGAACCACGGAGCGTAGGTGGCCAGATAGACCGCGAACGG
GATCAACCCCAGCGCATACCCGCTGGGAAGCACGTCACGCCGCACTGTCCCCAGCCACGGTCTTTG
CACTTGGTACTGACGTCGCGCCGCCACGTCGAACGCCAGCGCCATCGCGCCGAAGAACAGCACGAA
GTACACGCCGGACCACTTGGTGGCGCAAGCCAATCCCAGCAGCACCCCGGCGCCGAACCGCCACCA
GCGCACACCCACCCGCGGTCCCCACACGGTGGCGGCGCTGCGGCCGGCCAGCAGAGCGATGTGCAT
CCGTTCGCGAACCTGATCGCGGTCGACGATGAGCGCGCCGAACGCCGCGACGACGAAGAACGTCAG
GAAGCCGTCCAGCAGCGCGGTCCGCGCGGTGACGAAGCTGACCCCGTCGCAGATCAGCAGCACCCC
GGCGATGGCGCCGACCAATGTCGACCGGCTGATCCGCCGCACGATCCGCACCACCAGCGCCACCAG
GACCACACCCAGCAGGGCGCCGGTGAACCGCCAGCCGAATCCGTTGTAACCGAAGATGGCCTCCCC
GATCGCGATCAGCTGCTTACCGACCGGCGGGTGAACCACCAGGCCGTACCCGGGGTTGTCTTCCAC
CCCATGGTTGTTCAGCACCTGCCAGGCCTGGGGTGCGTAATGCTTCTCGTCGAAGATGGGGGTGCC
GGCATCGGTCAGCGAGCCCAGGTTCAGGAACCGGGTCACCGTGGCCAGCAGCGTGATCAGGCCGGT
CACGATCCAGCCGCGTAA

NOTES: UNKNOWN PROTEIN FROM COSMID MTCI237

FIG. 16.

MO-2
PREDICTED PROTEIN SEQUENCE (SEQ ID NO: 163)

VALVVQKYGGSSVADAERIRRVAERIVATKKQGNDVVVVVSAMGDTTDDLLDLAQQVCPAPPPREL
DMLLTAGERISNALVAMAIESLGAHARSFTGSQAGVITTGTHGNAKIIDVTPGRLQTALEEGRVVL
VAGFQGVSQDTKDVTTLGRGGSDTTAVAMAAALGADVCEIYTDVDGIFSADPRIVRNARKLDTVTF
EEMLEMAACGAKVLMLRCVEYARRHNIPVHVRSSYSDRPGTVVVGSIKDVPMEDPILTGVAHDRSE
AKVTIVGLPDIPGYAAKVFRAVADADVNIDMVLQNVSKVEKGKTDITFTCSRDVGPAAVEKLDSLR
NEIGFSQLLYDDHIGKVSLIGAGMRSHPGVTATFCEALAAVGVNIELISTSEIRISVLCRDTELDK
AVVALHEAFGLGGDEEATVYAGTGR

NUCLEOTIDE SEQUENCE (SEQ ID NO. 162)

GTGGCGCTCGTCGTGCAGAAGTACGGCGGATCCTCGGTGGCCGACGCCGAACGGATTCGCCGCGTC
GCCGAACGCATCGTCGCCACCAAGAAGCAAGGCAATGACGTCGTCGTCGTCGTCTGCCATGGGGGA
TACCACCGACGACCTGCTGGATCTGGCTCAGCAGGTGTGCCCGGCGCCGCCGCCTCGGGAGCTGGA
CATGCTGCTTACCGCCGGTGAACGCATCTCGAATGCGTTGGTGGCCATGGCCATCGAGTCGCTCGG
CGCGCATGCCCGGTCGTTCACCGGTTCGCAGGCCGGGGTGATCACCACCGGCACCCACGGCAACGC
CAAGATCATCGACGTCACGCCGGGGCGGCTGCAAACCGCCCTTGAGGAGGGGCGGGTCGTTTTGGT
GGCCGGATTCCAAGGGGTCAGCCAGGACACCAAGGATGTCACGACGTTGGGCCGCGGCGGCTCGGA
CACCACCGCCGTCGCCATGGCCGCCGCGCTGGGTGCCGATGTCTGTGAGATCTACACCGACGTGGA
CGGCATCTTCAGCGCCGACCCGCGCATCGTGCGCAACGCCCGAAAGCTCGACACCGTGACCTTCGA
GGAAATGCTCGAGATGGCGGCCTGCGGCGCCAAGGTGCTGATGCTGCGCTGCGTGGAATACGCTCG
CCGCCATAATATTCCGGTGCACGTCCGGTCGTCGTACTCGGACAGACCGGGCACCGTCGTTGTCGG
ATCGATCAAGGACGTACCCATGGAAGACCCCATCCTGACCGGAGTCGCGCACGACCGCAGCGAGGC
CAAGGTGACCATCGTCGGGCTGCCCGACATCCCCGGGTATGCGGCCAAGGTGTTTAGGGCGGTGGC
CGACGCCGACGTCAACATCGACATGGTGCTGCAGAACGTCTCCAAGGTCGAGGACGGCAAGACCGA
CATCACCTTCACCTGCTCCCGCGACGTCGGGCCCGCCGCCGTGGAAAAACTGGACTCGCTCAGAAA
CGAGATCGGCTTCTCACAGCTGCTGTACGACGACCACATCGGCAAGGTATCGCTGATCGGTGCCGG
CATGCGCAGCCACCCCGGGGTCACCGCGACGTTCTGTGAGGCGCTGGCGGCGGTGGGGGTCAACAT
CGAGCTGATCTCCACCTCGGAGATCAGGATCTCGGTGTTGTGCCGCGACACCGAACTGGACAAGGC
CGTGGTCGCGCTGCATGAAGCGTTCGGGCTCGGCGGCGACGAGGAGGCCACGGTGTACGCGGGGAC
GGGACGGTAGATGGGCCTGTCAATAGGGATCGTGGGGCCACCGGTCAGGTGGGTCAGGTCATGCG
CACGTTGCTCGACGAGCGGGATTTCCCGGCGAGCGCGGTGCGGTTCTTCGCGTCGGCCCGATCGCA
GGGCCGCAAGCTGGCCTTCCGCGGCCAGGAGATCGAAGTGGAAGACGCCGAGACGGCCGACCCGAG
CGGGCTGGATATCGCGTTGTTCTCCGCCGGCTCGGCCATGTCGAAGGTGCAGGCGCCCCGCTTTGC
GGCGGCCGGAGTCACGGTGATCGACAACTCGTCGGCGTGGCGTAAGGACCCCGACGTGCCGTTGGT
GGTGTCCGAGGTGAACTTTGAACGCGACGCGCACCGCCGGCCCAAGGCTCGTGCCGCTCGTGCCGA
ATTCGGCACGAGCCGACGTGGTCGGCAACGTCCTGGATCGCGGGCAGCTGGTTGTTGAGGATGAAT
CCGTCCACCAGGTGGTAGGAGCCGAACGAAGATTCCACCGTCGTCGTCAACGTGGCCGCATTGCCG
TACGAATCGACGACGCTGAGGTGGCTGGTGCCATGCTCAGGCACTGGCGGGGCGACGGCCGTCGGT
GCGCCGAAGTCCC

NOTES: M.tb aspartokinase

*FIG. 17.*

>Full-length TbH4/XP-1 (MTB48) Open Reading Frame (SEQ ID NO: 164)

ATGACGCAGTCGCAGACCGTGACGGTGGATCAGCAAGAGATTTTGAACAGGGCCAACGAGGTGGAG
GCCCCGATGGCGGACCCACCGACTGATGTCCCCATCACACCGTGCGAACTCACGGCGGCTAAAAAC
GCCGCCCAACAGCTGGTATTGTCCGCCGACAACATGCGGGAATACCTGGCGGCCGGTGCCAAAGAG
CGGCAGCGTCTGGCGACCTCGCTGCGCAACGCGGCCAAGGCGTATGGCGAGGTTGATGAGGAGGCT
GCGACCGCGCTGGACAACGACGGCGAAGGAACGTGCAGGCAGAATCGGCCGGGGCCGTCGGAGGGG
ACAGTTCGGCCGAACTAACCGATACGCCGAGGGTGGCCACGGCCGGTGAACCCAACTTCATGGATC
TCAAAGAAGCGGCAAGGAAGCTCGAAACGGGCGACCAAGGCGCATCGCTCGCGCACTTTGCGGATG
GGTGGAACACTTTCAACCTGACGCTGCAAGGCGACGTCAAGCGGTTCCGGGGGTTTGACAACTGGG
AAGGCGATGCGGCTACCGCTTGCGAGGCTTCGCTCGATCAACAACGGCAATGGATACTCCACATGG
CCAAATTGAGCGCTGCGATGGCCAAGCAGGCTCAATATGTCGCGCAGCTGCACGTGTGGGCTAGGC
GGGAACATCCGACTTATGAAGACATAGTCGGGCTCGAACGGCTTTACGCGGAAAACCCTTCGGCCC
GCGACCAAATTCTCCCGGTGTACGCGGAGTATCAGCAGAGGTCGGAGAAGGTGCTGACCGAATACA
ACAACAAGGCAGCCCTGGAACCGGTAAACCCGCCGAAGCCTCCCCCCGCCATCAAGATCGACCCGC
CCCCGCCTCCGCAAGAGCAGGGATTGATCCCTGGCTTCCTGATGCCGCCGTCTGACGGCTCCGGTG
TGACTCCCGGTACCGGGATGCCAGCCGCACCGATGGTTCCGCCTACCGGATCGCCGGGTGGTGGCC
TCCCGGCTGACACGGCGGCGCAGCTGACGTCGGCTGGGCGGGAAGCCGCAGCGCTGTCGGGCGACG
TGGCGGTCAAAGCGGCATCGCTCGGTGGCGGTGGAGGCGGCGGGGTGCCGTCGGCGCCGTTGGGAT
CCGCGATCGGGGGCGCCGAATCGGTGCGGCCCGCTGGCGCTGGTGACATTGCCGGCTTAGGCCAGG
GAAGGGCCGGCGGCGGCGCCGCGCTGGGCGGCGGTGGCATGGGAATGCCGATGGGTGCCGCGCATC
AGGGACAAGGGGGCGCCAAGTCCAAGGGTTCTCAGCAGGAAGACGAGGCGCTCTACACCGAGGATC
GGGCATGGACCGAGGCCGTCATTGGTAACCGTCGGCGCCAGGACAGTAAGGAGTCGAAG

*FIG. 18.*

COMPOUNDS AND METHODS FOR DIAGNOSIS AND IMMUNOTHERAPY OF TUBERCULOSIS

CROSS-REFERENCES TO RELATED APPLICATIONS

The present application claims priority to patent application No. 60/185,037, filed Feb. 25, 2000; and patent application No. 60/223,828, filed Aug. 8, 2000, herein each incorporated by reference in its entirety.

The present application is related to U.S. patent application Ser. Nos. 08/859,381, filed May 20, 1997 (abandoned); 08/858,998, filed May 20, 1997 (abandoned); 09/073,010, filed May 5, 1998; and 09/073,009, filed May 5, 1998; and to PCT application Nos. PCT/US98/10407, filed May 20, 1998; and PCT/US98/10514, filed May 20, 1998, herein each incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Tuberculosis is a chronic, infectious disease, that is generally caused by infection with *Mycobacterium tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If left untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

Inhibiting the spread of tuberculosis will require effective vaccination and accurate, early diagnosis of the disease. Currently, vaccination with live bacteria is the most efficient method for inducing protective immunity. The most common *Mycobacterium* employed for this purpose is *Bacillus* Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. *Mycobacterium*-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1.25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection, see Chan and Kaufmann, in *Tuberculosis: Pathogenesis, Protection and Control*, Bloom (ed.), ASM Press. Washington, D.C. (1994).

Accordingly, there is a need in the art for improved diagnostic methods for detecting tuberculosis, as well as for vaccines and methods for preventing the infection. The present invention fulfills this need and further provides other related advantages.

SUMMARY OF THE INVENTION

Briefly stated, the present invention provides compounds and methods for preventing and diagnosing tuberculosis.

In one embodiment, polypeptides are provided that comprise an immunogenic portion of a *Mycobacterium* antigen, preferably a *Mycobacterium tuberculosis* antigen, or a variant of such an antigen that differs only in conservative substitutions and/or modifications, wherein the antigen comprises an amino acid sequence encoded by a polynucleotide having the nucleotide sequence recited in SEQ ID NO:145, 149, 150, 151, 152, 153, 154, 155, 156, 157, 158, 159, 160, 162, and 164, the complements of said sequences, or a nucleotide sequence that hybridizes to the sequence set forth in SEQ ID NO:145, 149, 150, 151, 152, 153, 154, 155, 156, 157, 158, 159, 160, 162, and 164, or an immunogenic fragment thereof. In a second embodiment, the present invention provides polypeptides comprising an immunogenic portion of a *Mycobacterium* antigen, preferably a *Mycobacterium tuberculosis* antigen, having the amino acid sequence described in SEQ ID NO:146, 161, or 163 or variants or immunogenic fragments thereof.

In related aspects, nucleotide sequences encoding the above polypeptides, recombinant expression vectors comprising these nucleotide sequences and host cells transformed or transfected with such expression vectors are also provided. In particular, the present invention provides an isolated polynucleotide that specifically hybridizes under moderately stringent conditions to a second polynucleotide comprising a nucleotide sequence selected from the group consisting of SEQ ID NO:145, 149, 150, 151, 152, 153, 154, 155, 156, 157, 158, 159, 160, 162, and 164. In some embodiments, the isolated polynucleotide specifically hybridizes to the second polynucleotide under highly stringent conditions.

In another aspect, the present invention provides fusion proteins comprising a first polypeptide encoded by a polynucleotide having the sequence set forth in SEQ ID NO:145, 149, 150, 151, 152, 153, 154, 155, 156, 157, 158, 159, 160, 162, and 164, or a fragment thereof, and a second polypeptide. In one embodiment, the first and second polypeptides are heterologous. Alternatively, the fusion proteins of the invention may comprise a first polypeptide encoded by a polynucleotide having a sequence selected from the group consisting of SEQ ID NO:145, 149, 150, 151, 152, 153, 154, 155, 156, 157, 158, 159, 160, 162, and 164, or an immunogenic fragment thereof, and a known *Mycobacterium* antigen, preferably a *M. tuberculosis* antigen.

In further aspects of the subject invention, methods and diagnostic kits are provided for detecting *Mycobacterium* infection in a patient. The methods comprise contacting a biological sample with at least one of the above polypeptides and detecting in the sample the presence of antibodies that bind to the polypeptide or polypeptides, thereby detecting *Mycobacterium* infection in the biological sample. In a preferred embodiment, the *Mycobacterium* infection is a *M. tuberculosis* infection.

Suitable biological samples include whole blood, sputum, serum, plasma, saliva, cerebrospinal fluid and urine. The diagnostic kits comprise one or more of the above polypeptides in combination with a detection reagent.

The present invention also provides methods for detecting *Mycobacterium* infection, comprising obtaining a biological sample from a patient, contacting the sample with at least one oligonucleotide primer in a polymerase chain reaction, the oligonucleotide primer being specific for a nucleotide sequence encoding the above polypeptides, and detecting in the sample a nucleotide sequence that amplifies in the presence of the first and second oligonucleotide primers. In one embodiment, the oligonucleotide primer comprises at least about 10 contiguous nucleotides of such a nucleotide sequence. In a preferred embodiment, the *Mycobacterium* infection is a *M. tuberculosis* infection.

In a further aspect, the present invention provides a method for detecting *Mycobacterium* infection in a patient, comprising obtaining a biological sample from the patient, contacting the sample with an oligonucleotide probe specific for a nucleotide sequence encoding the above polypeptides, and detecting in the sample a nucleotide sequence that hybridizes to the oligonucleotide probe. In one embodiment, the oligonucleotide probe comprises at least about 15 contiguous nucleotides of such a nucleotide sequence. In a preferred embodiment, the *Mycobacterium* infection is a *M. tuberculosis* infection.

In yet another aspect, methods are provided for detecting *Mycobacterium* infection in a patient, such methods comprising the steps of contacting a biological sample with a polypeptide, wherein the polypeptide comprises an amino acid sequence encoded by a polynucleotide having a nucleotide sequence selected from the group consisting of SEQ ID NO:145, 149, 150, 151, 152, 153, 154, 155, 156, 157, 158, 159, 160, 162, and 164, the complements of said sequences, or a nucleotide sequence that hybridizes to a sequence selected from the group consisting of SEQ ID NO:145, 149, 150, 151, 152, 153, 154, 155, 156, 157, 158, 159, 160, 162, and 164, or an immunogenic fragment thereof, and detecting in the sample the presence of antibodies that bind to the polypeptide, thereby detecting *Mycobacterium* infection in the biological sample. In a preferred embodiment, the *Mycobacterium* infection is a *M. tuberculosis* infection. Diagnostic kits for use in such methods are also provided.

In another aspect, the present invention provides antibodies, both polyclonal and monoclonal, that bind to the polypeptides described above, as well as methods for their use in the detection of *Mycobacterium* infection.

Within other aspects, the present invention provides pharmaceutical compositions that comprise one or more of the above polypeptides, or a polynucleotide encoding such polypeptides, and a physiologically acceptable carrier or an adjuvant, e.g., SBAS-2, QS-21, ENHANZYN (Detox), MPL, 3D-MPL, CWS, GM-CSF, SAF, ISCOMS, MF-59, RC-529, AS2, AS2', AS2", AS4, AS6, TDM, AGP, CPG, Leif, saponin, and saponin mimetics, and derivatives thereof or mixtures thereof. In another aspect, the present invention provides pharmaceutical compositions that comprise one or more of the above polypeptides, or a polynucleotide encoding such polypeptides, and an adjuvant such as BCG. In another aspect the present invention provides methods in which one or more of the above polypeptides, or a polynucleotide encoding such polypeptides is administered to a subject who has been exposed to BCG. The invention also provides vaccines comprising one or more of the polypeptides as described above and a non-specific immune response enhancer, together with vaccines comprising one or more polynucleotides encoding such polypeptides and a non-specific immune response enhancer.

In yet another aspect, methods are provided for inducing protective immunity in a patient, comprising administering to a patient an effective amount of one or more of the above polypeptides.

In further aspects of this invention, methods and diagnostic kits are provided for detecting tuberculosis in a patient. The methods comprise contacting dermal cells of a patient with one or more of the above polypeptides and detecting an immune response on the patient's skin. The diagnostic kits comprise one or more of the above polypeptides in combination with an apparatus sufficient to contact the polypeptide(s) with the dermal cells of a patient.

In yet another aspect, methods are provided for detecting tuberculosis in a patient, such methods comprising contacting dermal cells of a patient with one or more polypeptides encoded by a nucleotide sequence selected from the group consisting of SEQ ID NO:145, 149, 150, 151, 152, 153, 154, 155, 156, 157, 158, 159, 160, 162, and 164, the complements of said sequences, or nucleotide sequences that hybridize to a sequence selected from the group consisting of SEQ ID NO:145, 149, 150, 151, 152, 153, 154, 155, 156, 157, 158, 159, 160, 162, and 164, and detecting an immune response on the patient's skin. Diagnostic kits for use in such methods are also provided.

In additional aspects of the invention, methods are provided for inhibiting the development of a *Mycobacterium* infection in a patient. In one embodiment, inhibiting the development of a *Mycobacterium* infection comprises administering to a patient an effective amount of a pharmaceutical composition or a vaccine of the invention. In another embodiment, inhibiting the development of a *Mycobacterium* infection in the patient comprises administering to a patient an effective amount of an antibody of the invention. In a preferred embodiment, the *Mycobacterium* infection is a *M. tuberculosis* infection.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 3 shows the nucleotide sequence of mTTC#3 (SEQ ID NO:145).

FIG. 4 shows the amino acid sequence of mTCC#3 (SEQ ID NO:146).

FIG. 5 shows the 5' nucleotide sequence of P1 (SEQ ID NO:149).

FIG. 6 shows the nucleotide sequence of P2 (SEQ ID NO:150).

FIG. 7 shows the 3' nucleotide sequence of P3 (SEQ ID NO:151).

FIG. 8 shows the nucleotide sequence of P4 (SEQ ID NO:152).

FIG. 9 shows the nucleotide sequence of P6 (SEQ ID NO:153)

FIG. 10 shows the nucleotide sequence of P7 (SEQ ID NO:154)

FIG. 11 shows the nucleotide sequence of P8 (SEQ ID NO:155)

FIG. 12 shows the nucleotide sequence of P9 (SEQ ID NO:156)

FIG. 13 shows the 5' nucleotide sequence of P10 (SEQ ID NO:157)

FIG. 14 shows the 5' nucleotide sequence of P11 (SEQ ID NO:158)

FIG. 15 shows the 3' nucleotide sequence of P12 (SEQ ID NO:159)

FIG. 16 shows the full length nucleotide and amino acid sequence of MO-1 (SEQ ID NO:160 (nucleotide) and SEQ ID NO:161 (amino acid).

FIG. 17 shows the full length nucleotide and amino acid sequence of MO-2 (SEQ ID NO:162 (nucleotide) and SEQ ID NO:163 (amino acid).

FIG. 18 shows the full length nucleotide sequence of TbH4/XP-1 (MTB48) (SEQ ID NO:164).

Figure 1A:
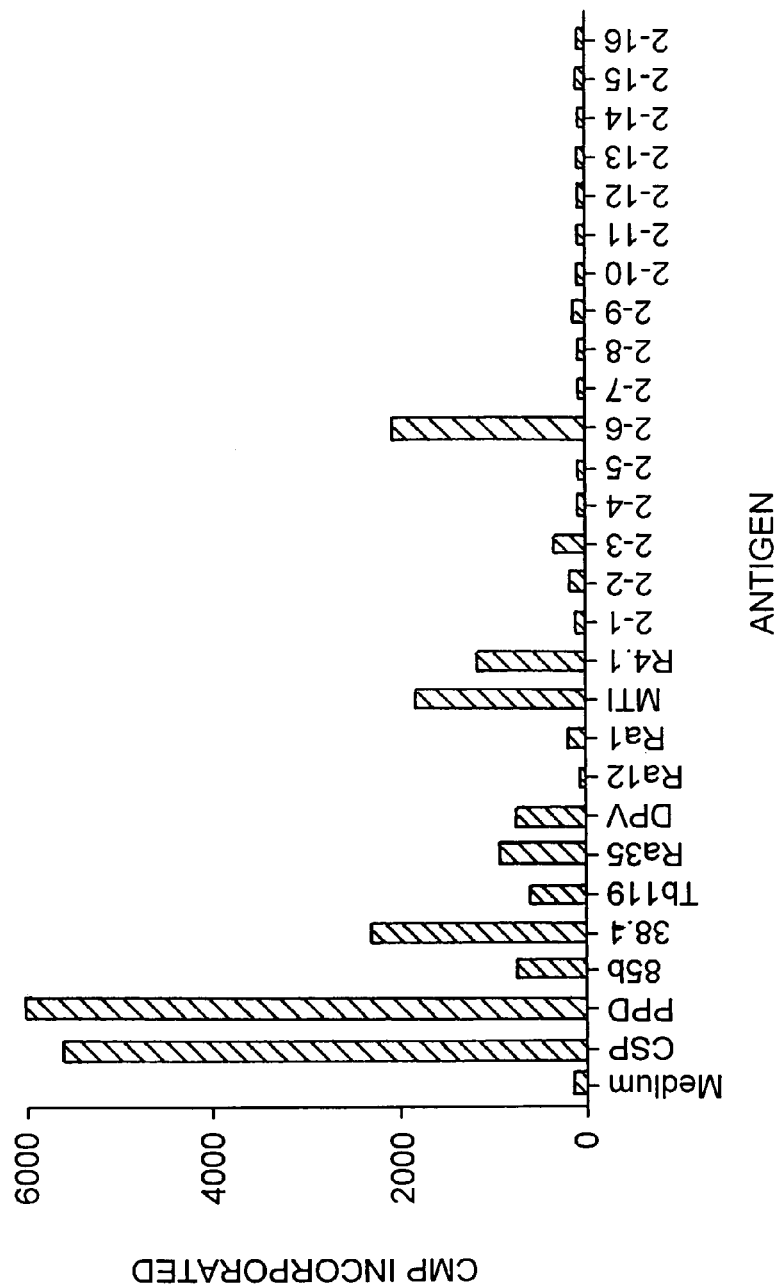
FIGS. 1A and 1B illustrate the stimulation of proliferation and interferon-γ production, respectively, in T cells derived from a first PPD-positive donor (referred to as D7) by recombinant ORF-2 and synthetic peptides to ORF-2.

SEQ ID NO:1 is the cDNA sequence of Tb224
SEQ ID NO:2 is the cDNA sequence of Tb636
SEQ ID NO:3 is the cDNA sequence of Tb424
SEQ ID NO:4 is the cDNA sequence of Tb436
SEQ ID NO:5 is the cDNA sequence of Tb398
SEQ ID NO:6 is the cDNA sequence of Tb508
SEQ ID NO:7 is the cDNA sequence of Tb441
SEQ ID NO:8 is the cDNA sequence of Tb475
SEQ ID NO:9 is the cDNA sequence of Tb488
SEQ ID NO:10 is the cDNA sequence of Tb465
SEQ ID NO:11 is the cDNA sequence of Tb431
SEQ ID NO:12 is the cDNA sequence of Tb472
SEQ ID NO:13 is the predicted amino acid sequence of Tb224
SEQ ID NO:14 is the predicted amino acid sequence of Tb636
SEQ ID NO:15 is the predicted amino acid sequence of Tb431
SEQ ID NO:16 is the amino acid sequence of Tb424 ORF-1
SEQ ID NO:17 is the amino acid sequence of Tb424 ORF-2
SEQ ID NO:18 is the amino acid sequence of Tb436 ORF-1
SEQ ID NO:19 is the amino acid sequence of Tb436 ORF-2
SEQ ID NO:20 is the amino acid sequence of Tb398 ORF-2
SEQ ID NO:21 is the amino acid sequence of Tb398 ORF-2

SEQ ID NO:22 is the amino acid sequence of Tb508 ORF-1

SEQ ID NO:23 is the amino acid sequence of Tb508 ORF-2

SEQ ID NO:24 is the amino acid sequence of Tb441 ORF-1

SEQ ID NO:25 is the amino acid sequence of Tb441 ORF-2

SEQ ID NO:26 is the amino acid sequence of Tb475 ORF-1

SEQ ID NO:27 is the amino acid sequence of Tb475 ORF-2

SEQ ID NO:28 is the amino acid sequence of Tb488 ORF-1

SEQ ID NO:29 is the amino acid sequence of Tb488 ORF-2

SEQ ID NO:30 is the amino acid sequence of Tb465 ORF-1

SEQ ID NO:31 is the amino acid sequence of Tb465 ORF-2

SEQ ID NO:32 is the amino acid sequence of Tb424 ORF-U

SEQ ID NO:33 is the amino acid sequence of Tb436 ORF-U

SEQ ID NO:34 is the amino acid sequence of ORF-1-1

SEQ ID NO:35 is the amino acid sequence of ORF-1-2

SEQ ID NO:36 is the amino acid sequence of ORF-1-3

SEQ ID NO:37 is the amino acid sequence of ORF-1-4

SEQ ID NO:38 is the amino acid sequence of ORF-1-5

SEQ ID NO:39 is the amino acid sequence of ORF-1-6

SEQ ID NO:40 is the amino acid sequence of ORF-1-7

SEQ ID NO:41 is the amino acid sequence of ORF-1-8

SEQ ID NO:42 is the amino acid sequence of ORF-1-9

SEQ ID NO:43 is the amino acid sequence of ORF-1-10

SEQ ID NO:44 is the amino acid sequence of ORF-1-11

SEQ ID NO:45 is the amino acid sequence of ORF-1-12

SEQ ID NO:46 is the amino acid sequence of ORF-1-13

SEQ ID NO:47 is the amino acid sequence of ORF-1-14

SEQ ID NO:48 is the amino acid sequence of ORF-1-15

SEQ ID NO:49 is the amino acid sequence of ORF-1-16

SEQ ID NO:50 is the amino acid sequence of ORF-1-17

SEQ ID NO:51 is the amino acid sequence of ORF-2-1

SEQ ID NO:52 is the amino acid sequence of ORF-2-2

SEQ ID NO:53 is the amino acid sequence of ORF-2-3

SEQ ID NO:54 is the amino acid sequence of ORF-2-4

SEQ ID NO:55 is the amino acid sequence of ORF-2-5

SEQ ID NO:56 is the amino acid sequence of ORF-2-6

SEQ ID NO:57 is the amino acid sequence of ORF-2-7

SEQ ID NO:58 is the amino acid sequence of ORF-2-8

SEQ ID NO:59 is the amino acid sequence of ORF-2-9

SEQ ID NO:60 is the amino acid sequence of ORF-2-10

SEQ ID NO:61 is the amino acid sequence of ORF-2-11

SEQ ID NO:62 is the amino acid sequence of ORF-2-12

SEQ ID NO:63 is the amino acid sequence of ORF-2-13

SEQ ID NO:64 is the amino acid sequence of ORF-2-14

SEQ ID NO:65 is the amino acid sequence of ORF-2-15

SEQ ID NO:66 is the amino acid sequence of ORF-2-16

SEQ ID NO:67 is the amino acid sequence of ORF-2-17

SEQ ID NO:68 is the amino acid sequence of ORF-2-18

SEQ ID NO:69 is the amino acid sequence of ORF-2-19

SEQ ID NO:70 is the amino acid sequence of ORF-2-20

SEQ ID NO:71 is the amino acid sequence of ORF-2-21

SEQ ID NO:72 is the amino acid sequence of ORF-2-22

SEQ ID NO:73 is the amino acid sequence of ORF-2-23

SEQ ID NO:74 is the amino acid sequence of ORF-2-24

SEQ ID NO:75 is the amino acid sequence of ORF-2-25

SEQ ID NO:76 is the amino acid sequence of ORF-2-26

SEQ ID NO:77 is the amino acid sequence of ORF-2-27
SEQ ID NO:78 is the amino acid sequence of ORF-2-28
SEQ ID NO:79 is the amino acid sequence of ORF-2-29
SEQ ID NO:80 is the amino acid sequence of ORF-2-30
SEQ ID NO:81–82 are the amino acid sequence of two overlapping peptides to the open reading frame of Tb224
SEQ ID NO:83 is the full-length cDNA sequence of Tb431 (which contains an ORF encoding Mtb-40)
SEQ ID NO:84 is the amino acid sequence of MSF-1
SEQ ID NO:85 is the amino acid sequence of MSF-2
SEQ ID NO:86 is the anino acid sequence of MSF-3
SEQ ID NO:87 is the amino acid sequence of MSF-4
SEQ ID NO:88 is the amino acid sequence of MSF-5
SEQ ID NO:89 is the amino acid sequence of MSF-6
SEQ ID NO:90 is the amino acid sequence of MSF-7
SEQ ID NO:91 is the amino acid sequence of MSF-8
SEQ ID NO:92 is the amino acid sequence of MSF-9
SEQ ID NO:93 is the amino acid sequence of MSF-10
SEQ ID NO:94 is the amino acid sequence of MSF-11
SEQ ID NO:95 is the amino acid sequence of MSF-12
SEQ ID NO:96 is the amino acid sequence of MSF-13
SEQ ID NO:97 is the amino acid sequence of MSF-14
SEQ ID NO:98 is the amino acid sequence of MSF-15
SEQ ID NO:99 is the amino acid sequence of MSF-16
SEQ ID NO:100 is the amino acid sequence of MSF-17
SEQ ID NO:101 is the amino acid sequence of MSF-18
SEQ ID NO:102 is the cDNA sequence of Tb867
SEQ ID NO:103 is the cDNA sequence of Tb391
SEQ ID NO:104 is the cDNA sequence of Tb470
SEQ ID NO:105 is the cDNA sequence of Tb838
SEQ ID NO:106–107 are the cDNA sequences of Tb962
SEQ ID NO:108 is the full-length cDNA sequence of Tb472
SEQ ID NO:109 is the predicted amino acid sequence of the protein encoded by Tb472 (referred to as MSL)
SEQ ID NO:110 is the amino acid sequence of MSL-1
SEQ ID NO:111 is the amino acid sequence of MSL-2
SEQ ID NO:112 is the amino acid sequence of MSL-3
SEQ ID NO:113 is the amino acid sequence of MSL-4
SEQ ID NO:114 is the amino acid sequence of MSL-5
SEQ ID NO:115 is the amino acid sequence of MSL-6
SEQ ID NO:116 is the amino acid sequence of MSL-7
SEQ ID NO:117 is the amino acid sequence of MSL-8
SEQ ID NO:118 is the amino acid sequence of MSL-9
SEQ ID NO:119 is the amino acid sequence of MSL-10
SEQ ID NO:120 is the amino acid sequence of MSL-11
SEQ ID NO:121 is the amino acid sequence of MSL-12
SEQ ID NO:122 is the amino acid sequence of MSL-13
SEQ ID NO:123 is the amino acid sequence of MSL-14
SEQ ID NO:124 is the amino acid sequence of MSL-15
SEQ ID NO:125 is the DNA sequence of the full-length open reading frame of Tb470 (which encodes Mtb-40)
SEQ ID NO:126 is the determined amino acid sequence of Mtb-40
SEQ ID NO:127 is the cDNA sequence of Tb366
SEQ ID NO:128 is the cDNA sequence of Tb433
SEQ ID NO:129 is the cDNA sequence of Tb439
SEQ ID NO:130–131 are the cDNA sequences of Tb372
SEQ ID NO:132 is the cDNA sequence of Tb390R5C6
SEQ ID NO:133–134 are the cDNA sequences of Tb390R2C11
SEQ ID NO:135 is the 5' cDNA sequence of Y1-26C1
SEQ ID NO:136 is the 5' cDNA sequence of Y1-86C11
SEQ ID NO:137 is the full-length cDNA sequence of hTcc#1
SEQ ID NO:138 is the predicted amino acid sequence of hTcc#1
SEQ ID NO:139 is the cDNA sequence of mTCC#1
SEQ ID NO:140 is the cDNA sequence of mTCC#2
SEQ ID NO:141 is the predicted amino acid sequence of mTCC#1
SEQ ID NO:142 is the predicted amino acid sequence of mTCC#2
SEQ ID NO:143 is the amino acid sequence of MTb9.8
SEQ ID NO:144 is the amino acid sequence of Tb#470
SEQ ID NO:145 is the full length nucleotide sequence of mTTC#3
SEQ ID NO:146 is the predicted amino acid sequence of mTTC#3
SEQ ID NO:147 and 148 are the sequences of primers used to amplify the full-length coding sequence of mTTC#3
SEQ ID NO:149 is the 5' nucleotide sequence of P1
SEQ ID NO:150 is the nucleotide sequence of P2
SEQ ID NO:151 is the 3' nucleotide sequence of P3
SEQ ID NO:152 is the nucleotide sequence of P4
SEQ ID NO:153 is the nucleotide sequence of P6
SEQ ID NO:154 is the nucleotide sequence of P7
SEQ ID NO:155 is the nucleotide sequence of P8
SEQ ID NO:156 is the nucleotide sequence of P9
SEQ ID NO:157 is the 5' nucleotide sequence of P10
SEQ ID NO:158 is the 5' nucleotide sequence of P11
SEQ ID NO:159 is the 3' nucleotide sequence of P12
SEQ ID NO:160 is the full length nucleotide sequence of MO-1
SEQ ID NO:161 is the full length amino acid sequence of MO-1.
SEQ ID NO:162 is the full length nucleotide sequence of MO-2
SEQ ID NO:163 is the full length amino acid sequence of MO-2
SEQ ID NO:164 is the full length nucleotide sequence of TbH4/XP-1 (MTB48).

DESCRIPTION OF THE SPECIFIC EMBODIMENTS

I. Introduction

As noted above, the present invention is generally directed to compositions and methods for preventing, treating and diagnosing tuberculosis. In particular, the present invention relates to *Mycobacterium* antigens, optionally from a species such as *M. tuberculosis, M. bovis, M. smegmatis, BCG, M. leprae, M. scrofulaceum, M. avium-intracellulare, M. marinum, M. ulcerans, M. kansasii, M. xenopi, M. szulgai, M. fortuium,* or *M. chelonei*. In particular, the invention relates to *Mycobacterium* polypeptides and immunogenic fragments thereof, polynucleotides that encode the polypeptides and immunogenic fragments thereof, and methods of using such compositions in the treatment, prevention and diagnosis of *Mycobacterium* infection. In one embodiment of the invention, the polypeptides of the invention are used to diagnose tuberculosis. In another embodiment of the invention, the polypeptides of the invention are used to induce an immune response in a patient in order to prevent *Mycobacterium* infection, and in particular tuberculosis, or to reduce the probability of pathological responses typical of *Mycobacterium* infection, and in particular tuberculosis, in a patient. In another embodiment of the invention, the polynucleotides of the invention are used to produce DNA vaccines, or for diagnostic purposes.

II. Definitions

"Nucleic acid" refers to deoxyribonucleotides or ribonucleotides and polymers thereof in either single- or doublestranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The term also encompasses ribonucleotides including HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Unless otherwise indicated, a particular nucleic acid sequence also implicitly encompasses conservatively modified variants thereof (e.g., degenerate codon substitutions) and complementary sequences, as well as the sequence explicitly indicated. Polynucleotide variants may contain one or more substitutions, additions, deletions and/or insertions, as further described below, preferably such that the immunogenicity of the encoded polypeptide is not diminished relative to the native polypeptide. The effect on the immunogenicity of the encoded polypeptide may generally be assessed as described herein. The term "variants" also encompasses interspecies homologs. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds. Thus, for instance, a polypeptide comprising an immunogenic portion of an antigen may consist entirely of the immunogenic portion, or may contain additional sequences. The additional sequences may be derived from the native *Mycobacterium* antigen or may be heterologous, and such sequences may (but need not) be immunogenic.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The compositions and methods of this invention also encompass variants of the above polypeptides. A polypeptide "variant," as used herein, is a polypeptide that differs from the recited polypeptide only in conservative substitutions and/or modifications, such that the therapeutic and/or immunogenic properties of the polypeptide are retained. Polypeptide variants preferably exhibit at least about 70%, more preferably at least about 90% and most preferably at least about 95% identity to the identified polypeptides. For polypeptides with immunoreactive properties, variants may, alternatively, be identified by modifying the amino acid sequence of one of the above polypeptides, and evaluating the immunoreactivity of the modified polypeptide. For polypeptides useful for the generation of diagnostic binding agents, a variant may be identified by evaluating a modified polypeptide for the ability to generate antibodies that detect the presence or absence of *Mycobacterium* infection, and in particular tuberculosis. Alternatively, variants of the claimed antigens that may be usefully employed in the inventive diagnostic methods may be identified by evaluating modified polypeptides for their ability to detect antibodies present in the sera of *Mycobacterium*-infected patients. Such modified sequences may be prepared and tested using, for example, the representative procedures described herein.

A "conservative substitution" applies to both amino acid and nucleic acid sequences. With respect to particular nucleic acid sequences, conservative substitutions refers to changes in the nucleic acid sequence that result in nucleic acids encoding identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservative substitution" where the alteration results in the substitution of an amino acid with a chemically similar amino acid and where the alteration has minimal influence on the immunogenic properties, secondary structure and hydropathic nature of the polypeptide. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

"Immunogenic," as used herein, refers to the ability to elicit an immune response (e.g., cellular or humoral) in a patient, such as a human, and/or in a biological sample (in vitro). In particular, antigens that are immunogenic (and immunogenic portions or other variants of such antigens) are recognized by a B-cell and/or a T-cell surface antigen receptor. Antigens that are immunogenic (and immunogenic portions or other variants of such antigens) are capable of stimulating cell proliferation, interleukin-12 production and/or interferon-γ production in biological samples comprising one or more cells selected from the group of T cells, NK cells, B cells and macrophages, where the cells are derived from an *Mycobacterium*-immune individual. Polypeptides comprising at least an immunogenic portion of one or more *Mycobacterium* antigens may generally be used to detect tuberculosis or to induce protective immunity against tuberculosis in a patient.

"Fusion polypeptide" or "fusion protein" refers to a protein having at least two heterologous polypeptides covalently linked, preferably *Mycobacterium* sp. polypeptides, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, subsequences, and interspecies homologs of the antigens that make up the fusion protein. *Mycobacterium tuberculosis* antigens are described in Cole et al., *Nature* 393:537 (1998). The complete sequence of the *Mycobacterium tuberculosis* genome can be found at http://www.sanger.ac.uk and at http://www.pasteur.fr/mycdb/ (MycDB).

An adjuvant refers to the components in a vaccine or therapeutic composition that increase the specific immune response to the antigen (see, e.g., Edelman, *AIDS Res. Hum Retroviruses* 8:1409–1411 (1992)). Adjuvants induce immune responses of the Th1-type and Th-2 type response. Th1-type cytokines (e.g., IFN-γ, IL-2, and IL-12) tend to favor the induction of cell-mediated immune response to an administered antigen, while Th-2 type cytokines (e.g., IL-4, IL-5, Il-6, IL-10 and TNF-β) tend to favor the induction of humoral immune responses.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For stringent hybridization, a positive signal is at least two times background, preferably 10 times background hybridization. Exemplary stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately" stringent hybridization conditions include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "identical" or percent "identity," in the context of two or more nucleic acids or polypeptide sequences, refer to two or more sequences or subsequences that are the same or have a specified percentage of amino acid residues or nucleotides that are the same (i.e., 55%, 60%, 65%, 70%, 75%, or 80% identity, preferably 85%, 90%, 95%, 96%, 97%, 98%, 99% or higher identity over a specified window region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, *A model of evolutionary change in proteins—Matrices for detecting distant relationships, In*: Dayhoff (ed.) *Atlas of Protein Sequence and Structure*, National Biomedical Research Foundation, Washington D.C. Vol. 5, Suppl. 3, pp. 345–358 (1978); Hein, *Unified Approach to Alignment and Phylogenes* pp. 626–645 *Methods in Enzymology* vol. 183, Academic Press, Inc., San Diego, Calif. (1990); Higgins and Sharp, *CABIOS* 5:151–153 (1989); Myers and Muller, *CABIOS* 4:11–17 (1988); Robinson, *Comb. Theor* 11:105 (1971); Santou and Nes, *Mol. Biol. Evol.* 4:406–425 (1987); Sneath and Sokal, *Numerical Taxonomy—the Principles and Practice of Numerical Taxonomy*, Freeman Press, San Francisco, Calif. (1973); Wilbur and Lipman, *Proc. Natl. Acad. Sci. USA* 80:726–730 (1983).

Alternatively, optimal alignment of sequences for comparison can be conducted, e.g., by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. (1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see, e.g., *Fundamental Immunology* (Paul ed., 3d ed. (1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990))

As used herein, an antibody, or antigen-binding fragment thereof, is said to "specifically bind" to a polypeptide of interest if it reacts at a detectable level (within, for example, an ELISA) with the polypeptide of interest, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ l/mol. The binding constant may be determined using methods well known in the art.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply.

In the context of the present invention, a "patient" refers to any warm-blooded animal, preferably a human. A patient may be afflicted with a disease, or may be free of detectable disease and/or infection.

III. Preparation of *Mycobacterium* Polypeptides and Nucleic Acids

In general, *Mycobacterium* antigens and DNA sequences encoding such antigens may be prepared using any of a variety of procedures. Here and throughout the specification, the *Mycobacterium* antigens are preferably *M. tuberculosis* antigens.

A. Polynucleotides of the Invention

DNA sequences encoding antigens may be identified, for example, by screening an appropriate *Mycobacterium* genomic or cDNA expression library with sera obtained from patients infected with *Mycobacterium*. Alternatively, sera from mice immunized with *Mycobacterium* antigens can be used. In some embodiments, sera is obtained from mice immunized with blood or urine from syngeneic mice infected with *Mycobacterium*. Such screens may generally be performed using techniques well known to those of ordinary skill in the art, such as those described in Sambrook et al., *Molecular Cloning: A Laboratory Manual*, Cold Spring Harbor Laboratories, Cold Spring Harbor, N.Y. (1989).

DNA sequences encoding the antigens of the present invention may also be obtained by screening an appropriate Mycobacterium cDNA or genomic DNA library for DNA sequences that hybridize to degenerate oligonucleotides derived from partial amino acid sequences of isolated antigens. Degenerate oligonucleotide sequences for use in such a screen may be designed and synthesized, and the screen may be performed as described, for example, in Sambrook et al., supra, and references cited therein.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., supra). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Amplification techniques may also be employed, using the above oligonucleotides in methods well known in the art, to isolate a nucleic acid probe from a cDNA or genomic library. The library screen for obtaining a full length coding sequence from a partial cDNA sequence may then be performed using the isolated probe. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a poly A region or vector sequence, to identify sequences that are 5' and 3' of a known sequence. Optionally, capture PCR (Lagerstrom et al., *PCR Methods Applic.* 1:111–119 (1991)) and walking PCR (Parker et al., *Nuci. Acids. Res.* 19:3055–60 (1991)) can also be used. Methods for amplification further include the ligase chain reaction (LCR; see, e.g., EP patent application publication 320, 308), the Qbeta Replicase method (see, e.g., PCT/US87/00880), the isothermal amplification method, the Strand Displacement Amplification (SDA), the cyclic probe reaction (CPR), the transcription-based amplification systems (TAS; see, e.g., PCT/US88/10315), as well as other methods known to those of skill in the art (see, e.g., GB patent application No. 2,202,328; PCT/US89/01025;

and EP patent application publication No. 329,822). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183 (1983)). Alternatively, RNA molecules may be generated by in vitro or in vivo transcription of DNA sequences encoding a Mycobacterium polypeptide, or portion thereof, provided that the DNA is incorporated into a vector with a suitable RNA polymerase promoter (such as T7 or SP6). Certain portions may be used to prepare an encoded polypeptide, as described infra. In addition, or alternatively, a portion may be administered to a patient such that the encoded polypeptide is generated in vivo (e.g., by transfecting antigen-presenting cells, such as dendritic cells, with a cDNA construct encoding a *Mycobacterium* polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells or tissues to facilitate the production of antisense RNA. An antisense polynucleotide may be used, as described herein, to inhibit expression of a *Mycobacterium* protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co., Mt. Kisco, N.Y. (1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence or of a complementary sequence may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described infra. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). The polynucleotides may also be administered as naked plasmid vectors. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

B. Polypeptides of the Invention

Within the context of the present invention, polypeptides may comprise at least an immunogenic portion of a *Mycobacterium* antigen, or a variant thereof, as described herein. As noted above, a *Mycobacterium* antigen is a protein that is expressed by cells infected with *Mycobacterium*. In a preferred embodiment the *Mycobacterium* antigen is a *Mycobacterium tuberculosis* antigen. Proteins that are *Mycobacterium* antigens also react detectably within an immunoassay (such as an ELISA) with antisera from a patient infected with *Mycobacterium*, and preferably with *M. tuberculosis*. Polypeptides as described herein may be of any length. Additional sequences derived from the native protein and/or heterologous sequences may be present, and such sequences may (but need not) possess further immunogenic or antigenic properties.

Genomic or cDNA libraries derived from *Mycobacterium*, and preferably from *M. tuberculosis*, may be screened directly using peripheral blood mononuclear cells (PBMCs) or T cell lines or clones derived from one or more *Mycobacterium*-immune individuals. In a preferred embodiment, the *Mycobacterium*-immune individuals are *M. tuberculosis*-immune individuals. Direct library screens may generally be performed by assaying pools of expressed recombinant proteins for the ability to induce proliferation and/or interferon-γ production in T cells derived from a *Mycobacterium*-immune individual. Potential T cell antigens may be first selected based on antibody reactivity, as described above. Purified antigens are then evaluated for their ability to elicit an appropriate immune response (e.g., cellular) using, for example, the representative methods described infra. Immunogenic antigens may then be partially sequenced using techniques such as traditional Edman chemistry (see Edman and Berg, *Eur. J. Biochem.* 80:116–132 (1967)).

Immunogenic antigens may also be produced recombinantly using a DNA sequence that encodes the antigen, which has been inserted into an appropriate expression vector, i.e., a vector which contains the necessary elements for the transcription and translation of the inserted coding sequence, and expressed in an appropriate host. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., supra; and Ausubel et al., supra.

Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Portions and other variants of *Mycobacterium* antigens may be generated by synthetic or recombinant means. Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain (see Merrifield, *J. Am. Chem. Soc.* 85:2149–2146 (1963)). Equipment for automated synthesis of polypeptides is commercially available from suppliers such as Perkin Elmer/Applied BioSystems Division, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides of the present invention. Expression may be achieved in any appropriate host cell (e.g., prokaryotic, yeast and higher eukaryotic cell) that has been transformed or transfected with an expression vector containing a DNA molecule that encodes a recombinant polypeptide. Suitable expression vector/host systems include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV); tobacco mosaic virus (TMV)) or with bacterial expression vectors (e.g., Ti or pBR322 plasmids); or animal cell systems. Examples of expression vectors for use in bacterial systems include, e.g., multifunctional *E. coli* cloning and expression vectors such as BLUESCRIPT (Stratagene) and pIN vectors (see Van Heeke and Schuster, *J. Biol. Chem.* 264:5503–5509 (1989)). In the yeast, *Saccharomyces cerevisiae*, a number of vectors containing constitutive or inducible promoters such as alpha factor, alcohol oxidase, and PGH may be used (see, e.g., Ausubel et al., supra; and Grant et al., *Methods Enzymol.* 153:516–544 (1987)). In cases where plant expression vectors are used, the expression of sequences encoding polypeptides may be driven by any of a number of promoters, including, but not limited to, the 35S and 19S promoters of CaMV, the omega leader sequence from TMV (Takamatsu, *EMBO J.* 6:307–311 (1987)), as well as plant promoters such as the small subunit of RUBISCO or heat-shock promoters (Coruzzi et al., *EMBO J.* 3:1671–1680 (1984); Broglie et al., *Science* 224: 838–843 (1984); and Winter et al., *Results Probl. Cell Differ.* 17:85–105 (1991)). A variety of expression vectors are also available for expression in insect systems. For example, suitable vectors for expression in *Spodoptera frugiperda* cells or in *Trichoplusia* include, but are not limited to, the *Autographa californica* nuclear polyhedrosis virus (AcNPV). Furthermore, viral-based expression systems can also be used to express the polypeptide(s) of interest in mammalian host cells. Preferably, the host cells employed are *E. coli*, yeast or mammalian cell lines, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. For use in the methods described herein, however, such substantially pure polypeptides may be combined.

In one embodiment, the subject invention discloses polypeptides comprising at least an immunogenic portion of a *M. tuberculosis* antigen (or a variant of such an antigen) that comprises the amino acid sequences encoded by (a) the DNA sequence of SEQ ID NO:145, 149, 150, 151, 152, 153, 154, 155, 156, 157, 158, 159, 160, 162, and 164; (b) the complement of such DNA sequence, or (c) a DNA sequence substantially homologous to the sequence of (a) or (b). In a related embodiment, the present invention provides polypeptides comprising at least an immunogenic portion of a *M. tuberculosis* antigen having the amino acid sequence provided in SEQ ID NO:146, 161, or 163, and variants thereof.

The *Mycobacterium* antigens provided herein include variants that are encoded by DNA sequences which are substantially homologous to one or more of DNA sequences specifically recited herein.

C. Fusion Polypeptides

In one embodiment, the present invention provides fusion proteins comprising multiple polypeptides of the invention or, alternatively, a polypeptide of the present invention and a known *Mycobacterium* antigen, preferably a *M. tuberculosis* antigen. Examples of such known *Mycobacterium* antigens include, but are not limited to, e.g., 38 kD antigen described in Andersen and Hansen, *Infect. Immun.* 57:2481–2488 (1989) (Genbank Accession No. M30046) and ESAT-6 previously identified in *M. bovis* (Accession No. U34848) and in *M. tuberculosis* (Sorensen et al., *Infec. Immun.* 63:1710–1717 (1995). Examples of suitable *Mycobacterium* antigens are disclosed in U.S. Pat. Nos. 6,350, 456, 6,544,522, and 6,627,199, and in U.S. provisional patent application Nos. 60/158,338 and 60/158,425, herein each incorporated by reference. Variants of such fusion proteins are also provided.

The fusion proteins of the present invention may also include a fusion partner which may, for example, assist in providing T helper epitopes (an immunological fusion partner), preferably T helper epitopes recognized by humans, or assist in expressing the protein (an expression enhancer) at higher yields than the native recombinant protein. Certain preferred fusion partners are both immunological and expression enhancing fusion partners. Examples of such proteins include tetanus, tuberculosis and hepatitis proteins (see, e.g., Stoute et al., *New Engl. J. Med.* 336:86–91, 1997). Other fusion partners may be selected so as to increase the solubility of the protein or to enable the protein to be targeted to desired intracellular compartments. Still further fuision partners include affinity tags, which facilitate purification of the protein.

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner are included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798 (1992)). Within a preferred embodiment, a repeat portion of LYTA may be incorporated into a fusion protein. A repeat portion is found in the C-terminal region starting at residue 178. A particularly preferred repeat portion incorporates residues 188–305.

The fusion proteins of the present invention may also include a linker peptide between the first and second polypeptides. A peptide linker sequence may be employed to separate, for example, the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46 (1985); Murphy et al., *Proc. Natl. Acad. Sci. USA* 83:8258–8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Fusion proteins may generally be prepared using standard techniques, including chemical conjugation. Preferably, a fusion protein is expressed as a recombinant protein in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

The ligated DNA sequences are operably linked to suitable transcriptional or translational regulatory elements. The regulatory elements responsible for expression of DNA are located only 5' to the DNA sequence encoding the first polypeptide. Similarly, stop codons required to end translation and transcription termination signals are only present 3' to the DNA sequence encoding the second polypeptide.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

D. Immunogenicity of the Polypeptides of the Invention

Regardless of the method of preparation, the antigens and immunogenic portions thereof described herein have the ability to induce an immunogenic response. More specifically, the antigens have the ability to react with sera obtained from a *Mycobacterium*-infected individual and/or to induce proliferation and/or cytokine production (i.e., interferon-γ and/or interleukin-12 production) in T cells, NK cells, B cells and/or macrophages derived from a *Mycobacterium*-immune individual. Here and throughout the specification, the *Mycobacterium*-immune individual is preferably an *M. tuberculosis*-immune individual.

Reactivity with sera obtained from a *Mycobacterium*-infected individual may be evaluated using, for example, the representative ELISA assays described herein, where an absorbance reading with sera from infected individuals that is at least three standard deviations above the absorbance obtained with sera from uninfected individuals is considered positive.

The selection of cell type for use in evaluating an immunogenic response to a antigen will, of course, depend on the desired response. For example, interleukin-12 production is most readily evaluated using preparations containing B cells and/or macrophages. A *Mycobacterium*-immune individual (e.g., an *M. tuberculosis*-immune individual) is one who is considered to be resistant to the development of the disease (e.g., tuberculosis) by virtue of having mounted an effective T cell response to *Mycobacterium* (i.e., substantially free of disease symptoms). Such individuals may be identified based on a strongly positive (i.e., greater than about 10 mm diameter induration) intradermal skin test response to tuberculosis proteins (PPD) and an absence of any signs or symptoms of, e.g., tuberculosis disease. T cells, NK cells, B cells and macrophages derived from *Mycobacterium*-immune individuals may be prepared using methods known to those of ordinary skill in the art. For example, a preparation of PBMCs (i.e., peripheral blood mononuclear cells) may be employed without further separation of component cells. PBMCs may generally be prepared, for example, using density centrifugation through Ficoll™ (Winthrop Laboratories. NY).

T cells for use in the assays described herein may also be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from *Mycobacterium*-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods known to those of ordinary skill in the art, to more accurately define individual T cell specificity. In general, antigens that test positive in assays for proliferation and/or cytokine production (i.e., interferon-γ and/or interleukin-12 production) performed using T cells, NK cells, B cells and/or macrophages derived from an *Mycobacterium*-immune individual are considered immunogenic. Such assays may be performed, for example, using the representative procedures described infra. Immunogenic portions of such antigens may be identified using similar assays, and may be present within the polypeptides described herein.

The ability of a polypeptide (e.g., an immunogenic antigen, or a portion or other variant thereof) to induce cell proliferation is evaluated by contacting the cells (e.g., T cells and/or NK cells) with the polypeptide and measuring the proliferation of the cells. In general, the amount of polypeptide that is sufficient for evaluation of about $10^5$ cells ranges from about 10 ng/ml to about 100 μg/ml and preferably is about 10 μg/ml. The incubation of a polypeptide with cells is typically performed at 37° C. for about six days. Following incubation with the polypeptide, the cells are assayed for a proliferative response, which may be evaluated by methods known to those of ordinary skill in the art, such as exposing the cells to a pulse of radiolabeled thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

The ability of a polypeptide to stimulate the production of interferon-γ and/or interleukin-12 in cells may be evaluated by contacting the cells with the polypeptide and measuring the level of interferon-γ or interleukin-12 produced by the cells. In general, the amount of polypeptide that is sufficient for the evaluation of about $10^5$ cells ranges from about 10 ng/ml to about 100 μg/ml and preferably is about 10 μg/ml. The polypeptide may, but need not, be immobilized on a solid support, such as a bead or a biodegradable microsphere, such as those described in, e.g., U.S. Pat. Nos. 4,897,268 and 5,075,109. The incubation of a polypeptide with the cells is typically performed at 37° C. for about six days. Following incubation with the polypeptide, the cells are assayed for interferon-γ and/or interleukin-12 (or one or more subunits thereof) production, which may be evaluated by methods known to those of ordinary skill in the art, such as an enzyme-linked immunosorbent assay (ELISA) or, in the case of the IL-12 P70 heterodimer, a bioassay such as an assay measuring proliferation of T cells. In general, a polypeptide that results in the production of at least 50 pg of interferon-γ per ml of cultured supernatant (containing $10^{4-10}5$ T cells per ml) is considered able to stimulate the production of interferon-γ. A polypeptide that stimulates the production of at least 10 pg/ml of IL-12 P70 subunit, and/or at least 100 pg/ml of IL-12 P40 subunit, per $10^5$ macrophages or B cells (or per $3\times10^5$ PBMC) is considered able to stimulate the production of IL-12.

In general, immunogenic antigens are those antigens that stimulate proliferation and/or cytokine production (i.e., interferon-γ and/or interleukin-12 production) in T cells, NK cells, B cells and/or macrophages derived from at least about 25% of *Mycobacterium*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate proliferation and/or cytokine production in vitro in cells derived from more than about 25% of individuals that are not *Mycobacterium*-immune, thereby eliminating responses that are not specifically due to *Mycobacterium*-responsive cells. Those antigens that induce a response in a high percentage of T cell, NK cell, B cell and/or macrophage preparations from *Mycobacterium*-immune individuals (with a low incidence of responses in cell preparations from other individuals) have superior therapeutic properties.

Antigens with superior therapeutic properties may also be identified based on their ability to diminish the severity of *Mycobacterium* infection in experimental animals, when administered as a vaccine. Suitable vaccine preparations for use on experimental animals are described in detail below. Efficacy may be determined based on the ability of the antigen to provide at least about a 50% reduction in bacterial numbers and/or at least about a 40% decrease in mortality following experimental infection. Suitable experimental animals include, e.g., mice, guinea pigs and primates.

Antigens having superior diagnostic properties may generally be identified based on the ability to elicit a response in an intradermal skin test performed on an individual with active tuberculosis, but not in a test performed on an individual who is not infected with *Mycobacterium*. Skin tests may generally be performed as described below, with a response of at least 5 mm induration considered positive.

Immunogenic portions of *Mycobacterium* antigens may be prepared and identified using well known techniques, such as those summarized in Paul, *Fundamental Immunology*, 3d ed., Raven Press, pp. 243–247 (1993) and references cited therein. Such techniques include screening polypeptide portions of the native antigen for immunogenic properties and in particular, e.g., ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. The representative ELISAs as well as the proliferation and cytokine production assays described herein may generally be employed in these screens. An immunogenic portion of a polypeptide is a portion that, within such representative assays, generates a signal or an immune response (e.g., proliferation, interferon-γ production and/or interleukin-12 production) that is not substantially less than that generated by the full length polypeptide. In other words, an immunogenic portion of a *Mycobacterium* antigen generates at least about 20%, and preferably about 100%, of the signal and/or immune response induced by the full length antigen in the model ELISA or proliferation assay described herein, respectively. An immunogenic portion may also, or alternatively, stimulate the production of at least about 20%, and preferably about 100%, of the interferon-γ and/or interleukin-12 induced by the full length antigen in the model assay described herein. Such immunogenic portions may also react within such assays at a level that is greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory (1988). For use in the methods described herein, substantially pure polypeptides may be combined.

IV. Antibodies

The present invention further provides agents, such as antibodies and antigen-binding fragments thereof, that specifically bind to the polypeptides of the invention. Binding agents may be capable of differentiating between patients infected or not with *Mycobacterium*, and in particular with *M. tuberculosis*, using the representative assays provided infra. In other words, antibodies or other binding agents that bind to a *Mycobacterium* antigen will generate a signal indicating the presence of tuberculosis in at least about 20% of patients with the disease, and will generate a negative signal indicating the absence of the disease in at least about 90% of individuals without tuberculosis. To determine whether a binding agent satisfies this requirement, biological samples (e.g., blood, sera, urine, sputum, saliva, etc.) from patients with and without tuberculosis (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof.

Antibodies may be prepared by any of a variety of techniques known to those of ordinary skill in the art (see, e.g., Harlow and Lane, *Antibodies: A Laboratory Manual*, Cold Spring Harbor Laboratory (1988)). In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the immunogenic polypeptide is initially injected into any of a wide variety of mammals (e.g., mice, rats, rabbits, sheep and goats). In this step, the polypeptides of the invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Polyclonal antibodies raised to a fusion protein of the invention can also be obtained by selecting only those polyclonal antibodies that are specifically immunoreactive with the fusion protein of interest and not with the individual polypeptide components of the fusion protein. This selection may be achieved by subtracting out antibodies that cross-react with the individual polypeptide components of the fusion protein of interest.

Alternatively, antibodies that recognize each or all of the individual polypeptide components of a fusion protein may be useful in the context of the present invention.

Monoclonal antibodies specific for the immunogenic polypeptide of interest may be prepared, for example, using the technique of Kohier and Milstein, *Eur. J. Immunol.* 6:511–519 (1976), and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as, e.g., a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (see Harlow and Lane, *Antibodies: A Laboratory Manual*, Cold Spring Harbor Laboratory (1988)) and digested by papain to yield Fab and Fc fragments. The Fab and Fc fragments may be separated by affinity chromatography on protein A bead columns.

Antibodies may be used in diagnostic tests to detect the presence of *Mycobacterium* antigens using assays similar to those detailed infra and other techniques well known to those of skill in the art, thereby providing a methods for detecting *Mycobacterium* infection, and in particular tuberculosis, in a patient.

Monoclonal antibodies of the present invention may be coupled to one or more therapeutic agents. Suitable agents in this regard include, but are not limited to, drugs, toxins, and derivatives thereof. Preferred drugs include, e.g., penicillin, rifampin, isoniazid, pyrazinamide, ethambutol, streptomycin, etc. These drugs can be obtained from a natural source or be semisynthetic or synthetic compounds. Preferred toxins include ricin, abrin, *Diphtheria* toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, including, e.g., U.S. Pat. No. 4,671,958.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as, e.g., albumins (e.g., U.S. Pat. No. 4,507,234), peptides and polysaccharides such as, e.g., aminodextran (e.g., U.S. Pat. No. 4,699,784). A carrier may also bear an agent by noncovalent bonding or by encapsulation, such as within a liposome vesicle (e.g., U.S. Pat. Nos. 4,429,008 and 4,873,088).

A variety of routes of administration for the antibodies and immunoconjugates may be used. Typically, administration will be, e.g., intravenous, intramuscular, subcutaneous, intranasal, or buccal. It will be evident that the precise dose of the antibody/immunoconjugate will vary depending upon the antibody used, the antigen density in the cells, and the rate of clearance of the antibody.

V. T Cells

Immunotherapeutic compositions may also, or alternatively, comprise T cells specific for a *Mycobacterium* antigen. Such cells may generally be prepared in vitro or ex vivo, using standard procedures. For example, T cells may be isolated from bone marrow, peripheral blood or a fraction of bone marrow or peripheral blood of a patient, using a commercially available cell separation system, such as the CEPRATE™ system, available from CellPro Inc., Bothell Wash. (see also U.S. Pat. Nos. 5,240,856 and 5,215,926; WO 89/06280; WO 91/16116 and WO 92/07243). Alternatively, T cells may be derived from related or unrelated humans, non-human mammals, cell lines or cultures.

T cells may be stimulated with a *Mycobacterium* polypeptide, a polynucleotide encoding a *Mycobacterium* polypeptide and/or an antigen presenting cell (APC) that expresses such a polypeptide. Such stimulation is performed under conditions and for a time sufficient to permit the generation of T cells that are specific for the polypeptide. Preferably, a *Mycobacterium* polypeptide or polynucleotide is present within a delivery vehicle, such as a microsphere, to facilitate the generation of specific T cells.

T cells are considered to be specific for a *Mycobacterium* polypeptide if the T cells kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070 (1994). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a *Mycobacterium* polypeptide (100 ng/ml–100 µg/ml, preferably 200 ng/ml–25 µg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience, Greene (1998)). T cells that have been activated in response to a *Mycobacterium* polypeptide, polynucleotide or polypeptide-expressing APC may be $CD4^+$ and/or $CD8^+$. *Mycobacterium* polypeptide-specific T cells may be expanded using standard techniques. Within preferred embodiments, the T cells are derived from a patient, or from a related or unrelated donor, and are administered to the patient following stimulation and expansion.

For therapeutic purposes, $CD4^+$ or $CD8^+$ T cells that proliferate in response to a *Mycobacterium* polypeptide, polynucleotide or APC can be expanded in number either in vitro or in vivo. Proliferation of such T cells in vitro may be accomplished in a variety of ways. For example, the T cells can be re-exposed to a *Mycobacterium* polypeptide (e.g., a short peptide corresponding to an immunogenic portion of such a polypeptide) with or without the addition of T cell growth factors, such as interleukin-2, and/or stimulator cells that synthesize a *Mycobacterium* polypeptide. Alternatively, one or more T cells that proliferate in the presence of a *Mycobacterium* polypeptide can be expanded in number by cloning. Methods for cloning cells are well known in the art, and include limiting dilution. Following expansion, the cells may be administered back to the patient as described, for example, by Chang et al., *Crit. Rev. Oncol. Hematol.* 22:213 (1996).

VI. Diagnostic Assays

A. Diagnostic Assays with *Mycobacterium* Polypeptides

In another aspect, the present invention provides methods for using the polypeptides described above to diagnose *Mycobacterium* infection, and in particular tuberculosis. In this aspect, methods are provided for detecting *Mycobacterium* infection in a biological sample, using one or more of the above polypeptides, alone or in combination. In embodiments in which multiple polypeptides are employed, polypeptides other than those specifically described herein, such as the 38 kD antigen described above, may be included. The polypeptide(s) are used in an assay, as described infra, to determine the presence or absence of antibodies to the polypeptide(s) in a biological sample (e.g., whole blood, sputum, serum, plasma, saliva, cerebrospinal fluid, urine, etc.) relative to a predetermined cut-off value. The presence of such antibodies indicates previous sensitization to mycobacterial antigens which may be indicative of *Mycobacterium* infection, and in particular tuberculosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *Mycobacterium*. After determining which samples test positive (as described below) with each polypeptide, combinations of two or more polypeptides may be formulated that are capable of detecting infection in most, or all, of the samples tested. Such polypeptides are complementary. For example, approximately 25–30% of sera from tuberculosis-infected individuals are negative for antibodies to any single protein, such as the above-mentioned 38 kD antigen. Complementary polypeptides may, therefore, be used in combination with the 38 kD antigen to improve sensitivity of a diagnostic test.

There are a variety of assay formats known to those of ordinary skill in the art for using one or more polypeptides to detect antibodies in a sample. See, e.g., Harlow and Lane, *Antibodies: A Laboratory Manual*, Cold Spring Harbor Laboratory (1988), which is incorporated herein by reference. In general, the presence or absence of tuberculosis in a patient may be determined by (a) contacting a biological sample obtained from a patient with one or more polypeptides or fusion proteins of the invention; (b) detecting in the sample a level of antibody that binds to the polypeptide(s) or the fusion protein(s); and (c) comparing the level of antibody with a predetermined cut-off value.

In a preferred embodiment, the assay involves the use of a polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide of interest is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art, which are amply described in the patent and scientific literature. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 µg, and preferably about 100 ng, is sufficient to bind an adequate amount of antigen.

Covalent attachment of the polypeptide of interest to a solid support may generally be achieved by first reacting the support with a bifunctional reagent that reacts with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, at A12–A13 (1991)).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies present within the sample that recognize the polypeptide of interest are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or TWEEN 20™ (Sigma Chemical Co., St. Louis, Mo.), may be employed. The immobilized polypeptide is then incubated with the sample, and the antibody is allowed to bind to the antigen. The sample may be diluted with a suitable diluent, such as phosphate-buffered saline (PBS) prior to incubation. In general, an appropriate contact time (i.e., incubation time) is a period of time that is sufficient to detect the presence of antibody within a *Mycobacterium*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% TWEEN 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of a binding agent to the reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*Mycobacterium* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for *Mycobacterium* infection. In another embodiment, the cut-off value is determined using a Receiver Operator Curve, according to the method of Sackett et al., *Clinical Epidemiology: A Basic Science for Clinical Medicine*, Little Brown and Co., pp. 106–107 (1985). Briefly, in this embodiment, the cut-off value may be determined from a plot of pairs of true positive rates (i.e., sensitivity) and false positive rates (100% specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for tuberculosis.

In a related embodiment, the assay is performed in a rapid flow-through or strip test format, wherein the antigen is immobilized on a membrane, such as, e.g., nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which the polypeptide is bound is immersed in a solution containing the sample. The sample migrates along the membrane through a region containing the detection reagent and to the area of immobilized polypeptide. The concentration of the detection reagent at the polypeptide indicates the presence of anti-*Mycobacterium* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed supra. Preferably, the amount of polypeptide immobilized on the membrane ranges from about 25 ng to about 1 µg, and more preferably from about 50 ng to about 500 ng. Such tests can typically be performed with a very small amount (e.g., one drop) of patient serum or blood.

In another aspect, this invention provides methods for using one or more of the polypeptides described above to diagnose *Mycobacterium* infection, and in particular tuberculosis, using a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 ml syringe. Preferably, the reaction is measured at least 48 hours after injection, more preferably 48–72 hours.

The DTH reaction is a cell-mediated immune response which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of *Mycobacterium* infection, which may or may not be manifested as an active disease.

The polypeptides of this invention are preferably formulated, for use in a skin test, as pharmaceutical compositions containing a polypeptide and a physiologically acceptable carrier, as described infra. Such compositions typically contain one or more of the above polypeptides in an amount ranging from about 1 μg to about 100 μg, preferably from about 10 μg to about 50 μg in a volume of 0.1 ml. Preferably, the carrier employed in such pharmaceutical compositions is a saline solution with appropriate preservatives, such as phenol and/or TWEEN 80™.

In a preferred embodiment, a polypeptide employed in a skin test is of sufficient size such that it remains at the site of injection for the duration of the reaction period. In general, a polypeptide that is at least 9 amino acids in length is sufficient. The polypeptide is also preferably broken down by macrophages within hours of injection to allow presentation to T-cells. Such polypeptides may contain repeats of one or more of the above sequences and/or other immunogenic or non-immunogenic sequences.

Of course, numerous other assay protocols exist that are suitable for use with the polypeptides of the present invention. The above descriptions are intended to be exemplary only.

B. Diagnostic Assays with Polynucleotides Encoding *Mycobacterium* Polypeptides

Antibodies may be used in diagnostic tests to detect the presence of *Mycobacterium* antigens using assays similar to those detailed above and other techniques well known to those of skill in the art, thereby providing a method for detecting *Mycobacterium* infection, and in particular tuberculosis, in a patient.

Diagnostic reagents of the present invention may also comprise DNA sequences encoding one or more of the above polypeptides, or one or more portions thereof. Alternatively, *Mycobacterium* infection can be detected based on the level of mRNA encoding a *Mycobacterium* antigen in a biological sample. For example, at least two oligonucleotide primers may be employed in a polymerase chain reaction (PCR) based assay to amplify *Mycobacterium*-specific cDNA derived from a biological sample, wherein at least one of the oligonucleotide primers is specific for (i.e., hybridizes to) a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of a polypeptide of the invention in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a *Mycobacterium* antigen that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having the sequence of SEQ ID NO:145, 149, 150, 151, 152, 153, 154, 155, 156, 157, 158, 159, 160, 162, and 164. Primers or probes may thus be used to detect Mycobacterium-specific sequences in biological samples. DNA probes or primers comprising oligonucleotide sequences described above may be used alone, in combination with each other, or with previously identified sequences, such as the 38 kD antigen discussed above.

Techniques for both PCR based assays and hybridization assays are well known in the art (see, for example, Mullis et al., *Cold Spring Harbor Symp. Quant. Biol.*, 51:263 (1987); Erlich ed., *PCR Technology*, Stockton Press, N.Y. (1989)).

One preferred assay employs RT-PCR, in which PCR is applied in conjunction with reverse transcription. Typically, RNA is extracted from a biological sample and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with *Mycobacterium* infection. The amplification reaction may be performed on several dilutions of cDNA spanning two orders of magnitude. A two-fold or greater increase in expression in several dilutions of the test patient sample as compared to the same dilutions of the non-infected sample is typically considered positive.

C. Diagnostic Assays Using the Detection of T Cells

A *Mycobacterium* infection may also, or alternatively, be detected based on the presence of T cells that specifically react with a *Mycobacterium* protein in a biological sample. Within certain methods, a biological sample comprising $CD4^+$ and/or $CD8^+$ T cells isolated from a patient is incubated with a *Mycobacterium* polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with a *Mycobacterium* polypeptide of the invention (at a concentration of, e.g., 5–25 μg/ml). It may be desirable to incubate another aliquot of a T cell sample in the absence of the *Mycobacterium* polypeptide to serve as a control. For CD4+ T cells, activation is preferably detected by evaluating proliferation of the T cells. For CD8+ T cells, activation is preferably detected by evaluating cytolytic activity. A level of proliferation that is at least two fold greater and/or a level of cytolytic activity that is at least 20% greater than in disease-free patients indicates the presence of a *Mycobacterium* infection in the patient.

D. Diagnostic Assays for Monitoring the Progression of the Infection

In another embodiment, *Mycobacterium* proteins and polynucleotides encoding such proteins may be used as markers for monitoring the progression of a *Mycobacterium* infection. In this embodiment, assays as described above for the diagnosis of a *Mycobacterium* infection may be performed over time, and the change in the level of reactive polypeptide(s) evaluated. For example, the assays may be performed every 24–72 hours for a period of 1 month to 6–12 months, and thereafter performed as needed. In general, the *Mycobacterium* infection is progressing in those patients in whom the level of polypeptide detected by the binding agent increases over time. In contrast, the *Mycobacterium* infection is not progressing when the level of reactive polypeptide either remains constant or decreases with time.

As noted above, to improve sensitivity, multiple *Mycobacterium* markers may be assayed within a given sample. It will be apparent that binding agents specific for different proteins provided herein may be combined within a single assay. Further, multiple primers or probes may be used concurrently. The selection of *Mycobacterium* protein markers may be based on routine experiments to determine combinations that result in optimal sensitivity.

VII. Therapeutic Applications

In another aspect, the present invention provides methods for using one or more of the above polypeptides or fusion proteins (or DNA molecules encoding such polypeptides) to induce protective immunity against *Mycobacterium* infection in a patient to either prevent or treat *Mycobacterium* infection, and in particular tuberculosis.

A. Pharmaceutical Compositions

In additional embodiments, the present invention concerns formulation of the polypeptides, fusion proteins or DNA molecules disclosed herein in pharmaceutically-acceptable solutions for administration to a cell or an animal, either alone, or in combination with one or more other modalities of therapy. The pharmaceutical compositions of the invention may comprise one or more polypeptides, each of which may contain one or more of the above sequences (or variants thereof), and a physiologically acceptable carrier.

It will also be understood that, if desired, the polypeptide, fusion protein and nucleic acid molecule compositions disclosed herein may be administered in combination with other agents as well, such as, e.g., other proteins or polypeptides or various pharmaceutically-active agents. In particular, such pharmaceutical compositions may also contain other *Mycobacterium* antigens, either incorporated into a combination polypeptide or present within a separate polypeptide. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Oral Administration

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, e.g., Mathiowitz et al., *Nature* 386:410–414 (1997); Hwang et al., *Crit Rev Ther Drug Carrier Syst.* 15:243–84 (1998); U.S. Pat. Nos. 5,641,515; 5,580,579; and 5,792,451). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in, e.g., U.S. Pat. Nos. 5,543,158; 5,641,515; and 5,399,363. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington *Pharmaceutical Sciences* 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212. Likewise, the delivery of drugs using intranasal microparticle resins (Takenaga et al., *J Controlled Release* 52:81–87 (1998)) and lysophosphatidyl-glycerol compounds (see, e.g., U.S. Pat. No. 5,725,871) are also well-known in the pharmaceutical arts. Likewise, transmucosal drug delivery in the form of a polytetrafluoroetheylene support matrix is described in U.S. Pat. No. 5,780,045.

4. Liposome-, Nanocapsule-, and Microparticle-mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the polypeptides, fusion proteins and nucleic acids disclosed herein. The formation and use of liposomes is generally known to those of skill in the art (see, e.g., Couvreur et al., *FEBS Lett.* 84(2):323–326 (1977); Couvreur (1988); Lasic, *Trends Biotechnol.* 16(7):307–321 (1998); which describes the use of liposomes and nanocapsules in the targeted antibiotic therapy for intracellular bacterial infections and diseases). Recently, liposomes were developed with improved serum stability and circulation half-times (Gabizon and Papahadjopoulos, *Proc Natl Acad Sci U S A.* 85(18):6949–6953 (1988); Allen and Choun (1987); U.S. Pat. No. 5,741,516). Further, various methods of liposome and liposome like preparations as potential drug carriers have been reviewed (Takakura, *Nippon Rinsho* 56(3):691–695 (1998); Chandran et al., *Indian J Exp Biol.* 35(8):801–809 (1997); Margalit, *Crit Rev Ther Drug Carrier Syst.* 12(2–3):233–261 (1995); U.S. Pat. Nos. 5,567,434; 5,552,157; 5,565,213; 5,738,868; and 5,795,587).

Liposomes have been used successfully with a number of cell types that are normally resistant to transfection by other procedures including T cell suspensions, primary hepatocyte cultures and PC 12 cells (Renneisen et al., *J Biol Chem.* 265(27):16337–16342 (1990); Muller et al., *DNA Cell Biol.* 9(3):221–229 (1990)). addition, liposomes are free of the DNA length constraints that are typical of viral-based delivery systems. Liposomes have been used effectively to introduce genes, drugs (Heath and Martin, *Chem Phys Lipids* 40(2–4):347–358 (1986); Heath et al., *Biochim Biophys Acta.* 862(1):72–80 (1986); Balazsovits et al., *Cancer Chemother Pharmacol.* 23(2):81–6. (1989); Fresta and Puglisi, *J. Drug Target* 4(2):95–101 (1996)), radiotherapeutic agents (Pikul et al., *Arch Surg.* 122(12):1417–1420 (1987)), enzymes (Imaizumi et al., *Stroke* 21(9):1312–1317 (1990); Imaizumi et al., *Acta Neurochir Suppl (Wien)* 51:236–238 (1990)), viruses (Faller and Baltimore, *J Virol.* 49(1):269–272 (1984)), transcription factors and allosteric effectors (Nicolau and Gersonde, *Naturwissenschaften* 66(11):563–566 (1979)) into a variety of cultured cell lines and animals. In addition, several successful clinical trails examining the effectiveness of liposome-mediated drug delivery have been completed (Lopez-Berestein et al., *J Infect Dis.* 151(4):704–710 (1985); Lopez-Berestein et al., *Cancer Drug Deliv.* 2(3):183–189 (1985); Coune, *Infection* 16(3): 141–147 (1988); Sculier et al., *Eur. J. Cancer Clin. Oncol.* 24(3):527–38 (1988)). Furthermore, several studies suggest that the use of liposomes is not associated with autoimmune responses, toxicity or gonadal localization after systemic delivery (Mori and Fukatsu, *Epilepsia* 33(6):994–1000 (1992)).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. (1977), supra; Couvreur et al. (1988), supra), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al. (1987); Quintanar-Guerrero et al., *Pharm Res.* 15(7):1056–1062 (1998); Douglas et al., *Crit. Rev. Ther. Drug Carrier Syst.* 3(3):233–261 (1987)). To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., *J. Pharm. Sci.* 69(2):199–202 (1980); Couvreur et al., (1988), supra; zur Muhlen et al., *Eur. J. Pharm. Biopharm.* 45(2):149–155 (1998); Zambaux et al., *J. Controlled Release* 50(1–3):31–40 (1998); Pinto-Alphandry et al. (1995); and U.S. Pat. No. 5,145,684).

B. Vaccines

In certain preferred embodiments of the present invention, vaccines are provided. The vaccines will generally comprise one or more pharmaceutical compositions, such as those discussed above, in combination with a non-specific immune response enhancer. A non-specific immune response enhancer may be any substance that enhances or potentiates an immune response (antibody and/or cell-mediated) to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, Powell and Newman, eds., "*Vaccine Design (the subunit and adjuvant approach),*" Plenum Press (NY, 1995). Vaccines may be designed to generate antibody immunity and/or cellular immunity such as that arising from CTL or CD4+ T cells.

Pharmaceutical compositions and vaccines within the scope of the present invention may also contain other compounds, which may be biologically active or inactive. For example, one or more immunogenic portions of other *Mycobacterium* antigens may be present, either incorporated into a fusion polypeptide or as a separate compound, within the composition or vaccine. Polypeptides may, but need not, be conjugated to other macromolecules as described, for example, within U.S. Pat. Nos. 4,372,945 and 4,474,757. Pharmaceutical compositions and vaccines may generally be used for prophylactic and therapeutic purposes.

Illustrative vaccines may contain DNA encoding one or more of the polypeptides as described above, such that the polypeptide is generated in situ. Such a polynucleotide may comprise DNA, RNA, a modified nucleic acid or a DNA/RNA hybrid. As noted above, the nucleic acid may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198 (1998), and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321 (1989); Flexner et al., *Ann. N.Y Acad. Sci.* 569:86–103 (1989); Flexner et al., *Vaccine* 8:17–21 (1990); U.S. Pat. Nos. 4,603,112; 4,769,330; and 5,017,487; WO 89/01973; U.S. Pat. No. 4,777,127; GB 2,200,651; EP 0,345,242; WO 91/02805; Berkner, *Biotechniques* 6:616–627 (1988); Rosenfeld et al., *Science* 252:431–434 (1991); Kolls et al., *Proc. Natl. Acad. Sci. USA* 91:215–219 (1994); Kass-Eisler et al., *Proc. Natl. Acad. Sci. USA* 90:11498–11502 (1993); Guzman et al., *Circulation* 88:2838–2848 (1993); and Guzman et al., *Cir. Res.* 73:1202–1207 (1993). Techniques for incorporating DNA into such expression systems are well known to those of ordinary skill in the art. The DNA may also be "naked," as described, for example, in Ulmer et al., *Science* 259:1745–1749 (1993) and reviewed by Cohen, *Science* 259:1691–1692 (1993). The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

In a related aspect, a DNA vaccine as described supra may be administered simultaneously with or sequentially to either a polypeptide of the present invention or a known *Mycobacterium* antigen, such as the 38 kD antigen described above For example, administration of DNA encoding a polypeptide of the present invention, either "naked" or in a delivery system as described supra, may be followed by administration of an antigen in order to enhance the protective immune effect of the vaccine.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium* species or *Mycobacterium* derived proteins. For example, delipidated, deglycolipidated *M. vaccae* ("pVac") can be used. In another embodiment, BCG is used as an adjuvant. In addition, the vaccine can be administered to a subject previously exposed to BCG. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, –7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann & Coffman, *Ann. Rev. Immunol.* 7:145–173 (1989).

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 as disclosed in WO 00/09159. Preferably the formulation additionally comprises an oil in water emulsion and tocopherol.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox (Corixa, Hamilton, Mont.), RC-529 (Corixa, Hamilton, Mont.) and other aminoalkyl glucosaminide 4-phosphates (AGPs), such as those described in pending U.S. Pat. Nos. 6,113,918 and 6,355,237, the disclosures of which are incorporated herein by reference in their entireties, and polyoxyethylene ether adjuvants such as those described in WO 99/52549A1.

Other preferred adjuvants include adjuvant molecules of the general formula (I):

wherein, n is 1–50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index (12$^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438 (1996)) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly (lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

C. Delivery Vehicles

Any of a variety of delivery vehicles may be employed within pharmaceutical compositions and vaccines to facilitate production of an antigen-specific immune response that targets infected cells. Delivery vehicles include antigen presenting cells (APCs), such as dendritic cells, macrophages, B cells, monocytes and other cells that may be engineered to be efficient APCs. Such cells may, but need not be, genetically modified, e.g., to increase the capacity for presenting the antigen, to improve activation and/or maintenance of the T cell response and/or to be immunologically compatible with the receiver (i.e., matched HLA haplotype). APCs may generally be isolated from any of a variety of biological fluids and organs and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251 (1998)) and have been shown to be effective as a physiological adjuvant for eliciting prophylactic or therapeutic immunity (see Timmerman and Levy, *Ann. Rev. Med.* 50:507–529 (1999)). In general, dendritic cells may be identified based on their typical shape (stellate in situ, with marked cytoplasmic processes (dendrites) visible in vitro), their ability to take up process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600 (1998)).

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a *Mycobacterium* antigen (or portion or other variant thereof) such that the *Mycobacterium* polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in, e.g., WO 97/24447, or the gene gun approach described by Mahvi et al., *Immunology and cell Biology* 75:456–460 (1997). Antigen loading of dendritic cells may be achieved by incubating dendritic cells or progenitor cells with the *Mycobacterium* polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

D. Therapeutic Applications of the Compositions of the Invention

In further aspects of the present invention, the compositions described supra may be used for immunotherapy of *Mycobacterium* infection, and in particular tuberculosis. Within such methods, pharmaceutical compositions and vaccines are typically administered to a patient to either prevent the development of *Mycobacterium* infection or to treat a patient afflicted with *Mycobacterium* infection. *Mycobacterium* infection may be diagnosed using criteria generally accepted in the art, such as, e.g., in the case of tuberculosis, fever, acute inflammation of the lung and/or non-productive cough. Pharmaceutical compositions and vaccines may be administered either prior to or following a treatment such as administration of conventional drugs. Administration may be by any suitable route, including, e.g., intravenous, intraperitoneal, intramuscular, subcutaneous, intranasal, intradermal, oral, etc.

Within certain embodiments, immunotherapy may be active immunotherapy, in which treatment relies on the in vivo stimulation of the endogenous host immune system to react against *Mycobacterium* infection with the administration of immune response-modifying agents (such as polypeptides and polynucleotides as provided herein).

Within other embodiments, immunotherapy may be passive immunotherapy, in which treatment involves the delivery of agents with established *Mycobacterium*-immune reactivity (such as effector cells or antibodies) that can directly or indirectly mediate anti-*Mycobacterium* infection effects and do not necessarily depend on an intact host immune system. Examples of effector cells include T cells as discussed above, T lymphocytes (such as CD8$^+$ cytotoxic T lymphocytes and CD4$^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide of the invention. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, (1997)).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by, e.g., injection, intranasal or oral administration.

E. Formulation and Administration

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Routes and frequency of administration, as well as dosage, may vary from individual to individual and may parallel those currently being employed in immunization using BCG. In general, the pharmaceutical compositions and vaccines may be administered, e.g., by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described supra, is capable of raising an immune response in an immunized patient sufficient to protect the patient from *Mycobacterium* infection for at least 1–2 years. When used for a therapeutic purpose, a suitable dose is the amount that is capable of raising and immune response in a patient that is sufficient to obtain an improved clinical outcome (e.g., more frequent cure) in treated patients as compared to non-treated patients. Increases in preexisting immune responses to a *Mycobac-*

*terium* protein generally correlate with an improved clinical outcome. Such immune responses may generally be evaluated using standard proliferation, cytotoxicity or cytokine assays, which may be performed using samples obtained from a patient before and after treatment.

In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.1 ml to about 5 ml.

F. Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a *Mycobacterium* antigen. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a *Mycobacterium* antigen in a biological sample. Such kits generally comprise at least one oligonucleotide probe or primer, as described above, that hybridizes to a polynucleotide encoding a *Mycobacterium* antigen. Such an oligonucleotide may be used, for example, within a PCR or hybridization assay. Additional components that may be present within such kits include a second oligonucleotide and/or a diagnostic reagent or container to facilitate the detection of a polynucleotide encoding a *Mycobacterium* antigen.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

VIII. EXAMPLES

Example 1

Purification and Characterization of *M. Tuberculosis* Polypeptides Using CD4+ T Cell Lines Generated from Human PBMC

*M. tuberculosis* antigens of the present invention were isolated by expression cloning of cDNA libraries of *M. tuberculosis* strains H37Rv and Erdman essentially as described by Sanderson et al. (*J. Exp. Med.,* 182:1751–1757 (1995)) and were shown to induce PBMC proliferation and IFN-γ in an immunoreactive T cell line.

Two CD4+ T cell lines, referred to as DC-4 and DC-5, were generated against dendritic cells infected with *M. tuberculosis*. Specifically, dendritic cells were prepared from adherent PBMC from a single donor and subsequently infected with tuberculosis. Lymphocytes from the same donor were cultured under limiting dilution conditions with the infected dendritic cells to generate the CD4+ T cell lines DC-4 and DC-5. These cell lines were shown to react with crude soluble proteins from *M. tuberculosis* but not with Tb38-1. Limiting dilution conditions were employed to obtain a third CD4+ T cell line, referred to as DC-6, which was shown to react with both crude soluble proteins and Tb38-1.

Genomic DNA was isolated from the *M. tuberculosis* strains H37Rv and Erdman and used to construct expression libraries in the vector pBSK(−) using the Lambda ZAP expression system (Stratagene, La Jolla, Calif.). These libraries were transfonned into *E. coli*, pools of induced *E. coli* cultures were incubated with dendritic cells, and the ability of the resulting incubated dendritic cells to stimulate cell proliferation and IFN-γ production in the CD4+ T cell line DC-6 was examined as described below in Example 2. Positive pools were fractionated and re-tested until pure *M. tuberculosis* clones were obtained.

Nineteen clones were isolated, of which nine were found to contain the previously identified *M. tuberculosis* antigens TbH-9 and Tb38-1, disclosed in U.S. patent application Ser. No. 08/533,634 abandoned. The determined cDNA sequences for the remaining ten clones (hereinafter referred to as Tb224, Tb636, Tb424, Tb436, Tb398, Tb508, Tb441, Tb475, Tb488 and Tb465) are provided in SEQ ID NO:1–10, respectively. The corresponding predicted amino acid sequences for Tb224 and Tb636 are provided in SEQ ID NO:13 and 14, respectively. The open reading frames for these two antigens were found to show some homology to TbH-9. Tb224 and Tb636 were also found to be overlapping clones.

Tb424, Tb436, Tb398. Tb508, Tb441, Tb475, Tb488 and Tb465 were each found to contain two small open reading frames (referred to as ORF-1 and ORF-2) or truncated forms thereof, with minor variations in ORF-1 and ORF-2 being found for each clone. The predicted amino acid sequences of ORF-1 and ORF-2 for Tb424, Tb436, Tb398, Tb508, Tb441, Tb475, Tb488 and Tb465 are provided in SEQ ID NO:16 and 17, 18 and 19, 20 and 21, 22 and 23, 24 and 25, 26 and 27, 28 and 29, and 30 and 31, respectively. In addition, clones Tb424 and Tb436 were found to contain a third apparent open reading frame, referred to as ORF-U. The predicted amino acid sequences of ORF-U for Tb424 and Tb436 are provided in SEQ ID NO:32 and 33, respectively. Tb424 and Tb436 were found to be either overlapping clones or recently duplicated/transposed copies. Similarly Tb398, Tb508 and Tb465 were found to be either overlapping clones or recently duplicated/transposed copies, as were Tb475 and Tb488.

These sequences were compared with known sequences in publicly available sequence databases using the BLASTN system. No homologies to the antigens Tb224 and Tb431 were found. Tb636 was found to be 100% identical to a cosmid previously identified in *M. tuberculosis*. Similarly, Tb508, Tb488, Tb398, Tb424, Tb436, Tb441, Tb465 and Tb475 were found to show homology to known *M. tuberculosis* cosmids. In addition, Tb488 was found to have 100% homology to *M. tuberculosis* topoisomerase I.

Seventeen overlapping peptides to the open reading frames ORF-1 (referred to as 1-1–1-17; SEQ ID NO:34–50, respectively) and thirty overlapping peptides to the open reading frame ORF-2 (referred to as 2-1–2-30, SEQ ID NO:51–80, respectively) were synthesized using the procedure described below in Example 4.

Figure 1B:
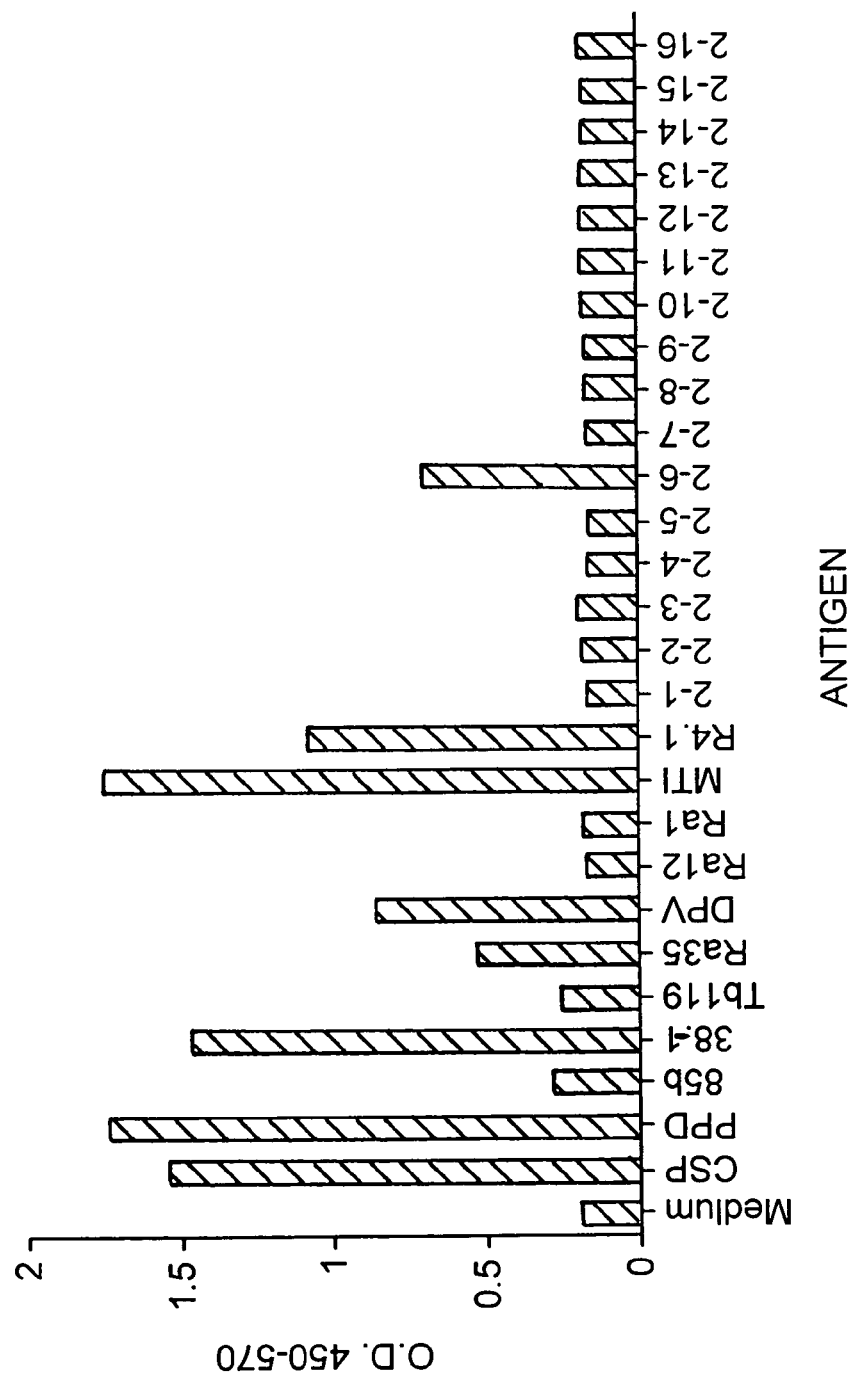
Figure 2A:
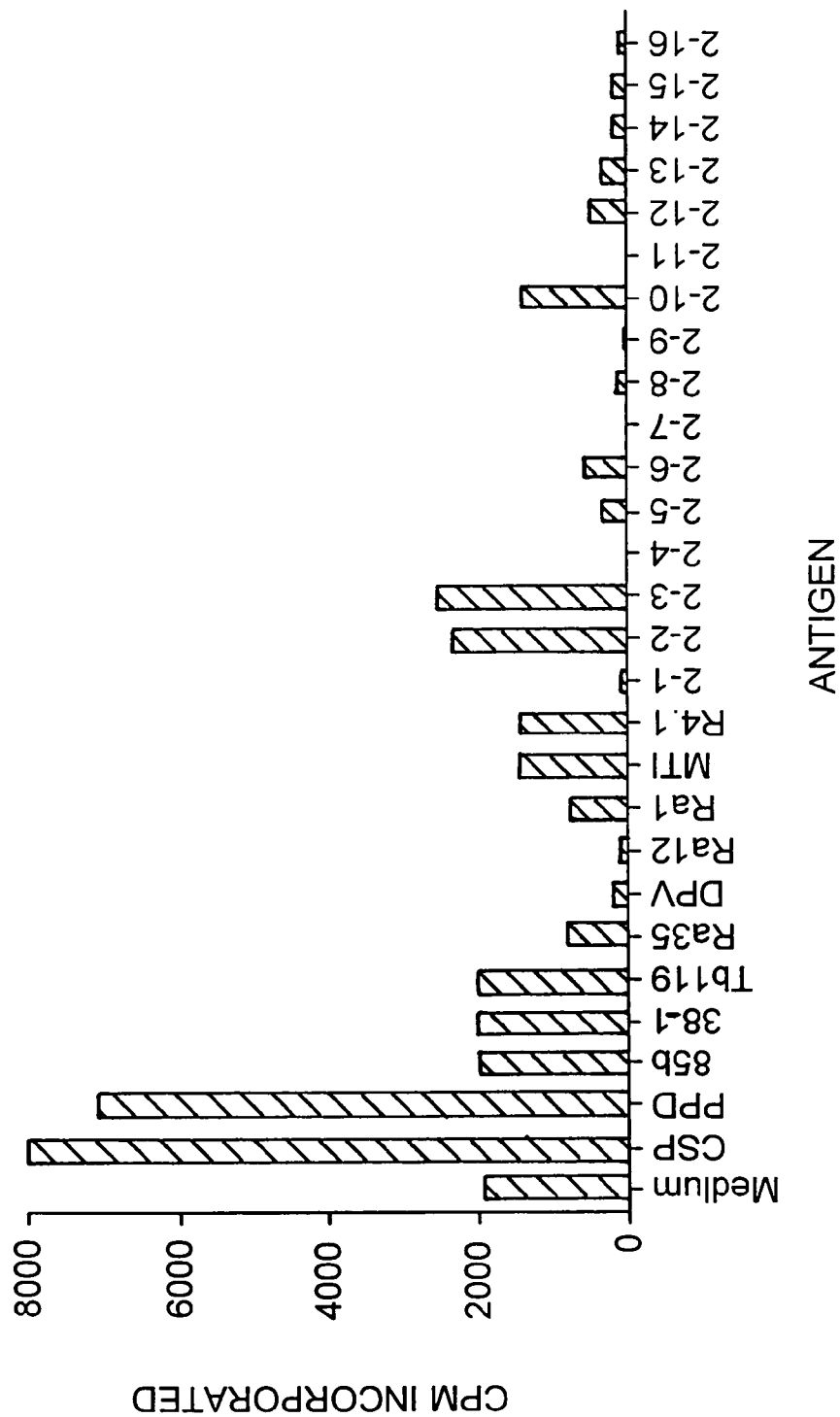
FIGS. 2A and 2B illustrate the stimulation of proliferation and interferon-γ production, respectively, in T cells derived from a second PPD-positive donor (referred to as D160) by recombinant ORF-2 and synthetic peptides to ORF-2.
Figure 2B:
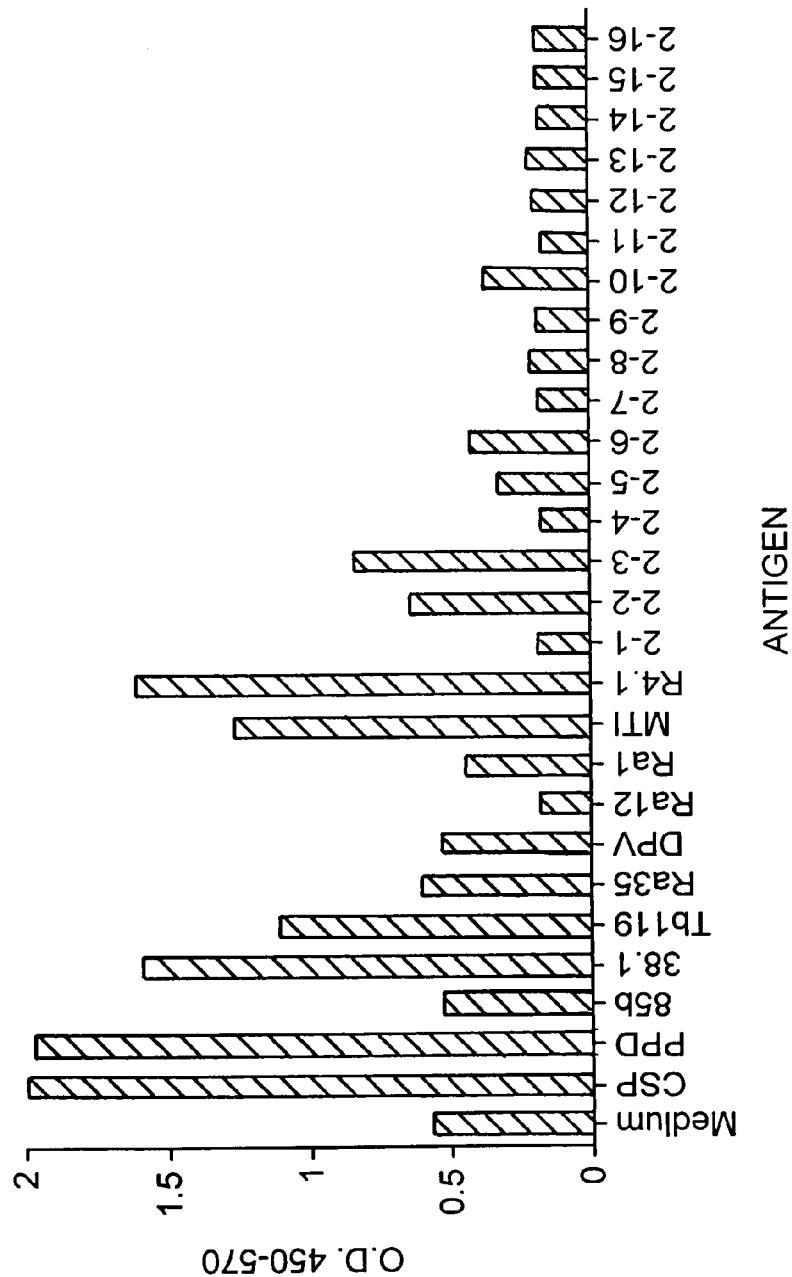

The ability of the synthetic peptides and of recombinant ORF-1 and ORF-2 to induce T cell proliferation and IFN-γ production in PBMC from PPD-positive donors was assayed as described below in Example 2. FIGS. 1A–B and 2A–B illustrate stimulation of T cell proliferation and IFN-γ by recombinant ORF-2 and the synthetic peptides 2-1–2-16 for two donors, referred to as D7 and D160, respectively. Recombinant ORF-2 (referred to as MTI) stimulated T cell proliferation and IFN-γ production in PBMC from both donors. The amount of PBMC stimulation seen with the individual synthetic peptides varied with each donor, indicating that each donor recognizes different epitopes on ORF-2. The proteins encoded by ORF-1, ORF-2 and ORF-U were subsequently named MTS, MTI and MSF, respectively.

Eighteen overlapping peptides to the sequence of MSF (referred to as MSF-1-MSF-18; SEQ ID NO:84–101, respectively) were synthesized and their ability to stimulate T cell proliferation and IFN-γ production in a CD4+ T cell line generated against *M. tuberculosis* culture filtrate was examined as described below. The peptides referred to as MSF-12 and MSF-13 (SEQ ID NO:95 and 96, respectively) were found to show the highest levels of reactivity.

Two overlapping peptides (SEQ ID NO:81 and 82) to the open reading frame of Tb224 were synthesized and shown to induce T cell proliferation and IFN-γ production in PBMC from PPD-positive donors.

Two CD4+ T cell lines from different donors were generated against *M. tuberculosis* infected dendritic cells using the above methodology. Screening of the *M. tuberculosis* cDNA expression library described above using this cell line, resulted in the isolation of two clones referred to as Tb867 and Tb391. The determined cDNA sequence for Tb867 (SEQ ID NO:102) was found to be identical to the previously isolated *M. tuberculosis* cosmid SCY22G10, with the candidate reactive open reading frame encoding a 750 amino acid *M. tuberculosis* protein kinase. Comparison of the determined cDNA sequence for Tb391 (SEQ ID NO:103) with those in publicly available sequence databases revealed no significant homologies to known sequences.

In further studies, CD4+ T cell lines were generated against *M. tuberculosis* culture filtrate, essentially as outlined above, and used to screen the *M. tuberculosis* Erdman cDNA expression library described above. Five reactive clones, referred to as Tb431, Tb472, Tb470, Tb838 and Tb962 were isolated. The determined cDNA sequences for Tb431, Tb472, Tb470, and Tb838 are provided in SEQ ID NO:11, 12, 104 and 105, respectively, with the determined cDNA sequences for Tb962 being provided in SEQ ID NO:106 and 107. The corresponding predicted amino acid sequence for Tb431 is provided in SEQ ID NO:15.

Subsequent studies led to the isolation of a full-length cDNA sequence for Tb472 (SEQ ID NO:108). Overlapping peptides were synthesized and used to identify the reactive open reading frame. The predicted amino acid sequence for the protein encoded by Tb472 (referred to as MSL) is provided in SEQ ID NO:109. Comparison of the sequences for Tb472 and MSL with those in publicly available sequence databases as described above, revealed no homologies to known sequences. Fifteen overlapping peptides to the sequence of MSL (referred to as MSL-1-MSL-15; SEQ ID NO:110–124, respectively) were synthesized and their ability to stimulate T cell proliferation and IFN-γ production in a CD4+ T cell line generated against *M. tuberculosis* culture filtrate was examined as described below. The peptides referred to as MSL-10 (SEQ ID NO:119) and MSL-11 (SEQ ID NO:120) were found to show the highest level of reactivity. Comparison of the determined cDNA sequence for Tb838 with those in publicly available sequence databases revealed identity to the previously isolated *M. tuberculosis* cosmid SCY07H7. Comparison of the determined cDNA sequences for the clone Tb962 with those in publicly available sequence databases revealed some homology to two previously identified *M. tuberculosis* cosmids, one encoding a portion of bactoferritin. However, recombinant bactoferritin was not found to be reactive with the T cell line used to isolate Tb962.

The clone Tb470, described above, was used to recover a full-length open reading frame (SEQ ID NO:125) that showed homology with TbH9 and was found to encode a 40 kDa antigen, referred to as Mtb40. The determined amino acid sequence for Mtb40 is provided in SEQ ID NO:126. Similarly, subsequent studies led to the isolation of the full-length cDNA sequence for Tb431, provided in SEQ ID NO:83, which was also determined to contain an open reading frame encoding Mtb40. Tb470 and Tb431 were also found to contain a potential open reading frame encoding a U-ORF-like antigen.

Screening of an *M. tuberculosis* Erdman cDNA expression library with multiple CD4+ T cell lines generated against *M. tuberculosis* culture filtrate, resulted in the isolation of three clones, referred to as Tb366, Tb433 and Tb439. The determined cDNA sequences for Tb366, Tb433 and Tb439 are provided in SEQ ID NO:127, 128 and 129, respectively. Comparison of these sequences with those in publicly available sequence databases revealed no significant homologies to Tb366. Tb433 was found to show some homology to the previously identified *M. tuberculosis* antigen MPTS3. Tb439 was found to show 100% identity to the previously isolated *M. tuberculosis* cosmid SCY02B10.

A CD4+ T cell line was generated against *M. tuberculosis* PPD, essentially described above, and used to screen the above *M. tuberculosis* Erdman cDNA expression library. One reactive clone (referred to as Tb372) was isolated, with the determined cDNA sequences being provided in SEQ ID NO:130 and 131. Comparison of these sequences with those in publicly available sequence databases revealed no significant homologies.

In further studies, screening of an *M. tuberculosis* cDNA expression library with a CD4+ T cell line generated against dendritic cells that had been infected with tuberculosis for 8 days, as described above, led to the isolation of two clones referred to as Th390R5C6 and Th390R2C11. The determined cDNA sequence for Tb390R5C6 is provided in SEQ ID NO:132, with the determined cDNA sequences for Th390R2C11 being provided in SEQ ID NO:133 and 134. Th390R5C6 was found to show 100% identity to a previously identified *M. tuberculosis* cosmid.

In subsequent studies, the methodology described above was used to screen an *M. tuberculosis* genomic DNA library prepared as follows. Genomic DNA from *M. tuberculosis* Erdman strain was randomly sheared to an average size of 2 kb, and blunt ended with Klenow polymerase, followed by the addition of EcoRI adaptors. The insert was subsequently ligated into the Screen phage vector (Novagen, Madison, Wis.) and packaged in vitro using the PhageMaker extract (Novagen). The phage library (referred to as the Erd λScreen library) was amplified and a portion was converted into a plasmid expression library by an autosubcloning mechanism using the *E. coli* strain BM25.8 (Novagen). Plasmid DNA was purified from BM25.8 cultures containing the pSCREEN recombinants and used to transform competent cells of the expressing host strain BL21(DE3)pLysS. Transformed cells were aliquoted into 96 well microtiter plates with each well containing a pool size of approximately 50 colonies. Replica plates of the 96 well plasmid library format were induced with IPTG to allow recombinant protein expression. Following induction, the plates were centrifuged to pellet the *E. coli* which was used directly in T cell expression cloning of a CD4+ T cell line prepared from a PPD-positive donor (donor 160) as described above. Pools containing *E. coli* expressing *M. tuberculosis* T cell antigens were subsequently broken down into individual colonies and reassayed in a similar fashion to identify positive hits.

Screening of the T cell line from donor 160 with one 96 well plate of the Erd λScreen library provided a total of nine positive hits. Previous experiments on the screening of the pBSK library described above with T cells from donor 160 suggested that most or all of the positive clones would be TbH-9. Tb38-1 or MTI (disclosed in U.S. patent application Ser. No. 08/533,634) or variants thereof. However, Southern analysis revealed that only three wells hybridized with a mixed probe of TbH-9, Tb38-1 and MTI. Of the remaining six positive wells, two were found to be identical. The determined 5' cDNA sequences for two of the isolated clones (referred to as YI-26C1 and YI-86C11) are provided in SEQ ID NO:135 and 136, respectively. The full length cDNA sequence for the isolated clone referred to as hTcc#1 is provided in SEQ ID NO:137, with the corresponding predicted amino acid sequence being provided in SEQ ID NO:138. Comparison of the sequences of hTcc#1 to those in publicly available sequence databases as described above, revealed some homology to the previously isolated *M. tuberculosis* cosmid MTCY07H7B.06.

Example 2

Induction of T Cell Prodiferation and Interferon-γ Production By *M. Tuberculosis* Antigens The ability of recombinant *M. tuberculosis* antigens to induce T-cell proliferation and interferon-γ production may be determined as follows.

Proteins may be induced by IPTG and purified by gel elution, as described in Skeiky et al., *J Exp. Med.* 181: 1527–1537 (1995). The purified polypeptides are then screened for the ability to induce T-cell proliferation in PBMC preparations. The PBMCs from donors known to be PPD skin test positive and whose T-cells are known to proliferate in response to PPD are cultured in medium comprising RPMI 1640 supplemented with 10% pooled human serum and 50 μg/ml gentamicin. Purified polypeptides are added in duplicate at concentrations of 0.5 to 10 μg/ml. After six days of culture in 96-well round-bottom plates in a volume of 200 μl, 50 μl of medium is removed from each well for determination of IFN-γ levels, as described below. The plates are then pulsed with 1 μCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

IFN-γ is measured using an enzyme-linked immunosorbent assay (ELISA). ELISA plates are coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are washed six times in PBS/0.2% TWEEN-20 and samples diluted 1:2 in culture medium in the ELISA plates are incubated overnight at room temperature. The plates are again washed and a polyclonal rabbit anti-human IFN-γ serum diluted 1:3000 in PBS/10% normal goat serum is added to each well. The plates are then incubated for two hours at room temperature, washed and horseradish peroxidase-coupled anti-rabbit IgG (Sigma Chemical So., St. Louis, Mo.) is added at a 1:2000 dilution in PBS/5% non-fat dried milk. After a further two hour incubation at room temperature, the plates are washed and TMB substrate added. The reaction is stopped after 20 min with 1 N sulfuric acid. Optical density is determined at 450 nm using 570 nm as a reference wavelength. Fractions that result in both replicates giving an OD two fold greater than the mean OD from cells cultured in medium alone, plus 3 standard deviations, are considered positive.

Example 3

Purification and Characterization of *M. Tuberculosis* Polypeptides Using CD4+ T Cell Lines Generated From a Mouse *M. Tuberculosis* Model Infection of C57BL/6 mice with *M. tuberculosis* results in the development of a progressive disease for approximately 2–3 weeks. The disease progression is then halted as a consequence of the emergence of a strong protective T cell-mediated immune response. This infection model was used to generate T cell lines capable of recognizing protective *M. tuberculosis* antigens.

Specifically, spleen cells were obtained from C57BL/6 mice infected with *M. tuberculosis* for 28 days and used to raise specific anti-*M. tuberculosis* T cell lines as described above. The resulting CD4+ T cell lines, in conjunction with normal antigen presenting (spleen) cells from C57BL/6 mice were used to screen the *M. tuberculosis* Erd λScreen library described above. One of the reactive library pools, which was found to be highly stimulatory of the T cells, was selected and the corresponding active clone (referred to as Y288C10) was isolated.

Sequencing of the clone Y2SSC10 revealed that it contains two potential genes, in tandem. The determined cDNA sequences for these two genes (referred to as mTCC#1 and mTCC#2) are provided in SEQ ID NO:139 and 140, respectively, with the corresponding predicted amino acid sequences being provided in SEQ ID NO:141 and 142, respectively. Comparison of these sequences with those in publicly available sequence databases revealed identity to unknown sequences previously found within the *M. tuberculosis* cosmid MTY21C12. The predicted amino acid sequences of mTCC#1 and mTCC#2 were found to show some homology to previously identified members of the TbH9 protein family, discussed above.

Example 4

Synthesis of Synthetic Polypeptides

Polypeptides may be synthesized on a Millipore 9050 peptide synthesizer using FMOC chemistry with HIPTU (O-Benzotriazole-N,N,N',N'-tetramethyluroniumn hexafluorophosphate) activation. A Gly-Cys-Gly sequence may be attached to the amino terminus of the peptide to provide a method of conjugation or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

Example 5

Uee of Representative Antigens for Serodiagnosis or Tuberculosis

The diagnostic properties of representative *M. tuberculosis* antigens may be determined by examining the reactivity of antigens with sera from tuberculosis-infected patients and from normal donors as described below.

Assays are performed in 96-well plates coated with 200 ng antigen diluted to 50 µl in carbonate coating buffer, pH 9.6. The wells are coated overnight at 4° C. (or 2 hours at 37° C.). The plate contents are then removed and the wells are blocked for 2 hours with 200 µl of PBS/1% BSA. After the blocking step, the wells are washed five times with PBS/0.1% Tween 20™. 50 µl sera, diluted 1:100 in PBS/0.1% Tween 20/0.1% BSA, is then added to each well and incubated for 30 minutes at room temperature. The plates are washed again five times with PBS/0.1% Tween 20™.

The enzyme conjugate (horseradish peroxidase—Protein A, Zymed, San Francisco, Calif.) is then 1:10,000 in PBS/0.1% Tween20™/0.1% BSA, and 50 µl of the diluted conjugate is added to each well and incubated for 30 minutes at room temperature. Following incubation, the wells are washed five times with PBS/0.1% Tween 20™. 100 µl of tetramethylbenzidine peroxidase (TMB) substrate (Kirkegaard and Perry Laboratories, Gaithersburg, Md.) is added, undiluted, and incubated for about 15 minutes. The reaction is stopped with the addition of 100 µl of 1 $NH_2SO_4$ to each well, and the plates are read at 450 nm.

Example 6

Murine T Cell Expression Cloning of AN MTB Antigen Associated With the Control of TB Infection Genomic DNA form *M. tuberculosis* Erdman strain was randomly sheared to an average size of 2 kb, blunt ended with Klenow polymerase and followed by the addition of EcoRI adaptors. The insert was subsequently ligated into the Screen phage vector predigested with EcoRI (Novagen, Madison, Wis.) and packaged in vitro using the PhageMaker extract (Novagen, Madison, Wis.). The phage library (Erd Screen) was amplified and a portion converted into a plasmid expression library (pScreen) by autosubcloning using the *E. coli* host strain BM25.8 as suggested by the manufacturer (Novagen, Madison, Wis.). Plasmid DNA was purified from BM25.8 cultures containing pScreen recombinants and used to transform competent cells of the expressing host strain BL21(DE3)pLysS. Transformed cells were aliquoted into 96 well micro titer plates with each well containing a pool size of ~50 colonies. Replica plates of the 96 well plasmid library format were induced with IPTG to allow recombinant protein expression. Following induction, the plates were centrifuged to pellet the *E. coli* and the bacterial pellet was resuspended in 200 μl of 1×PBS. The general principle is based on the direct recognition by the T cells of the antigens presented by antigen presenting cells that have internalized a library of *E. coli*-containing expressed recombinant antigens. The *M. tuberculosis* library was initially divided in pools containing approximately 50–100 transformants/ml distributed in 96-well microtiter plates and stored in a replica plate manner. Adherent spleen cells were fed with the *E. coli* pools and incubated for processing for 2 h. After washing the adherent cells were exposed to specific T cell lines in the presence of gentamycin (50 μg/ml) to inhibit the bacterial growth. T cell recognition of pool containing *M. tuberculosis* antigens was then detected by proliferation (3H thymidine incorporation). Wells that scored positive were then broken down using the same protocol until a single clone was detected. The gene was then sequenced, sub-cloned, expressed and the recombinant protein evaluated. Nucleotide sequence comparison of the 0.6 kb insert of clone mTTC#3 with the GenBank database revealed that it is comprised of the amino terminal portion of gene MTV014.03c (locus MTV014; accession #e1248750) of the Mtb H37Rv strain. The full length nucleotide sequence of mTTC#3 (SEQ ID NO:145) is a 1.86 kb fragment comprising the entire ORF with a predicted molecular weight of ~57 kDa (SEQ ID NO:146). Thus, to maintain consistency with our nomenclature, mTTC#3 is referred to hereafter as MTB57. The full length coding portion of mTTC#3 (MTB57) was PCR amplified using the following primer pairs: 5'(5'-CAA TTA CAT ATG CAT CAC CAT CAC CAT CAC ATG AAT TAT TCG GTG TTG CCG (SEQ ID NO:147)) and 3' (5'-CAA TTA AAG CTT TTA GGG CTG ACC GAA GAA GCC (SEQ ID NO:148))h3. The full length nucleic acid coding sequence of mTTC#3 and the corresponding predicted amino acid sequence are provided in FIGS. 3 and 4, respectively.

Example 7

Identification of *Mycobacterium Tuberculosis* Antigens Excreted In Urine of Infected Mice Antigen were prepared by infecting intravenously C57BL/6 mice with $4.10^7$ colony forming units (CFU) of *M. tuberculosis*. 14 days later the animals were bled and their urine was collected in microfuge tubes. Sera were obtained at room temperature. Both sera and urine were centrifuged at 10,000 g for 15 minutes followed by filtration in 0.2u sterile membranes.

Antibodies were produced against the antigens by immunizing normal C57BL/6 mice with either the sera or the urine from the *M. tuberculosis* infected C57BL/6 mice. The adjuvant used was incomplete Freund's adjuvant (IFA). Immunization was carried out according to the following protocol: on day 1, mice were injected in the footpad or in the base of the tail with a mix containing 100 μl of either serum or urine and 100 μl of IFA; on day 14, a mix containing 100 μl of either serum or urine and 100 μl of IFA was injected intraperitoneally to the mice; finally on day 28, either 200 μl of serum or 50 μl of urine were injected to the mice intraperitoneally. By using syngeneic mice for the antibody production, only antibodies specific for foreign antigens present in the blood circulation or urine of the C57BL/6 mice, i.e., *M. tuberculosis* antigens, are generated. On day 35, 100 μl of blood were collected by eye-bleeding the immunized mice. ELISA assays were performed with the obtained sera using a *M. tuberculosis* crude lysate. The ELISA experiments revealed that all the mice immunized with either sera or urine from infected donors produced anti-*M. tuberculosis* antibodies in titers varying from 1/40 to 1/320. No anti-*M. tuberculosis* antibodies were found in the sera obtained from the mice before the immunizations.

The antiserum made against the proteins excreted in the urine was used to screen a Mtb expression library prepared in the lambda screen phage expression system. Positive clones were purified and their corresponding inserts sequenced. These inserts were named P1, 2, 3, 4, 6, 7, 8, 9, 10, 11 and 12 (SEQ ID NO:149–159).

Example 8

Identification of *Mycobacterium Tuberculosis* Antigens Using CD4+ T Cell Expression Cloning Expression screening using a number of T cell lines generated from healthy PPD-positive individuals has been employed to identify *M. tuberculosis* clones encoding reactive antigens. Pools of *M. tuberculosis* recombinant clones (expressed in *E. coli*) were fed to dendritic cells. Autologous T cell lines were incubated with the dendritic cells and proliferation and INF-gamma production was measured. Reactive pools were fractionated and re-tested until pure *M. tuberculosis* clones were achieved. This approach allows for direct screening for T cell antigens. A related approach has been used to identify *Listeria monocytogenes* antigens (see *J. Exp. Med.* 182:1751–1757 (1995).

From the foregoing, it will be appreciated that, although specific embodiments of the invention have been described herein for the purpose of illustration, various modifications may be made without deviating from the spirit and scope of the invention.

What is claimed is:

1. An isolated polypeptide consisting of the amino acid sequence of SEQ ID NO:163.

2. A fusion protein comprising the polypeptide of claim 1 fused to a heterologous polypeptide.

3. The fusion protein of claim 2, wherein the heterologous polypeptide is a *Mycobacterium tuberculosis* polypeptide.

4. The fusion protein of claim 2, wherein the heterlolgous polypeptide is a known *Mycobacterium* antigen.

5. A composition comprising the polypeptide of claim 1 or the fusion protein of claim 2 and a physiologically acceptable carrier.

6. The composition of claim 5, further comprising a non-specific immune response enhancer.

7. The composition of claim 6, wherein the non-specific immune enhancer is an adjuvant.

8. The composition of claim 7, wherein the adjuvant is selected from the group consisting of QS-21, 3D-MPL, GM-CSF, SAF, ISCOMS, MF-59 and RC-529.

9. A diagnostic kit comprising:
   (a) the polypeptide of claim 1 or the fusion protein of claim 3; and
   (b) a detection reagent.

10. The kit of claim 9, wherein the polypeptide or fusion protein is immobilized on a solid support.

11. The kit of claim 9, wherein the detection reagent comprises a reporter group conjugated to a binding agent.

12. The kit of claim 11, wherein the binding agent is selected from the group consisting of anti-immunoglobulins, Protein G, Protein A and lectins.

13. The kit of claim 11, wherein the reporter group is selected from the group consisting of radioisotopes, fluorescent groups, luminescent groups, enzymes, biotin and dye particles.

14. A diagnostic kit comprising:
   (a) the polypeptide of claim 1 or the fusion protein of claim 2; and
   (b) an apparatus for contacting the polypeptide or the fusion protein with the dermal cells of a patient.

* * * * *

SEQUENCE LISTING

<160> NUMBER OF SEQ ID NOS: 164

<210> SEQ ID NO 1
<211> LENGTH: 1886
<212> TYPE: DNA
<213> ORGANISM: Mycobacterium tuberculosis
<220> FEATURE:
<223> OTHER INFORMATION: Tb224 cDNA
<221> NAME/KEY: modified_base
<222> LOCATION: (1)..(1886)
<223> OTHER INFORMATION: n = g, a, c or t

<400> SEQUENCE: 1

```
cgctctggtg accaccaact tcttcggtgt caacaccatc ccgatcgccc tcaacgaggc      60
cgactacctg cgcatgtgga tccaggccgc caccgtcatg agccactatc aagccgtcgc     120
gcacgaaatc tggtgtctcc atgaatangc cagttcggga aagccgtggg ccagtatcac     180
cacgggtgcg ccgggctcac cggcctcgac cactcgcagt cgcacgccgt tggtatcaac     240
taaccgtncn gtangtgcgc ccatcgtctc accaaatcac accgggcacc ggcctgagaa     300
gggcttgggg agcanccaga ggcgattgtc gcgggtgctg ccgcgcatca ttgatcggcc     360
ggccggacca ntcgggcctc ccttgacgtc cggatcncac ttcctgtgca gctggcatgg     420
ctacagctca cagtgactgc cccacgattg ccggccaggt ccagttcaaa ttccggtgaa     480
ttcgcggaca aaagcagcag gtcaaccaac cgcagtcagt cgagggtccc aaacgtgagc     540
caatcggtga aatggcttgc tgcagtgaca ccggtcacag gcttagccga cagcaccgga     600
atagctcagg cgggctatag agtcctatag aaacatttgc tgatagaatt aaccgctgtc     660
ttggcgtgat cttgatacgg ctcgccgtgc gaccggttgg ctcagtagct gaccaccatg     720
taacccatcc tcggcaggtg tctactaagg cgagacaccg cattggtggg gctgcatcgc     780
aaatcggtcc gagcatgtag cactgccgtt atcccgggat agcaaaccac ccggaaccag     840
ggctatccca gtcgctctcc gacggaggcc gtttcgcttt ccgttgcccg ataactcccg     900
agtggatatc ggcgttatca nattcaggct tttcttcgca aggtaccggt gttcgctata     960
ttcggatatc tcggacggat aattactaaa acttcagtgg tttagataag gccgccgcaa    1020
tacttcgccg atcttgccga gcgcaacgga tttccatcgt cggttttcgt cgccttatca    1080
aacatgatcg gagataatga cagatcggcc tagctaggtg tttagcggac gcgatttagg    1140
acaaccgaga tttgctttgc ctcgcaacca tgagagcgcc ccgcttcgac gccgaatcgg    1200
gtgagtgatg gtgggttagc acagccctga ttgcgccacc ggcgaggtga ttgtgcccgc    1260
```

```
cacgaggccg ccgccggcta gccccatgag cacgntatat agactctcct gcaacagatc    1320
tcataccgat cgaaggcgaa gcgcaggcat cgacgtcgga gacactgcct tgggatcgcg    1380
ccgcctacac ggcggttggc gcattgtcgc agcgcagttg caggagggca aatgtgcgca    1440
gacgatgtag tcgacaacaa gtgnacatgc cgtcttcacg aactcaaaac tgacgatctg    1500
cttagcatga aaaaaactgt tgacatcggc aagcatgac agccgactg taggcctacg     1560 cgtgcaatgc agaaccaagg ntatgcatgg aatcgacgac cgttgagata ggcggcaggc    1620
atgagcagag cgttcatcat cgatccaacg atcagtgcca ttgacggctt gtacgacctt    1680
ctggggattg gaatacccaa ccaaggggt atcctttact cctcactaga gtacttcgaa     1740
aaagccctgg aggagctggc agcagcgttt ccgggtgatg gctggttagg ttcggccgcg    1800
gacaaatacg ccggcaaaaa ccgcaaccac gtgaattttt tccaggaact ggcagacctc    1860
gatcgtcagc tcatcagcct gatcca                                         1886

<210> SEQ ID NO 2
<211> LENGTH: 2305
<212> TYPE: DNA
<213> ORGANISM: Mycobacterium tuberculosis
<220> FEATURE:
<223> OTHER INFORMATION: Tc636 cDNA
<221> NAME/KEY: modified_base
<222> LOCATION: (1)..(2305)
<223> OTHER INFORMATION: n = g, a, c or t

<400> SEQUENCE: 2
ggcacgcgct ggccgcgcaa tacaccgaaa ttgcaacgga actcgcaagc gtgctcgctg     60
cggtgcaggc aagctcgtgg caggggccca gcgccgaccg gttcgtcgtc gcccatcaac    120
cgttccggta ttggctaacc cacgctgcca cggtggccac cgcagcagcc gccgcgcacn    180
aaacggccgc cgccgggtat acgtccgcat tggggggcat gcctacgcta gccgagttgg    240
cggccaacca tgccatgcac ggcgctctgg tgaccaccaa cttcttcggt gtcaacacca    300
tcccgatcgc cctcaacgag gccgactacc tgcgcatgtg gatccaggcc gccaccgtca    360
tgagccacta tcaagccgtc gcgcacgaaa gcgtggcggc gaccccagc acgccgccgg    420 cgccgcagat agtgaccagt gcggccagct cggcggctag cagcagcttc ccgacccga    480 ccaaattgat cctgcagcta ctcaaggatt tcctggagct gctgcgctat ctggctgttg    540
agctgctgcc ggggccgctc ggcgacctca tcgcccaggt gttggactgg ttcatctcgt    600
tcgtgtccgg tccagtcttc acgtttctcg cctacctggt gctggaccca ctgatctatt    660
tcggaccgtt cgccccgctg acgagtccgg tcctgttgcc tgctgtggag ttacgcaacc    720
gcctcaaaac cgccaccgga ctgacgctgc cacctaccgt gattttcgat catcccactc    780
ccactgcggt cgccgagtat gtcgcccagc aaatgtctgg cagccgccca acggaatccg    840
gtgatccgac gtcgcaggtt gtcgaacccg ctcgtgccga attcggcacg agtgctgttc    900
atcaaatccc cccgagacct gcggacaccc ggcgcgcttg ccgacatcga gatgatgtcc    960
cgcgagatag cagaattgcc caacatcgtg atggtgcggg gcttgacccg accgaacggg    1020
gaacctctga aggagaccaa ggtctcgttt caggctggtg aagtgggcgg caagctcgac    1080
gaagcgacca ccctgctcga agagcacgga ggcgagctgg accagctgac cggcggtgcg    1140
caccagttgg ccgacgccct cgcccaaata cgcaacgaaa tcaatggggc cgtggccagc    1200
tcgagcggga tagtcaacac cctgcaggcc atgatggacc tgatgggcgg tgacaagacc    1260
atccgacaac tggaaaatgc gtcccaatat gtcgggcgca tgcgggctct ggggggacaat   1320
```

```
ctgagcggga ccgtcaccga tgccgaacaa atcgccactt gggccagccc tatggtcaac    1380
gccctcaact ccagcccggt gtgtaacagc gatcccgcct gtcggacgtc gcgcgcacag    1440
ttggcggcga ttgtccaggc gcaggacgac ggcctgctca ggtccatcag agcgctagcc    1500
gtcaccctgc aacagacgca ggaataccag acactcgccc ggacggtgag cacactggac    1560
gggcaactga agcaagtcgt cagcaccctc aaagcggtcg acggcctacc caccaaattg    1620
gctcaaatgc agcaaggagc caacgctctc gccgacggca gcgcagcgct ggcggcaggc    1680
gtgcaggaat tggtcgatca ggtcaaaaag atgggctcag gctcaacga ggccgccgac     1740 ttcctgttgg ggatcaagcg ggatgcggac aagccgtcaa tggcgggctt caacattcca    1800
ccgcagattt tttcgaggga cgagttcaag aagggcgccc agattttcct gtcggccgat    1860
ggtcatgcgg cgcggtactt cgtgcagagc gcgctgaatc cggccaccac cgaggcgatg    1920
gatcaggtca acgatatcct ccgtgttgcg gattccgcgc gaccgaatac cgaactcgag    1980
gatgccacga taggtctggc gggggttccg actgcgctgc gggatatccg cgactactac    2040
aacagcgata tgaaattcat cgtcattgcg acgatcgtta tcgtattctt gattctcgtc    2100
attctgntgc gcgcacttgt ggntccgata tatctgatag gctcggtgct gatttcttac    2160
ttgtcggccc taggcatagg aactttcgtt ttccaattga tactgggcca ggaaatgcat    2220
tggagcctgc cgggactgtc cttcatatta ttggttgcca tcggcgctga ctacaacatg    2280
ctgctcattt cacgcatccg cgacg                                          2305
```

<210> SEQ ID NO 3
<211> LENGTH: 1742
<212> TYPE: DNA
<213> ORGANISM: Mycobacterium tuberculosis
<220> FEATURE:
<223> OTHER INFORMATION: Tb424 cDNA
<221> NAME/KEY: modified_base
<222> LOCATION: (1)..(1742)
<223> OTHER INFORMATION: n = g, a, c or t

<400> SEQUENCE: 3

```
ccgctctctt tcaacgtcat aagttcggtg ggccagtcgg ccgcgcgtgc atatggcacc      60 ataacgcgt gtcccatgga tacccggacc gcacgacggt agagcggatc agcgcagccg     120
gtgccgaaca ctaccgcgtc cacgctcagc cctgccgcgt tgcggaagat cgagcccagg    180
ttctcatggt cgttaacgcc ttccaacact gcgacggtgc gcgccccggc gaccacctga    240
gcaacgctcg gctccggcac ccggcgcgcg gctgccaaca ccccacgatt gagatggaag    300
ccgatcaccc gtgccatgac atcagccgac gctcgatagt acggcgcgcc gacaccggcc    360
agatcatcct tgagctcggc cagccggcgg tcggtgccga acagcgccag cggcgtgaac    420
cgtgaggcca gcatgcgctg caccaccagc acaccctcgg cgatcaccaa cgccttgccg    480
gtcggcagat cgggacnacn gtcgatgctg ttcaggtcac ggaaatcgtc gagccgtggg    540
tcgtcgggat cgcagacgtc ctgaacatcg aggccgtcgg ggtgctgggc acaacggcct    600
tcggtcacgg gctttcgtcg accagagcca gcatcagatc ggcggcgctg cgcaggatgt    660
cacgctcgct gcggttcagc gtcgcgagcc gctcagccag ccactcttgc agagagccgt    720
tgctgggatt aattgggaga ggaagacagc atgtcgttcg tgaccacaca gccggaagcc    780
ctggcagctg cggcggcgaa cctacagggt attggcacga caatgaacgc cagaacgcg     840 gccgcggctc ctccaaccac cggagtagtg cccgcagccg ccgatgaagt atcagcgctg    900
accgcggctc agtttgctgc gcacgcgcag atgtaccaaa cggtcagcgc ccaggccgcg    960
```

```
gccattcacg aaatgttcgt gaacacgctg gtggccagtt ctggctcata cgcggccacc    1020
gaggcggcca acgcagccgc tgccggctga acgggctcgc acgaacctgc tgaaggagag    1080
ggggaacatc cggagttctc gggtcagggg ttgcgccagc gcccagccga ttcagntatc    1140
ggcgtccata acagcagacg atctaggcat tcagtactaa ggagacaggc aacatggcct    1200
cacgttttat gacggatccg catgcgatgc gggacatggc gggccgtttt gaggtgcacg    1260
cccagacggt ggaggacgag gctcgccgga tgtgggcgtc cgcgcaaaac atttccggtg    1320
cgggctggag tggcatggcc gaggcgacct cgctagacac catgacctag atgaatcagg    1380
cgtttcgcaa catcgtgaac atgctgcacg gggtgcgtga cgggctggtt cgcgacgcca    1440
acaantacga acagcaagag caggcctccc agcagatcct gagcagntag cgccgaaagc    1500
cacagctgng tacgntttct cacattagga gaacaccaat atgacgatta attaccagtt    1560
cggggacgtc gacgctcatg gcgccatgat ccgcgctcag gcggcgtcgc ttgaggcgga    1620
gcatcaggcc atcgttcgtg atgtgttggc cgcgggtgac ttttgggcg cgccggttc    1680 ggtggcttgc caggagttca ttacccagtt gggccgtaac ttccaggtga tctacgagca    1740
gg                                                                   1742
```

<210> SEQ ID NO 4
<211> LENGTH: 2836
<212> TYPE: DNA
<213> ORGANISM: Mycobacterium tuberculosis
<220> FEATURE:
<223> OTHER INFORMATION: Tb436 cDNA
<221> NAME/KEY: modified_base
<222> LOCATION: (104)
<223> OTHER INFORMATION: n = g, a, c or t

<400> SEQUENCE: 4

```
gttgattccg ttcgcggcgc cgccgaagac caccaactcc gctggggtgg tcgcacaggc      60
ggttgcgtcg gtcagctggc cgaatcccaa tgattggtgg ctcngtgcgg ttgctgggct     120
cgattacccc cacggaaagg acgacgatcg ttcgtttgct cggtcagtcg tacttggcga     180
cgggcatggc gcggtttctt acctcgatcg cacagcagct gaccttcggc ccaggggca     240 caacggctgg ctccggcgga gcctggtacc caacgccaca attcgccggc ctgggtgcag     300
gcccggcggt gtcggcgagt ttggcgcggg cggagccggt cgggaggttg tcggtgccgc     360
caagttgggc cgtcgcggct ccggccttcg cggagaagcc tgaggcgggc acgccgatgt     420
ccgtcatcgg cgaagcgtcc agctgcgtc agggaggcct gcttcgaggc ataccgctgg     480
cgagagcggg gcggcgtaca ggcgccttcg ctcaccgata cgggttccgc cacagcgtga     540
ttacccggtc tccgtcggcg ggatagcttt cgatccggtc tgcgcggccg ccggaaatgc     600
tgcagatagc gatcgaccgc gccggtcggt aaacgccgca cacggcacta tcaatgcgca     660
cggcgggcgt tgatgccaaa ttgaccgtcc gacggggct tatctgcgg caagatttca     720 tccccagccc ggtcggtggg ccgataaata cgctggtcag cgcgactctt ccggctgaat     780
tcgatgctct gggcgcccgc tcgacgccga gtatctcgag tgggccgcaa acccggtcaa     840
acgctgttac tgtggcgtta ccacaggtga atttgcggtg ccaactggtg aacacttgcg     900
aacgggtggc atcgaaatca acttgttgcg ttgcagtgat ctactctctt gcagagagcc     960
gttgctggga ttaattggga gaggaagaca gcatgtcgtt cgtgaccaca cagccggaag    1020
ccctggcagc tgcggcggcg aacctacagg gtattggcac acaatgaac gcccagaacg    1080 cggccgcggc tgctccaacc accggagtag tgcccgcagc cgccgatgaa gtatcagcgc    1140
```

-continued

```
tgaccgcggc tcagtttgct gcgcacgcgc agatgtacca aacggtcagc gcccaggccg    1200
cggccattca cgaaatgttc gtgaacacgc tggtggccag ttctggctca tacgcggcca    1260
ccgaggcggc caacgcagcc gctgccggct gaacgggctc gcacgaacct gctgaaggag    1320
agggggaaca tccggagttc tcgggtcagg ggttgcgcca gcgcccagcc gattcagcta    1380
tcggcgtcca taacagcaga cgatctaggc attcagtact aaggagacag caacatggc     1440 ctcacgtttt atgacggatc cgcatgcgat gcgggacatg gcgggccgtt ttgaggtgca    1500
cgcccagacg gtggaggacg aggctcgccg gatgtgggcg tccgcgcaaa acatttccgg    1560
tgcgggctgg agtggcatgg ccgaggcgac ctcgctagac accatgacct agatgaatca    1620
ggcgtttcgc aacatcgtga acatgctgca cggggtgcgt gacgggctgg ttcgcgacgc    1680
caacaactac gaacagcaag agcaggcctc ccagcagatc ctgagcagct agcgccgaaa    1740
gccacagctg cgtacgcttt ctcacattag gagaacacca atatgacgat taattaccag    1800
ttcggggacg tcgacgctca tggcgccatg atccgcgctc aggcggcgtc gcttgaggcg    1860
gagcatcagg ccatcgttcg tgatgtgttg gccgcgggtg acttttgggg cggcgccggt    1920
tcggtggctt gccaggagtt cattacccag ttgggccgta acttccaggt gatctacgag    1980
caggccaacg cccacgggca gaaggtgcag gctgccggca caacatggc gcaaaccgac     2040 agcgccgtcg gctccagctg ggcctaaaac tgaacttcag tcgcggcagc acaccaacca    2100
gccggtgtgc tgctgtgtcc tgcagttaac tagcactcga ccgctgaggt agcgatggat    2160
caacagagta cccgcaccga catcaccgtc aacgtcgacg gcttctggat gcttcaggcg    2220
ctactggata tccgccacgt tgcgcctgag ttacgttgcc ggccgtacgt ctccaccgat    2280
tccaatgact ggctaaacga gcacccgggg atggcggtca tgcgcgagca gggcattgtc    2340
gtcaacgacg cggtcaacga acaggtcgct gcccggatga aggtgcttgc cgcacctgat    2400
cttgaagtcg tcgccctgct gtcacgcggc aagttgctgt acggggtcat agacgacgag    2460
aaccagccgc cgggttcgcg tgacatccct gacaatgagt tccgggtggt gttggcccgg    2520
cgaggccagc actgggtgtc ggcggtacgg gttggcaatg acatcaccgt cgatgacgtg    2580
acggtctcgg atagcgcctc gatcgccgca ctggtaatgg acggtctgga gtcgattcac    2640
cacgccgacc cagccgcgat caacgcggtc aacgtgccaa tggaggagat ctcgtgccga    2700
attcggcacg aggcacgagg cggtgtcggt gacgacggga tcgatcacga tcatcgaccg    2760
gccgggatcc ttggcgatct cgttgagcac gacccgggcc cgcgggaagc tctgcgacat    2820
ccatgggttc ttcccg                                                    2836
```

<210> SEQ ID NO 5
<211> LENGTH: 900
<212> TYPE: DNA
<213> ORGANISM: Mycobacterium tuberculosis
<220> FEATURE:
<223> OTHER INFORMATION: Tb398 cDNA
<221> NAME/KEY: modified_base
<222> LOCATION: (810)
<223> OTHER INFORMATION: n = g, a, c or t

<400> SEQUENCE: 5

```
aacatgctgc acggggtgcg tgacgggctg gttcgcgacg ccaacaacta cgagcagcaa     60
gagcaggcct cccagcagat cctcagcagc taacgtcagc cgctgcagca caatactttt    120
acaagcgaag gagaacaggt tcgatgacca tcaactatca gttcggtgat gtcgacgctc    180
acggcgccat gatccgcgct caggccgggt tgctggaggc cgaacatcag gccatcattc    240
```

-continued

```
gtgatgtgtt gaccgcgagt gacttttggg gcggcgccgg ttcggcggcc tgccaggggt    300
tcattaccca attgggccgt aacttccagg tgatctacga acaggccaac gcccacgggc    360
agaaggtgca ggctgccggc aacaacatgg cgcaaaccga cagcgccgtc ggctccagct    420
gggcctgaca ccaggccaag gccagggacg tggtgtacga gtgaaggttc ctcgcgtgat    480
ccttcgggtg gcagtctagg tggtcagtgc tggggtgttg gtggtttgct gcttggcggg    540
ttcttcggtg ctggtcagtg ctgctcgggc tcgggtgagg acctcgaggc ccaggtagcg    600
ccgtccttcg atccattcgt cgtgttgttc ggcgaggacg gctccgacga ggcggatgat    660
cgaggcgcgg tcgggggaaga tgcccacgac gtcggttcgg cgtcgtacct ctcggttgag    720
gcgttcctgg gggttgttgg accagatttg gcgccagatc ttcttgggga aggcggtgaa    780
cgccagcagg tcggtgcggg cggtgtcgan gtgctcggcc accgcgggga gtttgtcggt    840
cagagcgtcg agtacccgat catattgggc aacaactgat tcggcgttgg gctggtcgta    900
```

<210> SEQ ID NO 6
<211> LENGTH: 1905
<212> TYPE: DNA
<213> ORGANISM: Mycobacterium tuberculosis
<220> FEATURE:
<223> OTHER INFORMATION: Tb508 cDNA
<221> NAME/KEY: modified_base
<222> LOCATION: (1)..(1905)
<223> OTHER INFORMATION: n = g, a, c or t

<400> SEQUENCE: 6

```
gctcgccgga tgtgggcgtc cgcgcaaaac atttccggtg cgggctggag tggcatggcc     60
gaggcgacct cgctagacac catggcccag atgaatcagg cgtttcgcaa catcgtgaac    120
atgctgcacg gggtgcgtga cgggctggtt cgcgacgcca acaactacga gcagcaagag    180
caggcctccc agcagatcct cagcagctaa cgtcagccgc tgcagcacaa tactttttaca    240
agcgaaggag aacaggttcg atgaccatca actatcagtt cggtgatgtc gacgctcacg    300
gcgccatgat ccgcgctcag gccgggttgc tggaggccga gcatcaggcc atcattcgtg    360
atgtgttgac cgcgagtgac ttttggggcg gcgccggttc ggcggcctgc cagggggttca    420
ttacccagtt gggccgtaac ttccaggtga tctacgaaca agccaacacc cacgggcaga    480
aggtgcaagc tgccggcaac aacatggcgc aaaccgacag cgccgtcngc tccagctggg    540
cctgacacca ggccaaggcc agggacgtgg tgtacnagtg aaggttcctc gcgtgatcct    600
tcgggtggca gtctaggtgg tcagtgctgg ggtgttggtg gtttgctgct tggcgggttc    660
ttcggtgctg gtcagtgctg ctcgggctcg gtgaggacc tcgaggccca ggtagcgccg    720
tccttcgatc cattcgtcgt gttgttcggc gaggacngct ccgacgangc ggatgatcga    780
ggcgcggtcg gggaagatgc ccacgacgtc ggttcggcgt cgtacctctc ggttgaagcg    840
ttcctggggg ccaccgcttg gcgccnangc actccacgcc aattcgtcnc acctaacagc    900
ggtggccaac gactatgact acgacaccgt ttttgccagg gccctcnaaa ggatctgcgc    960
gtcccggcga cacgcttttt gcgataagta cctccggcaa ttctatgagt gtactgcggn   1020
ccgcgaaaac cgcaagggag ttgggtgtga cggttnttgc aaatgacggg cgaatccggc   1080
ggccagctgg cagaattcgc agatttcttg atcaacgtcc cgtcacgcga caccgggcga   1140
atccaggaat ctcacatcgt ttttattcat gcgatctccg aacatgtcga cacgcgcttt   1200
tcgcgcctc gccaatagga aagccgatcc ttacgcggcc attcgaaaga tggtcgcgga   1260
acgtgcggga caccaatggt gtctcttcct cgatagagac ggggtcatca atcgacaagt   1320
```

-continued

```
ggtcggcgac tacgtacgga actggcggca gtttgaatgg ttgcccgggg cggcgcgggc    1380
gttgaagaag ctacgggcat gggctccgta catcgttgtc gtgacaaacc agcagggcgt    1440
gggtgccgga ttgatgagcg ccgtcgacgt gatggtgata catcggcacc tccaaatgca    1500
gcttgcatcc gatggcgtgc tgatagatgg atttcaggtt tgcccgcacc accgttcgca    1560
gcggtgtggc tgccgtaagc cgagaccggg tctggtcctc gactggctcg gacgacaccc    1620
cgacagtgag ccattgctga gcatcgtggt tggggacagc ctcagcgatc ttgacattgg    1680
cacacaacgt cgccgctgct gccggtgcat gtgccagtgt ccagataggg ggcgccagtt    1740
ctggcggtgt cgctgacgcg tcatttgact cgctctggga gttcgctgtc gcagtcggac    1800
atgcgcgggg ggagcgggc taatggcgat cttgcgcggg cgagcgccgt ngcggntcgg    1860
actnngcggt ggcgggacag acgtggaacc gtactcgagc cagtt    1905
```

```
<210> SEQ ID NO 7
<211> LENGTH: 2921
<212> TYPE: DNA
<213> ORGANISM: Mycobacterium tuberculosis
<220> FEATURE:
<223> OTHER INFORMATION: Tb441 cDNA
<221> NAME/KEY: modified_base
<222> LOCATION: (1)..(2921)
<223> OTHER INFORMATION: n = g, a, c or t

<400> SEQUENCE: 7
```

```
cgggatgccg tggtggttgg tattgcccaa accctggcgc tggtcccgg ggtatccagg      60 tccgggtcga ccatcagcgc tggactgttt ctcggactcg accgtgaact ggccgcccga     120
ttcggattcc tgctggccat tccagcggtg ttcgcctccg ggttgttctc gttgcccgac     180
gcattccacc cggtaaccga gggcatgagc gctactggcc cgcagttgct ggtggccacc     240
ctgatcgcgt tcgtcctcgg tctgaccgcg gtggcctggc tgctgcggtt tctggtgcga     300
cacaacatgt actggttcgt cggctaccgg gtgctcgtcg ggacgggcat gctcgtgctg     360
ctggctaccg ggacggtagc cgcgacatga ccgtcatctt gctacgccat gcccgttcca     420
cctcgaacac cgcgggcgtg ctggccggcc ggtccggcgt cgacctcgac gagaaggggc     480
gcgagcaggc caccgggttg atcgatcgaa ttggtgacct gccgatccgg gcggtcgcgt     540
cttctccaat gctgcggtgt caacgcaccg tcgaaccgct ggccgaggcg ctgtgcctgg     600
agccgctcat cgatgaccgg ttctccgaag tcgactacgg cgaatggact ggcagaaaaa     660
tcggtgacct ggtcgacgag ccgttgtggc gggtagtcca gcccacccc agcgcggcgg     720 tgtttcccgg cggtgagggt ttggcgcagg tgcagacgtg gttgtcctga cggatttcca     780
tgccggggaa caccaagacc ggatcggcac tggcggtcgc cggcgaaaac ccggccgcca     840 ataggggcgac cgtcgctgcg aatgcgcgtg gtaccaggcg gaccaccttg aactcccatc     900
cgtcggggcc aagcgcatcg cccgccgccg gttacggcta aggcgtacca aaacccgacg     960
gtaatacttc ggcaatgtcg ggtcncgacg ttaccgagac gtgaccagng aggcngcggc    1020
attggattta tcgatggtgc gcggttccca ncccggcgt ccgaaacgt agcccagccg      1080 atcccgcaga cgtgttgccg accgccagtc acgcacgatc gccacgtact cgcgggtctg    1140
cagcttccag atgttgaacg tgtcgacccg cttggtcagg ccataatgcg gtcggaatag    1200
ctccggctga agctaccga acaggcggtc ccagatgatg aggatgccgc catagttctt     1260
gtccanatac accgggtcca ttccgtggtg gacccgtggg tgcgacgggg tattgaagac     1320
gaattcgaac caccgcggca gcctgtcgat ccgctcggtg tgcacccaga actggtagat     1380
```

```
caagttcagc gaccaattgc agaacaccat ccaaggggga agccccatca gtggcagcgg      1440
aacccacatg agaatctcgc cgctgttgtt ccantttctg gcgcagcgcg gtggcgaagt      1500
tgaagtattc gctggagtga tgcgcctggt gggtagccca gatcagccga actcggtggg      1560
cgatgcggtg ataggagtag tacagcagat cgacaccaac gatcgcgatc acccaggtgt      1620
accaccggtg ggcggacagc tgccagggcg caagtaggc atagattgcg gcataaccga       1680
gcagggcaag ggacttccag ccggcggtgg tggctatcga aaccagcccc atcgagatgc      1740
tggccaccga gtcgcgggtg aggtaagcgc ccgaggcggg ccgtggctgc ccggtagcag      1800
cggtctcgat gctttccagc ttgcgggccg ccgtccattc gagaatcagc agcaatagaa      1860
aacatggaat ggcgaacagt accgggtccc gcatttcctc gggcagcgct gagaagaatc      1920
cggcgacggc atggccgagg cgacctcgnt agacaccatg acccagatga atcaggcgtt      1980
tcgcaacatc gtgaacatgc tgcacggggg cgtgacggg ctggttcgcg acgccaacaa       2040
ntacgaacag caagagcagg cctcccagca gatcctcagc agctgacccg gcccgacgac      2100
tcaggaggac acatgaccat caactatcaa ttcggggacg tcgacgctca cggcgccatg      2160
atccgcgctc aggccgggtc gctggaggcc gagcatcagg ccatcatttc tgatgtgttg      2220
accgcgagtg acttttgggg cggcgccggt tcggcggcct gccagggggtt cattacccag     2280 ctgggccgta acttccaggt gatntacgag caggccaacg cccacgggca gaaggtgcag      2340
gctgccggca caacatggc acaaaccgac agcgccgtcg gctccagctg ggcataaagn       2400
tggcttaagg cccgcgccgt caattacaac gtggccgcac accggttggt gtgtggccac      2460
gttgttatct gaacgactaa ctacttcgac ctgctaaagt cggcgcgttg atccccggtc      2520
ggatggtgct gaactgggaa gatggcctca atgcccttgt tgcggaaggg attgaggcca      2580
tcgtgtttcg tactttaggc gatcagtgct ggttgtggga gtcgctgctg cccgacgagg      2640
tgcgccgact gcccgaggaa ctggcccggg tggacgcatt gttggacgat ccggcgttct      2700
tcgccccgtt cgtgccgttc ttcgacccgc gcaggggccg ccgtcgacg ccgatggagg       2760 tctatctgca gttgatgttt gtgaagttcc gctaccggct gggctatgag tcgctgtgcc      2820
gggaggtggc tgattcgatc acctgacggc ggttttgccg cattgcgctg acgggtcgg       2880 tgccgcatcc gaccacattg atgaagctca ccacgcgttg c                         2921
```

<210> SEQ ID NO 8
<211> LENGTH: 1704
<212> TYPE: DNA
<213> ORGANISM: Mycobacterium tuberculosis
<220> FEATURE:
<223> OTHER INFORMATION: Tb475 cDNA
<221> NAME/KEY: modified_base
<222> LOCATION: (1)..(1704)
<223> OTHER INFORMATION: n = g, a, c or t

<400> SEQUENCE: 8

```
cgcgatcgtc gtcaacgang tcgaccgtca ccacggactg atcaacaagt tcgcaggcga        60
cgccgccctg gccatcttcg gagccccgaa ccgcctcgac cgtcccgaag acgccgcgct       120
ggccgccgcc cgggccatan ccgancggct ggccnacgag atgcccgagg tccaagccgg      180
catcggggtg gcgcaggcc anatcgtcgc cggcaatgtc ggcgccaagc aaagattcna       240
atacacagtg gtcggcaagc cggtcaacca ngcggcccga ttgtgcgaac tggccaaatc      300
acaccccgcg cgattgggtc tcgcccgctc ggctcatggt cacccaattc aaggactact      360
ttggcctggc gcacgacctg ccgaagtggg cgagtgaagg cgccaaagcc gccggtgagg      420
```

```
ccgccaaggc gttgccggcc gccgttccgg ccattccgag tgctggcctg agcggcgttg      480
cgggcgccgt cggtcaggcg gcgtcggtcg ggggattgaa ggttccggcc gtttggaccg      540
ccacgacccc ggcggcgagc cccgcggtgc tggcggcgtc caacggcctc ggagccgcgg      600
ccgccgctga aggttcgaca cacgcgtttg gcgggatgcc gctcatgggt ancggtgccg      660
gacgtgcgtt taacaacttc gctgcccctc gatacggatt caagccgacc gtgatcgccc      720
aaccgccggc tggcggatga ccaactacgt tcgttgatcg aggatcgaat tcnacgattc      780
aaagggagga attcatatga cctcncgttt tatgacggat ccgcacgcna tncgggacat      840
ggcgggccgt tttgaggtgc acgcccagac ggtggaggac gaggctngcn ggatgtgggc      900
gtccgcgcaa aacatttccg gtgcgggctg gagtggcatg gccgaggcga cctcgntaga      960
caccatggcc cagatgaatc aggcgtttcn caacatcgtg aacatgctgc acggggtgng     1020
tgacgggctg gttcgcgacg ccaacaacta cgaacagcaa gagcaggcct cccagcagat     1080
cctcagcagc tgacccggcc cgacgactca ggaggacaca tgaccatcaa ctatcaattc     1140
ggggacgtcg acgctcatgg cgccatgatc cgcgctntgg ccgggttgct ggaggccgag     1200
catcaggcca tcatttctga tgtgttgacc gcgagtgact tttggggcgg cgccggttcg     1260
gcggcctgcc aggggttcat tacccagttg ggccgtaact tccaggtgat ttacgagcag     1320
gccaacgccc acgggcagaa ggtgcaggct gccggcaaca acatggcaca aaccgacagc     1380
gccgtnggnt ccagctgggc ctaacccggg tcntaagttg ggtccgcgca gggcgggccg     1440
atcagcgtng actttggcgc ccgatacacg ggcatnttnt ngtcgggaac actgcgcccg     1500
cgtcagntgc ccgcttcccc ttgttnggcg acgtgctcgg tgatggcttt gacgaccgct     1560
tcgccggcgc ggccaatcaa ttggtcgcgc ttgcctntag cccattcgtg cgacgcccgc     1620
ggcgccgcga gttgtccctt gaaataagga atcacagcac gggcgaacag ctcataggag     1680
tgaaaggttg ccgtggcggg gccc                                            1704
```

<210> SEQ ID NO 9
<211> LENGTH: 2286
<212> TYPE: DNA
<213> ORGANISM: Mycobacterium tuberculosis
<220> FEATURE:
<223> OTHER INFORMATION: Tb488 cDNA
<221> NAME/KEY: modified_base
<222> LOCATION: (1)..(2286)
<223> OTHER INFORMATION: n = g, a, c or t

<400> SEQUENCE: 9

```
ccgtcttggc gtctgggcgc attgtgatct gggccanttg cccctccacc cagaccgcgc       60
ccagcttgtc gatccagccc gcgacccgga ttgccaccgc gcgaaccggg aacggattct      120
ccgctgaatt ctgggtcact tcgcagtcgc gcgggtgatc ctgttggcga ncagcgtctg      180
gaacgggcgt cnaacgcgtg ccgtaagccc agcgtgtacg ccgtcagccc gacgccgatg      240
ccgaatgcct tgccgcccaa gctgagccgc gcgggctcca ccaagagcgt cacggtgagc      300
cagccaacca gatgcaaggc gacgatcacc gcgaagtgcc gaattcggca cgagaggtgc      360
tggaaatcca gcaatacgcc cgcgagccga tctcgttgga ccagaccatc ggcgacgang      420
gcgacagnca gcttggcgat ttcatcgaaa acagcgaggc ggtggtggnc gtcgacgcgg      480
tgtccttcac tttgctgcat gatcaactgc antcggtgct ggacacgctc tccgagcgtg      540
aggcgggcgt ggtgcggcta cgcttcggcc ttaccgacgg ccagccgcgc acccttgacg      600
agatcggcca ggtctacggc gtgacccggg aacgcatccg ccagatcgaa tccaagacta      660
```

| | |
|---|---|
| tgtcgaagtt gcgccatccg agccgctcac aggtcctgcg cgactatcgt gccgaattcg | 720 |
| gcacgagccg ttttgaggtg cacgcccaga cggtggagga cgaggctcgc cggatgtggg | 780 |
| cgtccgcgca aaacatttcc ggtgcgggct ggagtggcat ggccgangcg acctcgctag | 840 |
| acaccatggc ccagatgaat caggcgtttc gcaacatcgt gaacatgctg cacggggtgc | 900 |
| gtgacgggct ggttcgcgac gccaacaact acgaacagca agagcaggcc tcccagcaga | 960 |
| tcctcagcag ctgacccggc ccgacgactc aggaggacac atgaccatca actatcaatt | 1020 |
| cggggacgtc gacgctcatg gcgccatgat ccgcgctctg gccgggttgc tggaggccga | 1080 |
| gcatcaggcc atcatttctg atgtgttgac cgcgagtgac ttttgggggcg cgccggttc | 1140 |
| ggcggcctgc caggggttca ttacccagtt gggccgtaac ttccaggtga tctacgagca | 1200 |
| ggccaacgcc cacgggcaga aggtgcaggc tgccggcaac aacatggcac aaaccgacag | 1260 |
| cgccgtcggc tccagctggg cctaacccgg gtcctaagtt gggtccgcgc agggcgggcc | 1320 |
| gatcagcgtc gactttggcg cccgatacac gggcatgtng tngtcgggaa cactgcgccc | 1380 |
| gcgtcagctg cccgcttccc cttgttcggc gacgtgctcg gtgatggctt tgacgaccgc | 1440 |
| ttcgccggcg cggccaatca attggtcgcg cttgcctcta gcctcgtgcc gaattcggca | 1500 |
| cgagggtgct ggtgccgcgc tatcggcagc acgtgagctc cacgacgaac tcatcccagt | 1560 |
| gctgggttcc gcggagttcg gcatcggcgt gtcggccgga agggccatcg ccggccacat | 1620 |
| cggcgctcaa gcccgcttcg agtacaccgt catcggcgac ccggtcaacg aggccgcccg | 1680 |
| gctcaccgaa ctggccaaag tcgaggatgg ccacgttctg cgtcggcga tcgcggtcag | 1740 |
| tggcgccctg gacgccgaag cattgtgttg ggatgttggc gaggtggttg agctccgcgg | 1800 |
| acgtgctgca cccacccaac tagccaggcc aatgaatntg gcngcacccg aagaggtttc | 1860 |
| cagcgaagta cgcggctagt cgcgcttggc tgcnttcttc gccggcacct tccgggcagc | 1920 |
| tttcctggct ggccgttttg ccggaccccg ggctcggcga tcggccaaca gctcggcggc | 1980 |
| gcgctcgtcg gttatggaag ccacgtngtc gcccttacgc aggctggcat tggtctcacc | 2040 |
| gtcggtgacg tacggcccga atcggccgtc cttgatgacc attggcttgc cagacgccgg | 2100 |
| atntgntccc agctcgcgca gcggcggagc cgaagcgctt tgccggccac gacnttcgg | 2160 |
| ctctgngtag atnttcaggg cttcgtcgag cgngatggtg aatatatggt cttcggtgac | 2220 |
| cagtgatcga gaatcgttgc cgcgctttag atacggtcng tagcgcccgt tctgcgcggt | 2280 |
| gatntc | 2286 |

<210> SEQ ID NO 10
<211> LENGTH: 1136
<212> TYPE: DNA
<213> ORGANISM: Mycobacterium tuberculosis
<220> FEATURE:
<223> OTHER INFORMATION: Tb465 cDNA
<221> NAME/KEY: modified_base
<222> LOCATION: (1)..(1136)
<223> OTHER INFORMATION: n = g, a, c or t

<400> SEQUENCE: 10

| | |
|---|---|
| gggcatcttc cccgaccgcg cctcgatcat ccgcctcgtc ggagccgtcc tcgccgaaca | 60 |
| acacgacgaa tggatcgaag gacggcgcta cctgggcctc gaggtcctca cccgagcccg | 120 |
| agcagcactg accagcaccg aagaaccgcc aagcagcaaa ccaccaacac cccagcactg | 180 |
| accacctaga ctgccacccg aaggatcacg cgaggaacct tcactcgtac accacgtccc | 240 |
| tggccttggc ctggtgtcag gcccagctgg agccgacggc gctgtcggtt tgcgccatgt | 300 |

-continued

```
tgttgccggc agcctgcacc ttctgcccgt gggcgttggc ctgctcgtag atcacctgga      360
agttacggcc caactgggta atgaacccct ggcaggccgc cgaaccggcg ccgccccaaa      420
agtcactcgc ggtcaacaca tcacgaatga tggcctgatg ctcggcctcc agcaacccgg      480
cctgagcgcg gatcatggcg ccgtgagcgt cgacatcacc gaactgatag ttgatggtca      540
tcgaacctgt tctccttcgc ttgtaaaagt attgtgctgc agcggctgac gttagctgct      600
gaggatctgc tgggaggcct gctcttgcct cgtgccgaat cggcacgag aggccgcctt       660 cgaagaaatc cttttgagaat tcgccaaggc cgtcgaccca gcatgggtc agctcgccag      720 ccgcgccggc tggcaaccgt tcccgctcga gaaagacctg gaggaatacc agtgacaaac      780
gacctcccag acgtccgaga gcgtgacggc ggtccacgtc ccgctcctcc tgctggcggg      840
ccacgcttgt cagacgtgtg ggtttacaac gggcggcgt acgacctgag tgagtggatt       900
tccaagcatc ccggcggcgc cttnttcatt gggcggacca agaaccgcga catcaccgca      960
atcgtcaagt cctaccatcg tgatccggcg attgtcgagc gaatcctgca gcggaggtac     1020
gcgttgggcc gcgacgcaac ccctagggac atccacccca agcacaatgc accggcattt    1080
ctgttcaaag acgacttcaa cagctggcgg gacaccccga agtatcgatt ngacga         1136
```

<210> SEQ ID NO 11
<211> LENGTH: 967
<212> TYPE: DNA
<213> ORGANISM: Mycobacterium tuberculosis
<220> FEATURE:
<223> OTHER INFORMATION: Tb431 cDNA
<221> NAME/KEY: modified_base
<222> LOCATION: (1)..(967)
<223> OTHER INFORMATION: n = g, a, c or t

<400> SEQUENCE: 11

```
tgagcgccaa ccctaccgtc ggttcgtcac acggaccgca tggcctgctc cgcggactgc       60
cgctagggtc gcggatcact cggcgtagcg gcgccttttgc ccaccgatat gggttccgtc     120
acagtgtggt tgcccgcccg ccatcggccg gataacgcca tgacctcagc tcggcagaaa     180
tgacaatgct cccaaaggcg tgagcacccg aagacaacta agcaggagat cgcatgccgt     240
ttgtgactac ccaaccagaa gcactggcgg cggcggccgg cagtctgcag ggaatcggct     300
ccgcattgaa cgcccagaat gcggctgcgg cgactcccac gacggggtg gtccggcggc      360 cgccgatgaa ntgtcggcgc tgacggcggc tcagttcgcg gcacacgccc agatctatca    420
ggccgtcagc gcccaggccg cggcgattca cgagatgttc gtcaacactc tacagatgag    480
ctcagggtcg tatgctgcta ccgaggccgc caacgcggcc gcggccggnt agaggagtca    540
ctgcgatgga ttttggggcg ttgccgccgg aggtcaattc ggtgcggatg tatgccgttc    600
ctggctcggc accaatggtc gctgcggcgt cggcctggaa cgggttggcc gcggagctga    660
gttcggcggc caccggttat gagacggtga tcactcagct cagcagtgag gggtggctag    720
gtccggcgtc agcggcgatg gccgaggcag ttgcgccgta tgtggcgtgg atgagtgccg    780
ctgcggcgca agccgagcag gcggccacac aggccagggc cgccgcggcc gcttttgagg    840
cggcgtttgc cgcgacggtg cctccgccgt tgatcgcggc caaccgggct tcgttgatgc    900
agctgatctc gacgaatgtc tttggtcaga acacctcggc gatcgcggcc gccgaagctc    960
agtacgg                                                              967
```

<210> SEQ ID NO 12
<211> LENGTH: 585

-continued

```
<212> TYPE: DNA
<213> ORGANISM: Mycobacterium tuberculosis
<220> FEATURE:
<223> OTHER INFORMATION: Tb472 cDNA

<400> SEQUENCE: 12
tggattccga tagcggtttc ggcccctcga cgggcgacca cggcgcgcag gcctccgaac      60
ggggggccgg gacgctggga ttcgccggga ccgcaaccaa agaacgccgg gtccgggcgg     120
tcgggctgac cgcactggcc ggtgatgagt tcggcaacgg cccccggatg ccgatggtgc     180
cggggacctg ggagcagggc agcaacgagc ccgaggcgcc cgacggatcg gggagagggg     240
gaggcgacgg cttaccgcac gacagcaagt aaccgaattc cgaatcacgt ggacccgtac     300
gggtcgaaag gagagatgtt atgagccttt tggatgctca tatcccacag ttggtggcct     360
cccagtcggc gtttgccgcc aaggcggggc tgatgcggca cacgatcggt caggccgagc     420
aggcggcgat gtcggctcag gcgtttcacc agggggagtc gtcggcggcg tttcaggccg     480
cccatgcccg gtttgtggcg gcggccgcca aagtcaacac cttgttggat gtcgcgcagg     540
cgaatctggg tgaggccgcc ggtacctatg tggccgccga tgctg                    585

<210> SEQ ID NO 13
<211> LENGTH: 144
<212> TYPE: PRT
<213> ORGANISM: Mycobacterium tuberculosis
<220> FEATURE:
<223> OTHER INFORMATION: Tb224
<221> NAME/KEY: MOD_RES
<222> LOCATION: (1)..(144)
<223> OTHER INFORMATION: Xaa = any amino acid

<400> SEQUENCE: 13

Ala Leu Val Thr Thr Asn Phe Phe Gly Val Asn Thr Ile Pro Ile Ala
  1               5                  10                  15

Leu Asn Glu Ala Asp Tyr Leu Arg Met Trp Ile Gln Ala Ala Thr Val
             20                  25                  30

Met Ser His Tyr Gln Ala Val Ala His Glu Ile Trp Cys Leu His Glu
         35                  40                  45

Xaa Ala Ser Ser Gly Lys Pro Trp Ala Ser Ile Thr Thr Gly Ala Pro
     50                  55                  60

Gly Ser Pro Ala Ser Thr Thr Arg Ser Arg Thr Pro Leu Val Ser Thr
 65                  70                  75                  80

Asn Arg Xaa Val Xaa Ala Pro Ile Val Ser Pro Asn His Thr Gly His
                 85                  90                  95

Arg Pro Glu Lys Gly Leu Gly Ser Xaa Gln Arg Arg Leu Ser Arg Val
            100                 105                 110

Leu Pro Arg Ile Ile Asp Arg Pro Ala Gly Pro Xaa Gly Pro Pro Leu
        115                 120                 125

Thr Ser Gly Ser His Phe Leu Cys Ser Trp His Gly Tyr Ser Ser Gln
    130                 135                 140

<210> SEQ ID NO 14
<211> LENGTH: 352
<212> TYPE: PRT
<213> ORGANISM: Mycobacterium tuberculosis
<220> FEATURE:
<223> OTHER INFORMATION: Tb636
<221> NAME/KEY: MOD_RES
<222> LOCATION: (60)
<223> OTHER INFORMATION: Xaa = any amino acid

<400> SEQUENCE: 14
```

His Ala Leu Ala Ala Gln Tyr Thr Glu Ile Ala Thr Glu Leu Ala Ser
 1               5                  10                  15

Val Leu Ala Ala Val Gln Ala Ser Ser Trp Gln Gly Pro Ser Ala Asp
             20                  25                  30

Arg Phe Val Ala His Gln Pro Phe Arg Tyr Trp Leu Thr His Ala
         35                  40                  45

Ala Thr Val Ala Thr Ala Ala Ala Ala His Xaa Thr Ala Ala Ala
     50                  55                  60

Gly Tyr Thr Ser Ala Leu Gly Gly Met Pro Thr Leu Ala Glu Leu Ala
 65              70                  75                  80

Ala Asn His Ala Met His Gly Ala Leu Val Thr Thr Asn Phe Phe Gly
                 85                  90                  95

Val Asn Thr Ile Pro Ile Ala Leu Asn Glu Ala Asp Tyr Leu Arg Met
             100                 105                 110

Trp Ile Gln Ala Ala Thr Val Met Ser His Tyr Gln Ala Val Ala His
         115                 120                 125

Glu Ser Val Ala Ala Thr Pro Ser Thr Pro Ala Pro Gln Ile Val
130                 135                 140

Thr Ser Ala Ala Ser Ser Ala Ala Ser Ser Phe Pro Asp Pro Thr
145                 150                 155                 160

Lys Leu Ile Leu Gln Leu Leu Lys Asp Phe Leu Glu Leu Leu Arg Tyr
                 165                 170                 175

Leu Ala Val Glu Leu Leu Pro Gly Pro Leu Gly Asp Leu Ile Ala Gln
             180                 185                 190

Val Leu Asp Trp Phe Ile Ser Phe Val Ser Gly Pro Val Phe Thr Phe
         195                 200                 205

Leu Ala Tyr Leu Val Leu Asp Pro Leu Ile Tyr Phe Gly Pro Phe Ala
     210                 215                 220

Pro Leu Thr Ser Pro Val Leu Leu Pro Ala Val Glu Leu Arg Asn Arg
225                 230                 235                 240

Leu Lys Thr Ala Thr Gly Leu Thr Leu Pro Pro Thr Val Ile Phe Asp
                 245                 250                 255

His Pro Thr Pro Thr Ala Val Ala Glu Tyr Val Ala Gln Gln Met Ser
             260                 265                 270

Gly Ser Arg Pro Thr Glu Ser Gly Asp Pro Thr Ser Gln Val Val Glu
         275                 280                 285

Pro Ala Arg Ala Glu Phe Gly Thr Ser Ala Val His Gln Ile Pro Pro
     290                 295                 300

Arg Pro Ala Asp Thr Arg Arg Ala Cys Arg His Arg Asp Asp Val Pro
305                 310                 315                 320

Arg Asp Ser Arg Ile Ala Gln His Arg Asp Gly Ala Gly Leu Asp Pro
                 325                 330                 335

Thr Glu Arg Gly Thr Ser Glu Gly Asp Gln Gly Leu Val Ser Gly Trp
             340                 345                 350

<210> SEQ ID NO 15
<211> LENGTH: 141
<212> TYPE: PRT
<213> ORGANISM: Mycobacterium tuberculosis
<220> FEATURE:
<223> OTHER INFORMATION: Tb431

<400> SEQUENCE: 15

Met Asp Phe Gly Ala Leu Pro Pro Glu Val Asn Ser Val Arg Met Tyr
 1               5                  10                  15

-continued

```
Ala Val Pro Gly Ser Ala Pro Met Val Ala Ala Ser Ala Trp Asn
            20                  25                  30
Gly Leu Ala Ala Glu Leu Ser Ser Ala Ala Thr Gly Tyr Glu Thr Val
        35                  40                  45
Ile Thr Gln Leu Ser Ser Glu Gly Trp Leu Gly Pro Ala Ser Ala Ala
    50                  55                  60
Met Ala Glu Ala Val Ala Pro Tyr Val Ala Trp Met Ser Ala Ala Ala
65                  70                  75                  80
Ala Gln Ala Glu Gln Ala Ala Thr Gln Ala Arg Ala Ala Ala Ala
                85                  90                  95
Phe Glu Ala Ala Phe Ala Ala Thr Val Pro Pro Leu Ile Ala Ala
            100                 105                 110
Asn Arg Ala Ser Leu Met Gln Leu Ile Ser Thr Asn Val Phe Gly Gln
            115                 120                 125
Asn Thr Ser Ala Ile Ala Ala Glu Ala Gln Tyr Gly
        130                 135                 140
```

<210> SEQ ID NO 16
<211> LENGTH: 58
<212> TYPE: PRT
<213> ORGANISM: Mycobacterium tuberculosis
<220> FEATURE:
<223> OTHER INFORMATION: Tc424 ORF-1

<400> SEQUENCE: 16

```
Met Ala Ser Arg Phe Met Thr Asp Pro His Ala Met Arg Asp Met Ala
1               5                   10                  15
Gly Arg Phe Glu Val His Ala Gln Thr Val Glu Asp Glu Ala Arg Arg
            20                  25                  30
Met Trp Ala Ser Ala Gln Asn Ile Ser Gly Ala Gly Trp Ser Gly Met
        35                  40                  45
Ala Glu Ala Thr Ser Leu Asp Thr Met Thr
    50                  55
```

<210> SEQ ID NO 17
<211> LENGTH: 67
<212> TYPE: PRT
<213> ORGANISM: Mycobacterium tuberculosis
<220> FEATURE:
<223> OTHER INFORMATION: Tb424 ORF-2

<400> SEQUENCE: 17

```
Met Thr Ile Asn Tyr Gln Phe Gly Asp Val Asp Ala His Gly Ala Met
1               5                   10                  15
Ile Arg Ala Gln Ala Ala Ser Leu Glu Ala Glu His Gln Ala Ile Val
            20                  25                  30
Arg Asp Val Leu Ala Ala Gly Asp Phe Trp Gly Gly Ala Gly Ser Val
        35                  40                  45
Ala Cys Gln Glu Phe Ile Thr Gln Leu Gly Arg Asn Phe Gln Val Ile
    50                  55                  60
Tyr Glu Gln
65
```

<210> SEQ ID NO 18
<211> LENGTH: 58
<212> TYPE: PRT
<213> ORGANISM: Mycobacterium tuberculosis
<220> FEATURE:
<223> OTHER INFORMATION: Tb436 ORF-1

-continued

```
<400> SEQUENCE: 18

Met Ala Ser Arg Phe Met Thr Asp Pro His Ala Met Arg Asp Met Ala
 1               5                  10                  15

Gly Arg Phe Glu Val His Ala Gln Thr Val Glu Asp Glu Ala Arg Arg
             20                  25                  30

Met Trp Ala Ser Ala Gln Asn Ile Ser Gly Ala Gly Trp Ser Gly Met
         35                  40                  45

Ala Glu Ala Thr Ser Leu Asp Thr Met Thr
     50                  55

<210> SEQ ID NO 19
<211> LENGTH: 94
<212> TYPE: PRT
<213> ORGANISM: Mycobacterium tuberculosis
<220> FEATURE:
<223> OTHER INFORMATION: Tb436 ORF-2

<400> SEQUENCE: 19

Met Thr Ile Asn Tyr Gln Phe Gly Asp Val Asp Ala His Gly Ala Met
 1               5                  10                  15

Ile Arg Ala Gln Ala Ala Ser Leu Glu Ala Glu His Gln Ala Ile Val
             20                  25                  30

Arg Asp Val Leu Ala Ala Gly Asp Phe Trp Gly Gly Ala Gly Ser Val
         35                  40                  45

Ala Cys Gln Glu Phe Ile Thr Gln Leu Gly Arg Asn Phe Gln Val Ile
     50                  55                  60

Tyr Glu Gln Ala Asn Ala His Gly Gln Lys Val Gln Ala Ala Gly Asn
 65                  70                  75                  80

Asn Met Ala Gln Thr Asp Ser Ala Val Gly Ser Ser Trp Ala
                 85                  90

<210> SEQ ID NO 20
<211> LENGTH: 30
<212> TYPE: PRT
<213> ORGANISM: Mycobacterium tuberculosis
<220> FEATURE:
<223> OTHER INFORMATION: Tb398 ORF-1

<400> SEQUENCE: 20

Asn Met Leu His Gly Val Arg Asp Gly Leu Val Arg Asp Ala Asn Asn
 1               5                  10                  15

Tyr Glu Gln Gln Glu Gln Ala Ser Gln Gln Ile Leu Ser Ser
             20                  25                  30

<210> SEQ ID NO 21
<211> LENGTH: 94
<212> TYPE: PRT
<213> ORGANISM: Mycobacterium tuberculosis
<220> FEATURE:
<223> OTHER INFORMATION: Tb398 ORF-2

<400> SEQUENCE: 21

Met Thr Ile Asn Tyr Gln Phe Gly Asp Val Asp Ala His Gly Ala Met
 1               5                  10                  15

Ile Arg Ala Gln Ala Gly Leu Leu Glu Ala Glu His Gln Ala Ile Ile
             20                  25                  30

Arg Asp Val Leu Thr Ala Ser Asp Phe Trp Gly Gly Ala Gly Ser Ala
         35                  40                  45

Ala Cys Gln Gly Phe Ile Thr Gln Leu Gly Arg Asn Phe Gln Val Ile
```

```
                  50                  55                  60
Tyr Glu Gln Ala Asn Ala His Gly Gln Lys Val Gln Ala Ala Gly Asn
 65                  70                  75                  80

Asn Met Ala Gln Thr Asp Ser Ala Val Gly Ser Ser Trp Ala
                 85                  90

<210> SEQ ID NO 22
<211> LENGTH: 69
<212> TYPE: PRT
<213> ORGANISM: Mycobacterium tuberculosis
<220> FEATURE:
<223> OTHER INFORMATION: Tb508 ORF-1

<400> SEQUENCE: 22

Ala Arg Arg Met Trp Ala Ser Ala Gln Asn Ile Ser Gly Ala Gly Trp
  1               5                  10                  15

Ser Gly Met Ala Glu Ala Thr Ser Leu Asp Thr Met Ala Gln Met Asn
                 20                  25                  30

Gln Ala Phe Arg Asn Ile Val Asn Met Leu His Gly Val Arg Asp Gly
             35                  40                  45

Leu Val Arg Asp Ala Asn Asn Tyr Glu Gln Gln Glu Gln Ala Ser Gln
         50                  55                  60

Gln Ile Leu Ser Ser
 65

<210> SEQ ID NO 23
<211> LENGTH: 94
<212> TYPE: PRT
<213> ORGANISM: Mycobacterium tuberculosis
<220> FEATURE:
<223> OTHER INFORMATION: Tb508 ORF-2
<221> NAME/KEY: MOD_RES
<222> LOCATION: (90)
<223> OTHER INFORMATION: Xaa = any amino acid

<400> SEQUENCE: 23

Met Thr Ile Asn Tyr Gln Phe Gly Asp Val Asp Ala His Gly Ala Met
  1               5                  10                  15

Ile Arg Ala Gln Ala Gly Leu Leu Glu Ala Glu His Gln Ala Ile Ile
                 20                  25                  30

Arg Asp Val Leu Thr Ala Ser Asp Phe Trp Gly Gly Ala Gly Ser Ala
             35                  40                  45

Ala Cys Gln Gly Phe Ile Thr Gln Leu Gly Arg Asn Phe Gln Val Ile
         50                  55                  60

Tyr Glu Gln Ala Asn Thr His Gly Gln Lys Val Gln Ala Ala Gly Asn
 65                  70                  75                  80

Asn Met Ala Gln Thr Asp Ser Ala Val Xaa Ser Ser Trp Ala
                 85                  90

<210> SEQ ID NO 24
<211> LENGTH: 52
<212> TYPE: PRT
<213> ORGANISM: Mycobacterium tuberculosis
<220> FEATURE:
<223> OTHER INFORMATION: Tb441 ORF-1
<221> NAME/KEY: MOD_RES
<222> LOCATION: (1)..(52)
<223> OTHER INFORMATION: Xaa = any amino acid

<400> SEQUENCE: 24

Gly Met Ala Glu Ala Thr Ser Xaa Asp Thr Met Thr Gln Met Asn Gln
  1               5                  10                  15
```

Ala Phe Arg Asn Ile Val Asn Met Leu His Gly Val Arg Asp Gly Leu
            20                  25                  30

Val Arg Asp Ala Asn Xaa Tyr Glu Gln Gln Glu Gln Ala Ser Gln Gln
        35                  40                  45

Ile Leu Ser Ser
    50

<210> SEQ ID NO 25
<211> LENGTH: 94
<212> TYPE: PRT
<213> ORGANISM: Mycobacterium tuberculosis
<220> FEATURE:
<223> OTHER INFORMATION: Tb441 ORF-2
<221> NAME/KEY: MOD_RES
<222> LOCATION: (64)
<223> OTHER INFORMATION: Xaa = any amino acid

<400> SEQUENCE: 25

Met Thr Ile Asn Tyr Gln Phe Gly Asp Val Asp Ala His Gly Ala Met
 1               5                  10                  15

Ile Arg Ala Gln Ala Gly Ser Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Xaa
    50                  55                  60

Tyr Glu Gln Ala Asn Ala His Gly Gln Lys Val Gln Ala Ala Gly Asn
 65                  70                  75                  80

Asn Met Ala Gln Thr Asp Ser Ala Val Gly Ser Ser Trp Ala
                85                  90

<210> SEQ ID NO 26
<211> LENGTH: 98
<212> TYPE: PRT
<213> ORGANISM: Mycobacterium tuberculosis
<220> FEATURE:
<223> OTHER INFORMATION: Tb475 ORF-1

<400> SEQUENCE: 26

Met Thr Ser Arg Phe Met Thr Asp Pro His Ala Met Arg Asp Met Ala
 1               5                  10                  15

Gly Arg Phe Glu Val His Ala Gln Thr Val Glu Asp Glu Ala Arg Arg
            20                  25                  30

Met Trp Ala Ser Ala Gln Asn Ile Ser Gly Ala Gly Trp Ser Gly Met
        35                  40                  45

Ala Glu Ala Thr Ser Leu Asp Thr Met Ala Gln Met Asn Gln Ala Phe
    50                  55                  60

Arg Asn Ile Val Asn Met Leu His Gly Val Arg Asp Gly Leu Val Arg
 65                  70                  75                  80

Asp Ala Asn Asn Tyr Glu Gln Gln Glu Gln Ala Ser Gln Gln Ile Leu
                85                  90                  95

Ser Ser

<210> SEQ ID NO 27
<211> LENGTH: 94
<212> TYPE: PRT
<213> ORGANISM: Mycobacterium tuberculosis
<220> FEATURE:
<223> OTHER INFORMATION: Tb475 ORF-2
<221> NAME/KEY: MOD_RES

```
<222> LOCATION: (20)
<223> OTHER INFORMATION: Xaa = any amino acid

<400> SEQUENCE: 27

Met Thr Ile Asn Tyr Gln Phe Gly Asp Val Asp Ala His Gly Ala Met
1               5                   10                  15

Ile Arg Ala Xaa Ala Gly Leu Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
                85                  90

<210> SEQ ID NO 28
<211> LENGTH: 81
<212> TYPE: PRT
<213> ORGANISM: Mycobacterium tuberculosis
<220> FEATURE:
<223> OTHER INFORMATION: Tb488 ORF-1
<221> NAME/KEY: MOD_RES
<222> LOCATION: (33)
<223> OTHER INFORMATION: Xaa = any amino acid

<400> SEQUENCE: 28

Arg Phe Glu Val His Ala Gln Thr Val Glu Asp Glu Ala Arg Arg Met
1               5                   10                  15

Trp Ala Ser Ala Gln Asn Ile Ser Gly Ala Gly Trp Ser Gly Met Ala
            20                  25                  30

Xaa Ala Thr Ser Leu Asp Thr Met Ala Gln Met Asn Gln Ala Phe Arg
        35                  40                  45

Asn Ile Val Asn Met Leu His Gly Val Arg Asp Gly Leu Val Arg Asp
    50                  55                  60

Ala Asn Asn Tyr Glu Gln Gln Glu Gln Ala Ser Gln Gln Ile Leu Ser
65                  70                  75                  80

Ser

<210> SEQ ID NO 29
<211> LENGTH: 94
<212> TYPE: PRT
<213> ORGANISM: Mycobacterium tuberculosis
<220> FEATURE:
<223> OTHER INFORMATION: Tb488 ORF-2

<400> SEQUENCE: 29

Met Thr Ile Asn Tyr Gln Phe Gly Asp Val Asp Ala His Gly Ala Met
1               5                   10                  15

Ile Arg Ala Leu Ala Gly Leu Leu Glu Ala Glu His Gln Ala Ile Ile
            20                  25                  30

Ser Asp Val Leu Thr Ala Ser Asp Phe Trp Gly Gly Ala Gly Ser Ala
        35                  40                  45

Ala Cys Gln Gly Phe Ile Thr Gln Leu Gly Arg Asn Phe Gln Val Ile
    50                  55                  60

Tyr Glu Gln Ala Asn Ala His Gly Gln Lys Val Gln Ala Ala Gly Asn
65                  70                  75                  80

Asn Met Ala Gln Thr Asp Ser Ala Val Gly Ser Ser Trp Ala
```

-continued

```
<210> SEQ ID NO 30
<211> LENGTH: 11
<212> TYPE: PRT
<213> ORGANISM: Mycobacterium tuberculosis
<220> FEATURE:
<223> OTHER INFORMATION: Tb465 ORF-1

<400> SEQUENCE: 30

Gln Glu Gln Ala Ser Gln Gln Ile Leu Ser Ser
 1               5                  10

<210> SEQ ID NO 31
<211> LENGTH: 94
<212> TYPE: PRT
<213> ORGANISM: Mycobacterium tuberculosis
<220> FEATURE:
<223> OTHER INFORMATION: Tb465 ORF-2

<400> SEQUENCE: 31

Met Thr Ile Asn Tyr Gln Phe Gly Asp Val Asp Ala His Gly Ala Met
 1               5                  10                  15

Ile Arg Ala Gln Ala Gly Leu Leu Glu Ala Glu His Gln Ala Ile Ile
                20                  25                  30

Arg Asp Val Leu Thr Ala Ser Asp Phe Trp Gly Gly Ala Gly Ser Ala
            35                  40                  45

Ala Cys Gln Gly Phe Ile Thr Gln Leu Gly Arg Asn Phe Gln Val Ile
        50                  55                  60

Tyr Glu Gln Ala Asn Ala His Gly Gln Lys Val Gln Ala Ala Gly Asn
 65                  70                  75                  80

Asn Met Ala Gln Thr Asp Ser Ala Val Gly Ser Ser Trp Ala
                85                  90

<210> SEQ ID NO 32
<211> LENGTH: 99
<212> TYPE: PRT
<213> ORGANISM: Mycobacterium tuberculosis
<220> FEATURE:
<223> OTHER INFORMATION: Tb424 ORF-U

<400> SEQUENCE: 32

Met Ser Phe Val Thr Thr Gln Pro Glu Ala Leu Ala Ala Ala Ala Ala
 1               5                  10                  15

Asn Leu Gln Gly Ile Gly Thr Thr Met Asn Ala Gln Asn Ala Ala Ala
                20                  25                  30

Ala Ala Pro Thr Thr Gly Val Val Pro Ala Ala Ala Asp Glu Val Ser
            35                  40                  45

Ala Leu Thr Ala Ala Gln Phe Ala Ala His Gln Met Tyr Gln Thr
        50                  55                  60

Val Ser Ala Gln Ala Ala Ala Ile His Glu Met Phe Val Asn Thr Leu
 65                  70                  75                  80

Val Ala Ser Ser Gly Ser Tyr Ala Ala Thr Glu Ala Ala Asn Ala Ala
                85                  90                  95

Ala Ala Gly

<210> SEQ ID NO 33
<211> LENGTH: 99
<212> TYPE: PRT
<213> ORGANISM: Mycobacterium tuberculosis
<220> FEATURE:
```

<223> OTHER INFORMATION: Tb436 ORF-U

<400> SEQUENCE: 33

Met Ser Phe Val Thr Thr Gln Pro Glu Ala Leu Ala Ala Ala Ala Ala
1               5                   10                  15

Asn Leu Gln Gly Ile Gly Thr Thr Met Asn Ala Gln Asn Ala Ala Ala
            20                  25                  30

Ala Ala Pro Thr Thr Gly Val Val Pro Ala Ala Asp Glu Val Ser
        35                  40                  45

Ala Leu Thr Ala Ala Gln Phe Ala Ala His Ala Gln Met Tyr Gln Thr
    50                  55                  60

Val Ser Ala Gln Ala Ala Ala Ile His Glu Met Phe Val Asn Thr Leu
65                  70                  75                  80

Val Ala Ser Ser Gly Ser Tyr Ala Ala Thr Glu Ala Ala Asn Ala Ala
                85                  90                  95

Ala Ala Gly

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-1

<400> SEQUENCE: 34

Asp Pro His Ala Met Arg Asp Met Ala Gly Arg Phe Glu Val His
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-2

<400> SEQUENCE: 35

Arg Asp Met Ala Gly Arg Phe Glu Val His Ala Gln Thr Val Glu
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-3

<400> SEQUENCE: 36

Arg Phe Glu Val His Ala Gln Thr Val Glu Asp Glu Ala Arg Arg
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-4

<400> SEQUENCE: 37

Ala Gln Thr Val Glu Asp Glu Ala Arg Arg Met Trp Ala Ser Ala
1               5                   10                  15

-continued

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence:peptide
    ORF-1-5

<400> SEQUENCE: 38

Asp Glu Ala Arg Arg Met Trp Ala Ser Ala Gln Asn Ile Ser Gly
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence:peptide
    ORF-1-6

<400> SEQUENCE: 39

Met Trp Ala Ser Ala Gln Asn Ile Ser Gly Ala Gly Trp Ser Gly
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence:peptide
    ORF-1-7

<400> SEQUENCE: 40

Gln Asn Ile Ser Gly Ala Gly Trp Ser Gly Met Ala Glu Ala Thr
 1               5                  10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence:peptide
    ORF-1-8

<400> SEQUENCE: 41

Ala Gly Trp Ser Gly Met Ala Glu Ala Thr Ser Leu Asp Thr Met Thr
 1               5                  10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence:peptide
    ORF-1-9

<400> SEQUENCE: 42

Met Ala Glu Ala Thr Ser Leu Asp Thr Met Ala Gln Met Asn Gln
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence:peptide
    ORF-1-10

```
<400> SEQUENCE: 43

Ser Leu Asp Thr Met Ala Gln Met Asn Gln Ala Phe Arg Asn Ile
 1               5                  10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-11

<400> SEQUENCE: 44

Ala Gln Met Asn Gln Ala Phe Arg Asn Ile Val Asn Met Leu His
 1               5                  10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-12

<400> SEQUENCE: 45

Ala Phe Arg Asn Ile Val Asn Met Leu His Gly Val Arg Asp Gly
 1               5                  10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-13

<400> SEQUENCE: 46

Val Asn Met Leu His Gly Val Arg Asp Gly Leu Val Arg Asp Ala
 1               5                  10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-14

<400> SEQUENCE: 47

Gly Val Arg Asp Gly Leu Val Arg Asp Ala Asn Asn Tyr Glu Gln
 1               5                  10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence:peptide
      ORF-1-15

<400> SEQUENCE: 48

Leu Val Arg Asp Ala Asn Asn Tyr Glu Gln Gln Glu Gln Ala Ser
 1               5                  10                  15

<210> SEQ ID NO 49
<211> LENGTH: 16
```

```
<212> TYPE: PRT
<213> ORGANISM: Artificial Sequence
<220> FEATURE:
<223> OTHER INFORMATION: Description of Artificial Sequence:peptide
      ORF-1-16

<400> SEQUENCE: 49

Asn Asn Tyr Glu Gln Gln Glu Gln Ala Ser Gln Gln Ile Leu Ser Ser
 1               5                  10                  15

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence:peptide
      ORF-1-17

<400> SEQUENCE: 50

Met Ala Ser Arg Phe Met Thr Asp Pro His Ala Met Arg Asp Met Ala
 1               5                  10                  15

Gly

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-1

<400> SEQUENCE: 51

Met Thr Ile Asn Tyr Gln Phe Gly Asp Val Asp Ala His Gly Ala
 1               5                  10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-2

<400> SEQUENCE: 52

Gln Phe Gly Asp Val Asp Ala His Gly Ala Met Ile Arg Ala Gln
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-3

<400> SEQUENCE: 53

Asp Ala His Gly Ala Met Ile Arg Ala Gln Ala Ala Ser Leu Glu
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-4

<400> SEQUENCE: 54
```

```
Met Ile Arg Ala Gln Ala Ala Ser Leu Glu Ala Glu His Gln Ala
 1               5                  10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-5

<400> SEQUENCE: 55

Ala Ala Ser Leu Glu Ala Glu His Gln Ala Ile Val Arg Asp Val
 1               5                  10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-6

<400> SEQUENCE: 56

Ala Glu His Gln Ala Ile Val Arg Asp Val Leu Ala Ala Gly Asp
 1               5                  10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-7

<400> SEQUENCE: 57

Ile Val Arg Asp Val Leu Ala Ala Gly Asp Phe Trp Gly Gly Ala
 1               5                  10                  15

<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence:peptide
      ORF-2-8

<400> SEQUENCE: 58

Leu Ala Ala Gly Asp Phe Trp Gly Gly Ala Gly Ser Val Ala Cys Gln
 1               5                  10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-9

<400> SEQUENCE: 59

Phe Trp Gly Gly Ala Gly Ser Val Ala Cys Gln Glu Phe Ile Thr
 1               5                  10                  15

<210> SEQ ID NO 60
<211> LENGTH: 15
<212> TYPE: PRT
<213> ORGANISM: Artificial Sequence
```

```
<220> FEATURE:
<223> OTHER INFORMATION: Description of Artificial Sequence:peptide
      ORF-2-10

<400> SEQUENCE: 60

Gly Ser Val Ala Cys Gln Glu Phe Ile Thr Gln Leu Gly Arg Asn
 1               5                  10                  15

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence:peptide
      ORF-2-11

<400> SEQUENCE: 61

Gln Glu Phe Ile Thr Gln Leu Gly Arg Asn Phe Gln Val Ile Tyr Glu
 1               5                  10                  15

Gln Ala

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-12

<400> SEQUENCE: 62

Arg Asn Phe Gln Val Ile Tyr Glu Gln Ala Asn Ala His Gly Gln
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-13

<400> SEQUENCE: 63

Ile Tyr Glu Gln Ala Asn Ala His Gly Gln Lys Val Gln Ala Ala
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-14

<400> SEQUENCE: 64

Asn Ala His Gly Gln Lys Val Gln Ala Ala Gly Asn Asn Met Ala
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-15

<400> SEQUENCE: 65

Lys Val Gln Ala Ala Gly Asn Asn Met Ala Gln Thr Asp Ser Ala
```

```
<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence:peptide
      ORF-2-16

<400> SEQUENCE: 66

Gly Asn Asn Met Ala Gln Thr Asp Ser Ala Val Gly Ser Ser Trp Ala
 1               5                  10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-17

<400> SEQUENCE: 67

Asp Ala His Gly Ala Met Ile Arg Ala Leu Ala Gly Leu Leu Glu
 1               5                  10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-18

<400> SEQUENCE: 68

Asp Ala His Gly Ala Met Ile Arg Ala Gln Ala Gly Leu Leu Glu
 1               5                  10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-19

<400> SEQUENCE: 69

Met Ile Arg Ala Leu Ala Gly Leu Leu Glu Ala Glu His Gln Ala
 1               5                  10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-20

<400> SEQUENCE: 70

Met Ile Arg Ala Gln Ala Gly Leu Leu Glu Ala Glu His Gln Ala
 1               5                  10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence:peptide
```

```
        ORF-2-21

<400> SEQUENCE: 71

Ala Gly Leu Leu Glu Ala Glu His Gln Ala Ile Ile Ser Asp Val
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence:peptide
        ORF-2-22

<400> SEQUENCE: 72

Ala Gly Leu Leu Glu Ala Glu His Gln Ala Ile Ile Arg Asp Val
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence:peptide
        ORF-2-23

<400> SEQUENCE: 73

Ala Glu His Gln Ala Ile Ile Ser Asp Val Leu Thr Ala Ser Asp
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence:peptide
        ORF-2-24

<400> SEQUENCE: 74

Ala Glu His Gln Ala Ile Ile Arg Asp Val Leu Thr Ala Ser Asp
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence:peptide
        ORF-2-25

<400> SEQUENCE: 75

Ile Ile Ser Asp Val Leu Thr Ala Ser Asp Phe Trp Gly Gly Ala
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence:peptide
        ORF-2-26

<400> SEQUENCE: 76

Ile Ile Arg Asp Val Leu Thr Ala Ser Asp Phe Trp Gly Gly Ala
1               5                   10                  15

<210> SEQ ID NO 77
```

```
<211> LENGTH: 16
<212> TYPE: PRT
<213> ORGANISM: Artificial Sequence
<220> FEATURE:
<223> OTHER INFORMATION: Description of Artificial Sequence:peptide
      ORF-2-27

<400> SEQUENCE: 77

Leu Thr Ala Ser Asp Phe Trp Gly Gly Ala Gly Ser Ala Ala Cys Gln
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-28

<400> SEQUENCE: 78

Phe Trp Gly Gly Ala Gly Ser Ala Ala Cys Gln Gly Phe Ile Thr
 1               5                  10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-29

<400> SEQUENCE: 79

Gly Ser Ala Ala Cys Gln Gly Phe Ile Thr Gln Leu Gly Arg Asn
 1               5                  10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence:peptide
      ORF-2-30

<400> SEQUENCE: 80

Gln Gly Phe Ile Thr Gln Leu Gly Arg Asn Phe Gln Val Ile Tyr
 1               5                  10                  15

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence:overlapping
      peptide of open reading frame of Tb224

<400> SEQUENCE: 81

Val Thr Thr Asn Phe Phe Gly Val Asn Thr Ile Pro Ile Ala Leu Asn
 1               5                  10                  15

Glu Ala Asp Tyr Leu Arg Met Trp Ile
                20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence:overlapping
      peptide of open reading frame of Tb224
```

<400> SEQUENCE: 82

Asn Glu Ala Asp Tyr Leu Arg Met Trp Ile Gln Ala Ala Thr Val Met
 1               5                  10                  15

Ser His Tyr Gln Ala Val Ala His Glu
            20                  25

<210> SEQ ID NO 83
<211> LENGTH: 967
<212> TYPE: DNA
<213> ORGANISM: Mycobacterium tuberculosis
<220> FEATURE:
<223> OTHER INFORMATION: full-length Tb431 cDNA containing ORF encoding
      Mtb-40
<221> NAME/KEY: modified_base
<222> LOCATION: (1)..(967)
<223> OTHER INFORMATION: n = g, a, c or t

<400> SEQUENCE: 83

| | | | | |
|---|---|---|---|---|
| tgagcgccaa | ccctaccgtc | ggttcgtcac | acggaccgca | tggcctgctc cgcggactgc | 60 |
| cgctagggtc | gcggatcact | cggcgtagcg | gcgcctttgc | ccaccgatat gggttccgtc | 120 |
| acagtgtggt | tgcccgcccg | ccatcggccg | gataacgcca | tgacctcagc tcggcagaaa | 180 |
| tgacaatgct | cccaaaggcg | tgagcacccg | aagacaacta | gcaggagat cgcatgccgt | 240 |
| tgtgactac | ccaaccagaa | gcactggcgg | cggcggccgg | cagtctgcag ggaatcggct | 300 |
| ccgcattgaa | cgcccagaat | gcggctgcgg | cgactcccac | gacggggtg gtccggcggc | 360 |
| cgccgatgaa | ntgtcggcgc | tgacggcggc | tcagttcgcg | gcacacgccc agatctatca | 420 |
| ggccgtcagc | gcccaggccg | cggcgattca | cgagatgttc | gtcaacactc tacagatgag | 480 |
| ctcagggtcg | tatgctgcta | ccgaggccgc | caacgcggcc | gcggccggnt agaggagtca | 540 |
| ctgcgatgga | ttttggggcg | ttgccgccgg | aggtcaattc | ggtgcggatg tatgccgttc | 600 |
| ctggctcggc | accaatggtc | gctgcggcgt | cggcctggaa | cgggttggcc gcggagctga | 660 |
| gttcggcggc | caccggttat | gagacggtga | tcactcagct | cagcagtgag gggtggctag | 720 |
| gtccggcgtc | agcggcgatg | gccgaggcag | ttgcgccgta | tgtggcgtgg atgagtgccg | 780 |
| ctgcggcgca | agccgagcag | gcggccacac | aggccagggc | cgccgcggcc gcttttgagg | 840 |
| cggcgtttgc | cgcgacggtg | cctccgccgt | tgatcgcggc | caaccgggct tcgttgatgc | 900 |
| agctgatctc | gacgaatgtc | tttggtcaga | acacctcggc | gatcgcggcc gccgaagctc | 960 |
| agtacgg | | | | | 967 |

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence:peptide
      MSF-1

<400> SEQUENCE: 84

Met Ser Phe Val Thr Thr Gln Pro Glu Ala Leu Ala Ala Ala Ala
 1               5                  10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence:peptide
      MSF-2

-continued

```
<400> SEQUENCE: 85

Thr Gln Pro Glu Ala Leu Ala Ala Ala Ala Asn Leu Gln Gly
 1               5                  10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence:peptide
      MSF-3

<400> SEQUENCE: 86

Leu Ala Ala Ala Ala Ala Asn Leu Gln Gly Ile Gly Thr Thr Met
 1               5                  10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence:peptide
      MSF-4

<400> SEQUENCE: 87

Ala Asn Leu Gln Gly Ile Gly Thr Thr Met Asn Ala Gln Asn Ala
 1               5                  10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence:peptide
      MSF-5

<400> SEQUENCE: 88

Ile Gly Thr Thr Met Asn Ala Gln Asn Ala Ala Ala Ala Ala Pro
 1               5                  10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence:peptide
      MSF-6

<400> SEQUENCE: 89

Asn Ala Gln Asn Ala Ala Ala Ala Ala Pro Thr Thr Gly Val Val
 1               5                  10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence:peptide
      MSF-7

<400> SEQUENCE: 90

Ala Ala Ala Ala Pro Thr Thr Gly Val Val Pro Ala Ala Ala Asp
 1               5                  10                  15

<210> SEQ ID NO 91
<211> LENGTH: 15
```

```
<212> TYPE: PRT
<213> ORGANISM: Artificial Sequence
<220> FEATURE:
<223> OTHER INFORMATION: Description of Artificial Sequence:peptide
      MSF-8

<400> SEQUENCE: 91

Thr Thr Gly Val Val Pro Ala Ala Ala Asp Glu Val Ser Ala Leu
 1               5                  10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence:peptide
      MSF-9

<400> SEQUENCE: 92

Pro Ala Ala Ala Asp Glu Val Ser Ala Leu Thr Ala Ala Gln Phe
 1               5                  10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence:peptide
      MSF-10

<400> SEQUENCE: 93

Glu Val Ser Ala Leu Thr Ala Ala Gln Phe Ala Ala His Ala Gln
 1               5                  10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence:peptide
      MSF-11

<400> SEQUENCE: 94

Thr Ala Ala Gln Phe Ala Ala His Ala Gln Met Tyr Gln Thr Val
 1               5                  10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence:peptide
      MSF-12

<400> SEQUENCE: 95

Ala Ala His Ala Gln Met Tyr Gln Thr Val Ser Ala Gln Ala Ala
 1               5                  10                  15

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence:peptide
      MSF-13

<400> SEQUENCE: 96

Met Tyr Gln Thr Val Ser Ala Gln Ala Ala Ala Ile His Glu Met Phe
```

```
                    1               5              10              15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence:peptide
      MSF-14

<400> SEQUENCE: 97

Ser Ala Gln Ala Ala Ala Ile His Glu Met Phe Val Asn Thr Leu
 1               5                  10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence:peptide
      MSF-15

<400> SEQUENCE: 98

Ala Ile His Glu Met Phe Val Asn Thr Leu Val Ala Ser Ser Gly
 1               5                  10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence:peptide
      MSF-16

<400> SEQUENCE: 99

Phe Val Asn Thr Leu Val Ala Ser Ser Gly Ser Tyr Ala Ala Thr
 1               5                  10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence:peptide
      MSF-17

<400> SEQUENCE: 100

Val Ala Ser Ser Gly Ser Tyr Ala Ala Thr Glu Ala Ala Asn Ala
 1               5                  10                  15

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence:peptide
      MSF-18

<400> SEQUENCE: 101

Ser Tyr Ala Ala Thr Glu Ala Ala Asn Ala Ala Ala Ala Gly
 1               5                  10

<210> SEQ ID NO 102
<211> LENGTH: 1784
<212> TYPE: DNA
<213> ORGANISM: Mycobacterium tuberculosis
<220> FEATURE:
<223> OTHER INFORMATION: Tb867 cDNA
```

<221> NAME/KEY: modified_base
<222> LOCATION: (1)..(1784)
<223> OTHER INFORMATION: n = g, a, c or t

<400> SEQUENCE: 102

| | | | | | |
|---|---|---|---|---|---|
| attcgttcct | gccgcagcta | aatcccgggg | acatcgtcgc | cggccagtac | gaggtcaaag | 60 |
| gctgcatcgc | gcacggcgga | ctgggctgga | tctacctcgc | tctcgaccgc | aatgtcaacg | 120 |
| gccgtccggt | ggtgctcaag | ggcctggtgc | attccgtga | tgccgaagcg | caggcaatgg | 180 |
| cgatggccga | acgccagttc | ctggccgagg | tggtgcaccc | gtcgatcgtg | cagatcttca | 240 |
| actttgtcga | gcacaccgac | aggcacgggg | atccggtcgg | ctacatcgtg | atggaatacg | 300 |
| tcggcgggca | atcgctcaaa | cgcagcaagg | gtcanaaact | gcccgtcgcg | gaggccatcg | 360 |
| cctacctgct | ggagatcctg | ccggcgctga | gctacctgca | ttccatcggc | ttggtctaca | 420 |
| acgacctgaa | gccggaaaac | atcatgctga | ccgaggaaca | gctcaagctg | atcgacctgg | 480 |
| gcgcggtatc | gcggatcaac | tcgttcggct | acctctacgg | gacccaggc | ttccaggcgc | 540 |
| ccgagatcgt | gcggaccggt | ccgacggtgg | ccaccgacat | ctacaccgtg | ggacgcacgc | 600 |
| tcgcggcgct | cacgctggac | ctgcccaccc | gcaatggccg | ttatgtggat | gggctacccg | 660 |
| aagacgaccc | ggtgctgaaa | acctacgact | cttacggccg | gttgctgcgc | agggccatcg | 720 |
| accccgatcc | gcggcaacgg | ttcaccaccc | cgaagagat | gtccgcgcaa | ttgacgggcg | 780 |
| tgttgcggga | ggtggtcgcc | cagacaccgg | ggtgccgcgg | ccaggctatc | aacgatcttc | 840 |
| agtcccagtc | ggtcgacatt | tggagtggac | tgctggtggc | gcacaccgac | gtgtatctgg | 900 |
| acgggcaggt | gcacgcggag | aagctgaccg | ccaacgagat | cgtgaccgcg | ctgtcggtgc | 960 |
| cgctggtcga | tccgaccgac | gtcgcagctt | cggtcctgca | ggccacgtg | ctctcccagc | 1020 |
| cggtgcagac | cctagactcg | ntgcgcgcgg | cccgccacgg | tgcgctggac | gccgacggcg | 1080 |
| tcgattntcc | gagtcagtgg | agctgccgct | aatggaagtc | cgcgcgctgc | tggatctcgg | 1140 |
| cgatgtggcc | aaggccaccc | gaaaactcga | cgatctggcc | gaacgcgttg | gctggcgatg | 1200 |
| gcgattggtc | tggtaccggg | ccgtcgccga | gctgctcacc | ggcgactatg | actcggccac | 1260 |
| caaacatttc | accgaggtgc | tggataccttt | tcccggcgag | ctggcgccca | agctcgccct | 1320 |
| ggccgccacc | gccgaactag | ccggcaacac | cgacgaacac | aagttctatc | agacggtgtg | 1380 |
| gagcaccaac | gacggcgtga | tctcggcggc | tttcggactg | gccagagccc | ggtcggccga | 1440 |
| aggtgatcgg | gtcggcgccg | tgcgcacgct | cgacgaggta | ccgcccactt | ctcggcattt | 1500 |
| caccacggca | cggctgacca | gcgcggtgac | tctgttgtcc | ggccggtcaa | cgagtgaagt | 1560 |
| caccgaggaa | cagatccgcg | acgccgcccg | aagagtggag | gcgctgcccc | cgaccgaacc | 1620 |
| acgcgtgctg | cagatccgcg | ccctggtgct | gggtggcgcg | ctggactggc | tgaaggacaa | 1680 |
| caaggccagc | accaaccaca | tcctcggttt | cccgttcacc | agtcacgggc | tgcggctggg | 1740 |
| tgtcgaggcg | tcactgcgca | gcctggcccg | ggtagctccc | actc | | 1784 |

<210> SEQ ID NO 103
<211> LENGTH: 766
<212> TYPE: DNA
<213> ORGANISM: Mycobacterium tuberculosis
<220> FEATURE:
<223> OTHER INFORMATION: Tb391 cDNA
<221> NAME/KEY: modified_base
<222> LOCATION: (1)..(766)
<223> OTHER INFORMATION: n = g, a, c or t

<400> SEQUENCE: 103

-continued

| | |
|---|---|
| acaaracact cggyggckgc cgmtccggcc tgatcgtcgg tgatcagcyt cgtgccaaay | 60 |
| tcggcacaag gtgcgcgctr cccaangagt tcttcgccgc rgtgcgmgcm kaactggcct | 120 |
| atcntggttg ggtgccgtcc cgcanaaccc gcgaacttaa acccattta accgggcagg | 180 |
| aagtttccta catytacccn rgsmanccaa ccgggccgcc nanaamtccg tcctggantc | 240 |
| cgancggttc ccgtgttcg ccgcactgct gaccggcacg gartatccgc aggcggcgtt | 300 |
| ggccaacgcg tgggtgcaac tggcctacgg tgcgcaccas gacgccatca ccggctcgga | 360 |
| gtccgaccag gtactcaatg ctggcgacca ccagccag cagaccaaac tggtgcacgc | 420 |
| cgatctccga gcgcgccggc ccggtggcat acggattggt cgaaaccaat ccgaaggaat | 480 |
| tcatcacgga cggtcacgga aaacgatcgc cccaatgggn ggacnacccn agccaggcgn | 540 |
| attnaccgtt naacaagttg gngtaggttc tttgatatcg akcaaccgat acggakcggm | 600 |
| ccgcggaatg gtagaccacc accagtgccc ncamgtmgtg caccagttg gtcatcgccc | 660 |
| gcagatcggt gaccccgcca agcgttccgg atgcggagat gasggtgacc agccyggttg | 720 |
| acctgttgat caggttntcc cagtgccacg tcggcagctg gccggt | 766 |

<210> SEQ ID NO 104
<211> LENGTH: 1231
<212> TYPE: DNA
<213> ORGANISM: Mycobacterium tuberculosis
<220> FEATURE:
<223> OTHER INFORMATION: Tb470 cDNA
<221> NAME/KEY: modified_base
<222> LOCATION: (1)..(1231)
<223> OTHER INFORMATION: n = g, a, c or t

<400> SEQUENCE: 104

| | |
|---|---|
| cggcacgaga atgtcgcctg tgcctcgata gccacttgcg tgtggtcgcg ctgccagcgg | 60 |
| gtcagccagg tcgcctggtc caggccatcg ggccggcgca ggagcgcgat gttggccaga | 120 |
| cccggtgtac gagaaccgga ctcgacnaag tgtcggcgct gacggcggct cagttcgcgg | 180 |
| cacacgccca gatctatcag gccgtcagcg cccaggccgc ggcgattcac gagatgttcg | 240 |
| tcaacactct acagatnanc tcagggtcgt atgctgctac cgaggccgcc aacgcggccg | 300 |
| cggccggcta gaggagtcac tgcgatggat tttgggcgt tgccgccgga ggtcaattcg | 360 |
| gtgcggatgt atgccggtcc tggctcggca ccaatggtcg ctgcggcgtc ggcctggaac | 420 |
| gggttggccg cggagctgag ttcggcggcc accggttatg agacggtgat cactcagctc | 480 |
| agcagtgagg ggtggctagg tccggcgtca gcggcgatgg ccgaggcagt tgcgccgtat | 540 |
| gtggcgtgga tgagtgccgc tgcggcgcaa gccgagcagg cggccacaca ggccagggcc | 600 |
| gccgcggcc cttttgaggc ggcgtttgcc gcgacggtgc ctccgccgtt gatcgcggcc | 660 |
| aaccgggctt cgttgatgca gctgatctcg acgaatgtct ttggtcagaa cacctcggcg | 720 |
| atcgcggccg ccgaagctca gtacggcgag atgtgggccc aagactccgc ggcgatgtat | 780 |
| gcctacgcgg gcagttcggc gagcgcctcg gcggtcacgc cgtttagcac gccgccgcag | 840 |
| attgccaacc cgaccgctca gggtacgcag gccgcggccg tggccaccgc cgccggtacc | 900 |
| gcccagtcga cgctgacgga gatgatcacc gggctaccca acgcgctgca aagcctcacc | 960 |
| tcacntctgt tgcagtcgtc taacggtccg ctgtcgtggc tgtggcagat cttgttcggc | 1020 |
| acgcccaatt tccccacctc aatttcggca ctgctgaccg acctgcagcc ctacgcgagc | 1080 |
| ttnttntata acaccgaggg cctgccgtac ttcagcatcg gcatgggcaa caacttcatt | 1140 |
| cagtcggcca agaccctggg attgatcggc taggcggcac cggctgcggt cgcggnntgct | 1200 |

-continued ggggatnccg ccaagggctt gcctcgtgcc g          1231

<210> SEQ ID NO 105
<211> LENGTH: 2041
<212> TYPE: DNA
<213> ORGANISM: Mycobacterium tuberculosis
<220> FEATURE:
<223> OTHER INFORMATION: Tb838 cDNA
<221> NAME/KEY: modified_base
<222> LOCATION: (1)..(2041)
<223> OTHER INFORMATION: n = g, a, c or t

<400> SEQUENCE: 105
cggcacgagc tcgtgccgat cagtgccatt gacggcttgt acgaccttct ggggattgga      60
atacccaacc aagggggtat cctttactcc tcactagagt acttcgaaaa agccctggag     120
gagctggcag cagcgtttcc gggtgatggc tggttaggtt cggccgcgga caaatacgcc     180
ggcaaaaacc gcaaccacgt gaattttttc caggaactgg cagacctcga tcgtcagctc     240
atcagcctga tccacgacca ggccaacgcg gtccagacga cccgcgacat cctggagggc     300
gccaagaaag gtctcgagtt cgtgcgcccg gtggctgtgg acctgaccta catcccggtc     360
gtcgggcacg ccctatcggc cgccttccan gcgccgtttt gcgcgggcgc gatggccgta     420
gtgggcggcg cgcttgccta cttggtcgtg aaaacgctga tcaacgcgac tcaactcctc     480
aaattgcttg ccaaattggc ggagttggtc gcggccgcca ttgcggacat catttcggat     540
gtggcggaca tcatcaaggg catcctcgga gaagtgtggg agttcatcac aaacgcgctc     600
aacggcctga agagctttg gacaagctc acggggtggg tgaccggact gttctctcga     660
gggtggtcga acctggagtc cttctttgcg ggcgtccccg gcttgaccgg cgcgaccagc     720
ggcttgtcgc aagtgactgg cttgttcggt gcggccggtc tgtccgcatc gtcgggcttg     780
gctcacgcgg atagcctggc gagctcagcc agcttgcccg ccctggccgg cattgggggc     840
gggtccggtt ttgggggctt gccgagcctg gctcaggtcc atgccgcctc aactcggcag     900
gcgctacggc cccgagctga tggcccggtc ggcgccgctg ccgagcaggt cggcgggcag     960
tcgcagctgt ctccgcgca gggttcccaa ggtatgggcg acccgtagg catgggcggc    1020
atgcacccct cttcggggc gtcgaaaggg acgacgacga agaagtactc ggaaggcgcg    1080
gcggcgggca ctgaagacgc cgagcgcgcg ccagtcgaag ctgacgcggg cggtgggcaa    1140
aaggtgctgg tacgaaacgt cgtctaacgg catggcgagc caaatccatt gctagccagc    1200
gcctaacaac gcgcaatgct aaacggaagg gacacgatca atgacggaaa acttgaccgt    1260
ccagcccgag cgtctcggtg tactggcgtc gcaccatgac aacgcggcgg tcgatgcntc    1320
ctcgggcgtc gaagctgccg ctggcctagg cgaatctgtg gcgatcactc acggtccgta    1380
ctgctcacag ttcaacgaca cgttaaatgt gtacttgact gcccacaatg ccctgggctc    1440
gtccttgcat acggccggtg tcgatctcgc caaaagtctt cgaattgcgg cgaagatata    1500
tagcgaggcc gacgaagcgt ggcgcaaggc tatcgacggg ttgtttacct gaccacgttt    1560
gctgcccgca gtgcaggcca cgacgtagcg caggtcgtgt ccctcgtagg cgtggatgcg    1620
accggccagc accagcaccc ggtgcgcacc gatgggcacg acagtagct cgcccgcatg    1680
cccggctgcg gttggcggca caaacccggg cagttcggcc tgcggcagca cggtggtngg    1740
ggagcccaac gccgcaacgg ccggtaacca tcccgacccg agcacgaccg agacgtcatg    1800
ttcgccgatc ccggtgcggt cagcgatgac ctgcgccgcc cgccgggcca gtttgtcggg    1860
atcggggcgc gggtcagcca cactgggcga gcttaactga gccgctcgcc ggggagcggg    1920

| | |
|---|---|
| tgctngtcga tgagatactg cgagcatgcc agcagccagc gcatccgacc gcgtcgagga | 1980 |
| attggtgcgg cgccgtggtg gcgagctggt cgagctgtcc catgccatcc acctcgtgcc | 2040 |
| g | 2041 |

<210> SEQ ID NO 106
<211> LENGTH: 1202
<212> TYPE: DNA
<213> ORGANISM: Mycobacterium tuberculosis
<220> FEATURE:
<223> OTHER INFORMATION: Tb962 cDNA
<221> NAME/KEY: modified_base
<222> LOCATION: (984)
<223> OTHER INFORMATION: n = g, a, c or t

<400> SEQUENCE: 106

| | |
|---|---|
| gagctcaccg ctatcaacca atactttctg cactccaaga tgcaggacaa ctggggtttt | 60 |
| accgagctgg cggcccacac ccgcgcggag tcgttcgacg aaatgcggca cgccgaggaa | 120 |
| atcaccgatc gcatcttgtt gctggatggt ttgccgaact accagcgcat cggttcgttg | 180 |
| cgtatcggcc agacgctccg cgagcaattt gaggccgatc tggcgatcga atacgacgtg | 240 |
| ttgaatcgtc tcaagccagg aatcgtcatg tgccgggaga acaggacac caccagcgcc | 300 |
| gtactgctgg agaaaatcgt tgccgacgag gaagaacaca tcgactactt ggaaacgcag | 360 |
| ctggagctga tggacaagct aggagaggag ctttactcgg cgcagtgcgt ctctcgccca | 420 |
| ccgacctgat gcccgcttga ggattctccg ataccactcc gggcgccgct gacaagctct | 480 |
| agcatcgact cgaacagcga tgggagggcg gatatggcgg ccccacagc accgaccact | 540 |
| gcccccaccg caatccgagc cggtggcccg ctgctcagtc cggtgcgacg caacattatt | 600 |
| ttcaccgcac ttgtgttcgg ggtgctggtc gctgcgaccg gccaaaccat cgttgtgccc | 660 |
| gcattgccga cgatcgtcgc cgagctgggc agcaccgttg accagtcgtg ggcggtcacc | 720 |
| agctatctgc tgggggggaac actskygkkk ktgkkgksks ksrmrmkctc ggtgatctgc | 780 |
| tcggccgcaa cagggtgctg ctaggctccg tcgtggtctt cgtcgttggc tctgtgctgt | 840 |
| gcgggttatc gcagacgatg accatgctgg cgatctctcg cgcactgcag ggcgtcggtg | 900 |
| ccggtgcgat ttccgtcacc gcctacgcgc tggccgctga ggtggtccca ctgcgggacc | 960 |
| gtggccgcta ccaggcgtc ttangtgcgg tgttcggtgt caacacggtc accggtccgc | 1020 |
| tgctgggggg ctggctcacc gactatctga gctggcggtg ggcgttccga ccaccagccc | 1080 |
| catcaccgac ccgatcgcgg tcatcgcggc gaacaccgcc ctcgcggcgt gcgggcagg | 1140 |
| tcccttgggg aacgtggtcc cacagcgcca gaacggtcgg aaatgcgatg ccgacccac | 1200 |
| ac | 1202 |

<210> SEQ ID NO 107
<211> LENGTH: 496
<212> TYPE: DNA
<213> ORGANISM: Mycobacterium tuberculosis
<220> FEATURE:
<223> OTHER INFORMATION: Tb962 cDNA
<221> NAME/KEY: modified_base
<222> LOCATION: (1)..(496)
<223> OTHER INFORMATION: n = g, a, c or t

<400> SEQUENCE: 107

| | |
|---|---|
| ggcggcggca gttggccagc agttngggcg ggggagccgg ttcggngacc aagaaatcgg | 60 |
| cctgggcaag cagccgggac cgcgnaccgt gatcagttng gatcgccggg accgccgccg | 120 |
| accaangcca ttccgccgnt gaggaagtcg gaantntgcg cagtgatgac gccctgctgc | 180 |

-continued

```
aacgcntccc ggattgccga gcggatcgcc gccgaacggc ggtgctcacc accggcgagc      240 accccctacng acaggcccgc atagctgaat gacgccgggt naccgccgtc ccntccaccg      300
nganatcggc ccggangcaa agatccgtc ggcgctccgc ctcggcgacg acagccacgt       360
tcacccgcgc gttatcggtg ccgcgatcg cataccaggc gccgtcaagg tngccgtygc       420
ggtagtcacg caccgacaag gtgatytggt ccatcgcctn gacggcgggg gtgacgctgg      480
gggcgatcam gtgcac                                                      496
```

<210> SEQ ID NO 108
<211> LENGTH: 849
<212> TYPE: DNA
<213> ORGANISM: Mycobacterium tuberculosis
<220> FEATURE:
<223> OTHER INFORMATION: full-length Tb472 cDNA
<221> NAME/KEY: modified_base
<222> LOCATION: (1)..(849)
<223> OTHER INFORMATION: n = g, a, c or t

<400> SEQUENCE: 108

```
tggattccga tagcggtttc ggcccctcga cgggcgacca cggcgcgcag gcctccgaac       60
ggggggccgg gacgctggga ttcgccggga ccgcaaccaa agaacgccgg gtccgggcgg      120
tcgggctgac cgcactggcc ggtgatgagt tcggcaacgg ccccggatg ccgatggtgc       180 cggggacctg ggagcagggc agcaacgagc ccgaggcgcc cgacggatcg gggagagggg      240
gaggcgacgg cttaccgcac gacagcaagt aaccgaattc cgaatcacgt ggacccgtac      300
gggtcgaaag gagagatgtt atgagccttt tggatgctca tatcccacag ttggtggcct      360
cccagtcggc gtttgccgcc aaggcggggc tgatgcggca cacgatcggt caggccgagc      420
aggcggcgat gtcggctcag gcgtttcacc aggggagtc gtcggcggcg tttcaggccg      480
cccatgcccg gtttgtggcg gcggccgcca aagtcaacac cttgttggat gtcgcgcagg      540
cgaatctggg tgaggccgcc ggtacctatg tggccgccga tgctgcggcc gcgtcgacct      600
ataccgggtt ctgatcgaac cctgctgacc gagaggactt gtgatgtcgc aaatcatgta      660
caactacccc gcgatgttgg gtcacgccgg ggatatggcc ggatatgccg gcacgctgca      720
gagcttgggt gccgagatcg ccgtggagca ggccgcgttg cagagtgcgt ggcagggcga      780
taccgggatc acgtatcagg cgtggcaggc acantggtaa ccangccang gaagatttgg      840
tgcgggcct                                                             849
```

<210> SEQ ID NO 109
<211> LENGTH: 97
<212> TYPE: PRT
<213> ORGANISM: Mycobacterium tuberculosis
<220> FEATURE:
<223> OTHER INFORMATION: Tb472 (MSL)

<400> SEQUENCE: 109

```
Met Ser Leu Leu Asp Ala His Ile Pro Gln Leu Val Ala Ser Gln Ser
 1               5                  10                  15

Ala Phe Ala Ala Lys Ala Gly Leu Met Arg His Thr Ile Gly Gln Ala
             20                  25                  30

Glu Gln Ala Ala Met Ser Ala Gln Ala Phe His Gln Gly Glu Ser Ser
         35                  40                  45

Ala Ala Phe Gln Ala Ala His Ala Arg Phe Val Ala Ala Ala Ala Lys
     50                  55                  60

Val Asn Thr Leu Leu Asp Val Ala Gln Ala Asn Leu Gly Glu Ala Ala
```

```
           65                  70                  75                  80
Gly Thr Tyr Val Ala Asp Ala Ala Ala Ser Thr Tyr Thr Gly
                85                  90                  95
Phe

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence:peptide
      MSL-1

<400> SEQUENCE: 110

Met Ser Leu Leu Asp Ala His Ile Pro Gln Leu Val Ala Ser Gln
 1               5                  10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence:peptide
      MSL-2

<400> SEQUENCE: 111

Ala His Ile Pro Gln Leu Val Ala Ser Gln Ser Ala Phe Ala Ala
 1               5                  10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence:peptide
      MSL-3

<400> SEQUENCE: 112

Leu Val Ala Ser Gln Ser Ala Phe Ala Ala Lys Ala Gly Leu Met
 1               5                  10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence:peptide
      MSL-4

<400> SEQUENCE: 113

Ser Ala Phe Ala Ala Lys Ala Gly Leu Met Arg His Thr Ile Gly
 1               5                  10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence:peptide
      MSL-5

<400> SEQUENCE: 114

Lys Ala Gly Leu Met Arg His Thr Ile Gly Gln Ala Glu Gln Ala
 1               5                  10                  15

<210> SEQ ID NO 115
```

-continued

```
<211> LENGTH: 15
<212> TYPE: PRT
<213> ORGANISM: Artificial Sequence
<220> FEATURE:
<223> OTHER INFORMATION: Description of Artificial Sequence:peptide
      MSL-6

<400> SEQUENCE: 115

Arg His Thr Ile Gly Gln Ala Glu Gln Ala Ala Met Ser Ala Gln
 1               5                  10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence:peptide
      MSL-7

<400> SEQUENCE: 116

Gln Ala Glu Gln Ala Ala Met Ser Ala Gln Ala Phe His Gln Gly
 1               5                  10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence:peptide
      MSL-8

<400> SEQUENCE: 117

Ala Met Ser Ala Gln Ala Phe His Gln Gly Glu Ser Ser Ala Ala
 1               5                  10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence:peptide
      MSL-9

<400> SEQUENCE: 118

Ala Phe His Gln Gly Glu Ser Ser Ala Ala Phe Gln Ala Ala His
 1               5                  10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence:peptide
      MSL-10

<400> SEQUENCE: 119

Glu Ser Ser Ala Ala Phe Gln Ala Ala His Ala Arg Phe Val Ala
 1               5                  10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence:peptide
      MSL-11

<400> SEQUENCE: 120
```

Phe Gln Ala Ala His Ala Arg Phe Val Ala Ala Ala Lys Val
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence:peptide
      MSL-12

<400> SEQUENCE: 121

Ala Arg Phe Val Ala Ala Ala Lys Val Asn Thr Leu Leu Asp
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence:peptide
      MSL-13

<400> SEQUENCE: 122

Ala Ala Ala Lys Val Asn Thr Leu Leu Asp Val Ala Gln Ala Asn
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence:peptide
      MSL-14

<400> SEQUENCE: 123

Asn Thr Leu Leu Asp Val Ala Gln Ala Asn Leu Gly Glu Ala Ala
1               5                   10                  15

<210> SEQ ID NO 124
<211> LENGTH: 18
<212> TYPE: PRT
<213> ORGANISM: Artificial Sequence
<220> FEATURE:
<223> OTHER INFORMATION: Description of Artificial Sequence:peptide
      MSL-15

<400> SEQUENCE: 124

Val Ala Gln Ala Asn Leu Gly Glu Ala Ala Gly Thr Tyr Val Ala Ala
1               5                   10                  15

Asp Ala

<210> SEQ ID NO 125
<211> LENGTH: 1752
<212> TYPE: DNA
<213> ORGANISM: Mycobacterium tuberculosis
<220> FEATURE:
<223> OTHER INFORMATION: full-length open reading frame of Tb470
      (Mtb-40)
<221> NAME/KEY: modified_base
<222> LOCATION: (1)..(1752)
<223> OTHER INFORMATION: n = g, a, c or t

<400> SEQUENCE: 125
cggcacgaga atgtcgcctg tgcctcgata gccacttgcg tgtggtcgcg ctgccagcgg      60
gtcagccagg tcgcctggtc caggccatcg ggccggcgca ggagcgcgat gttggccaga     120

-continued

```
cccggtgtac gagaaccgga ctcgacnaag tgtcggcgct gacggcggct cagttcgcgg    180
cacacgccca gatctatcag gccgtcagcg cccaggccgc ggcgattcac gagatgttcg    240
tcaacactct acagatnanc tcagggtcgt atgctgctac cgaggccgcc aacgcggccg    300
cggccggcta gaggagtcac tgcgatggat tttgggcgt tgccgccgga ggtcaattcg     360
gtgcggatgt atgccggtcc tggctcggca ccaatggtcg ctgcggcgtc ggcctggaac    420
gggttggccg cggagctgag ttcggcggcc accggttatg agacggtgat cactcagctc    480
agcagtgagg ggtggctagg tccggcgtca gcggcgatgg ccgaggcagt tgcgccgtat    540
gtggcgtgga tgagtgccgc tgcggcgcaa gccgagcagg cggccacaca ggccagggcc    600
gccgcggccg cttttgaggc ggcgtttgcc gcgacggtgc ctccgccgtt gatcgcggcc    660
aaccgggctt cgttgatgca gctgatctcg acgaatgtct ttggtcagaa cacctcggcg    720
atcgcggccg ccgaagctca gtacggcgag atgtgggccc aagactccgc ggcgatgtat    780
gcctacgcgg gcagttcggc gagcgcctcg gcggtcacgc cgtttagcac gccgccgcag    840
attgccaacc cgaccgctca gggtacgcag gccgcggccg tggccaccgc cgccggtacc    900
gcccagtcga cgctgacgga gatgatcacc gggctaccca acgcgctgca aagcctcacc    960
tcacntctgt tgcagtcgtc taacggtccg ctgtcgtggc tgtggcagat cttgttcggc   1020
acgcccaatt tccccacctc aatttcggca ctgctgaccg acctgcagcc ctacgcgagc   1080
ttnttntata acaccgaggg cctgccgtac ttcagcatcg gcatgggcaa caacttcatt   1140
cagtcggcca agaccctggg attgatcggc taggcggcac cggctgcggt cgcggctgct   1200
ggggatgccg ccaagggctt gcctggactg ggcgggatgc tcggtggcgg gccggtggcg   1260
gcgggtctgg gcaatgcggc ttcggttggc aagctgtcgg tgccgccggt gtggantgga   1320
ccgttgcccg ggtcggtgac tccgggggct gctccgctac cggtgagtac ggtcagtgcc   1380
gccccggagg cggcgcccgg aagcctgttg ggcggcctgc cgctanctgg tgcgggcggg   1440
gccggcgcgg gtccacgcta cggattccrt cccaccgtca tggctcgccc acccttcgmc   1500
gggatagtcg ctgccgcaac gtattaacgc gccggcctcg gctggtgtgg tccgctgcgg   1560
gtggcaattg gtcngcgccg aaatctcsgt gggttattr cggtgggatt ttttcccgaa    1620
gccgggttca rcaccggatt tcctaacggt cccgckactc tcgtgccgaa ttcsgcacta   1680
agtgacgtcc ggcggaaacc cgttgggtnt gaaagcttga gaaaggcccg ctcccagggg   1740
ttcggcaaac gg                                                       1752
```

<210> SEQ ID NO 126
<211> LENGTH: 400
<212> TYPE: PRT
<213> ORGANISM: Mycobacterium tuberculosis
<220> FEATURE:
<223> OTHER INFORMATION: Tb470 (Mtb-40)
<221> NAME/KEY: MOD_RES
<222> LOCATION: (1)..(400)
<223> OTHER INFORMATION: Xaa = any amino acid

<400> SEQUENCE: 126

```
Met Asp Phe Gly Ala Leu Pro Pro Glu Val Asn Ser Val Arg Met Tyr
  1               5                  10                  15

Ala Gly Pro Gly Ser Ala Pro Met Val Ala Ala Ser Ala Trp Asn
             20                  25                  30

Gly Leu Ala Ala Glu Leu Ser Ser Ala Ala Thr Gly Tyr Glu Thr Val
         35                  40                  45

Ile Thr Gln Leu Ser Ser Glu Gly Trp Leu Gly Pro Ala Ser Ala Ala
```

```
                 50                  55                  60
Met Ala Glu Ala Val Ala Pro Tyr Val Ala Trp Met Ser Ala Ala Ala
 65                  70                  75                  80

Ala Gln Ala Glu Gln Ala Ala Thr Gln Ala Arg Ala Ala Ala Ala
                 85                  90                  95

Phe Glu Ala Ala Phe Ala Ala Thr Val Pro Pro Leu Ile Ala Ala
                100                 105                 110

Asn Arg Ala Ser Leu Met Gln Leu Ile Ser Thr Asn Val Phe Gly Gln
                115                 120                 125

Asn Thr Ser Ala Ile Ala Ala Glu Ala Gln Tyr Gly Glu Met Trp
130                 135                 140

Ala Gln Asp Ser Ala Ala Met Tyr Ala Tyr Ala Gly Ser Ser Ala Ser
145                 150                 155                 160

Ala Ser Ala Val Thr Pro Phe Ser Thr Pro Pro Gln Ile Ala Asn Pro
                165                 170                 175

Thr Ala Gln Gly Thr Gln Ala Ala Val Ala Thr Ala Ala Gly Thr
                180                 185                 190

Ala Gln Ser Thr Leu Thr Glu Met Ile Thr Gly Leu Pro Asn Ala Leu
                195                 200                 205

Gln Ser Leu Thr Ser Xaa Leu Leu Gln Ser Ser Asn Gly Pro Leu Ser
                210                 215                 220

Trp Leu Trp Gln Ile Leu Phe Gly Thr Pro Asn Phe Pro Thr Ser Ile
225                 230                 235                 240

Ser Ala Leu Leu Thr Asp Leu Gln Pro Tyr Ala Ser Xaa Xaa Tyr Asn
                245                 250                 255

Thr Glu Gly Leu Pro Tyr Phe Ser Ile Gly Met Gly Asn Asn Phe Ile
                260                 265                 270

Gln Ser Ala Lys Thr Leu Gly Leu Ile Gly Ser Ala Ala Pro Ala Ala
                275                 280                 285

Val Ala Ala Gly Asp Ala Lys Gly Leu Pro Gly Leu Gly Gly
                290                 295                 300

Met Leu Gly Gly Gly Pro Val Ala Ala Gly Leu Gly Asn Ala Ala Ser
305                 310                 315                 320

Val Gly Lys Leu Ser Val Pro Pro Val Trp Xaa Gly Pro Leu Pro Gly
                325                 330                 335

Ser Val Thr Pro Gly Ala Ala Pro Leu Pro Val Ser Thr Val Ser Ala
                340                 345                 350

Ala Pro Glu Ala Ala Pro Gly Ser Leu Leu Gly Leu Pro Leu Xaa
                355                 360                 365

Gly Ala Gly Gly Ala Gly Ala Gly Pro Arg Tyr Gly Phe Xaa Pro Thr
370                 375                 380

Val Met Ala Arg Pro Pro Phe Xaa Gly Ile Val Ala Ala Ala Thr Tyr
385                 390                 395                 400

<210> SEQ ID NO 127
<211> LENGTH: 474
<212> TYPE: DNA
<213> ORGANISM: Mycobacterium tuberculosis
<220> FEATURE:
<223> OTHER INFORMATION: Tb366 cDNA

<400> SEQUENCE: 127
ggcacgagca ccagttgacc cgcgaagaac ctgaccgcgc acccagcgc cgcccgcatc      60 accggccccg tccacgaac cttttcggta acgagccac tccagcggag atcggtaccg     120
```

| | |
|---|---|
| cccgacgcat tgggtgtaag gaccacctcg ccgaagtagt cctggacggg tgtcctcgcg | 180 |
| ccaaccagct tgtagacgtg gcgacggtcc tgctcatact cgacggtctc ttcctgcacg | 240 |
| aacaccggcc acatgcctag tttgcggatg gccccgatgc cgccgggcgc gggatcaccg | 300 |
| cgtcgcgccc aactcgattg agcaacgatg ggcttggccc aggtcgccca gttgccaccg | 360 |
| tctgtcacga gccgaaacaa ggttgcagcc ggcgcgctgc tggtcttggt gacctcgaac | 420 |
| gaaaatttcc gacccgacat gcgcgactcc cgaaacgaca actgaagctc gtgc | 474 |

<210> SEQ ID NO 128
<211> LENGTH: 1431
<212> TYPE: DNA
<213> ORGANISM: Mycobacterium tuberculosis
<220> FEATURE:
<223> OTHER INFORMATION: Tb433 cDNA
<221> NAME/KEY: modified_base
<222> LOCATION: (18)
<223> OTHER INFORMATION: n = g, a, c or t

<400> SEQUENCE: 128

| | |
|---|---|
| ctgcgcgccg gaaaaaanta ttactggcag gaccggcaga atgcatggtg atattccggt | 60 |
| gatgaggccg ccgaggaacc gactagtgcg agggtcaaca catcggttat tcgttgccgt | 120 |
| ttaggtcttg gatctgccgg gacggcaacg agttggcagg accgctcacg cgagcgctgt | 180 |
| tgacagagtc ggttcacgtc gaactcgcca cccgtcagat gcgaatgata gccacatcgg | 240 |
| ccacaccatc gacggcgtcg aagtcgccgt cgtgggtcac gaccggcacc ccttgcgacg | 300 |
| tggcaacggc agcggccctc accggacggg accgagatcg tcgtggtgt cgccagtgag | 360 |
| cgttgcgagg tcgcgggtgc aatcccgcat ctgcttgcgt atgccgaagc gccgcagca | 420 |
| gctcgtctcg actcaaccat cggcgccgtg cgggctgcct gcggtcagca gcgcaacggg | 480 |
| tttgccgttg gcagtgatgg tgatgtcttc gccggcctgc acgcgccgta gcagcccggc | 540 |
| ggtgttgttg cgcagttcgc gagacgcgac ttcagcaggc atgctgcggg gatcggcttg | 600 |
| cgctgggcgc ggtgtcaccg tcatgcgctt gggatatcac gtgatctatc ggcacgaagc | 660 |
| cgccggatga gcgaggcaaa ccgcctacac gggctgcctc gccttgaccg cgccgaacgt | 720 |
| tactgtgccg ggggcatcag caccgtatcg atcatgtaca ccgtcgcgtg ggcggtgtga | 780 |
| ctccgccaca taccaaacgg gcgttgttga ccatgagtcg tcgcgggcgc ctatcaccgt | 840 |
| caggtcggca ccttgcaggt ctgatgggtg ccgtcgatcc tgctcggact cgcctggccg | 900 |
| gctatcacgt ggtaggtcag gatgctgctg agcagcttgg cgtcagtctt gagttgatcg | 960 |
| atagtggccg ccggcagctt gtcgaatgcg gcgttggtgg gggcgaaaac ggtgtactcg | 1020 |
| ccgccgttga gggtgtcgac cagattcaca tccgggttca gcttgcccga cagagccgag | 1080 |
| gtcagggtac tgagcatcgg gttgttggaa gccgcggtag cgaccgggtc ttgcgccatt | 1140 |
| ccggccaccg atccgggacc ggtgggattt tgcgccgcgt attgcgcgca cccacgacca | 1200 |
| atcaggtccg ctgcggtcag ccattgccgc cgtggtaacg ggcgccgccg ggctggtcgc | 1260 |
| cggtttcggg ctggtgtctt gcgacacggg tttggtgctc gaacaacccg ctaagaacgc | 1320 |
| aatcgcgatg gctgcgaggc tcgctgctgc ggccggtttg gcctgaacgt tgatcatcgc | 1380 |
| ttcgattcct ttgcttctgc ggcggcgttg aacgccgtcc tcctgggtgg a | 1431 |

<210> SEQ ID NO 129
<211> LENGTH: 279
<212> TYPE: DNA
<213> ORGANISM: Mycobacterium tuberculosis
<220> FEATURE:

<223> OTHER INFORMATION: Tb439 cDNA

<400> SEQUENCE: 129

| | | | | |
|---|---|---|---|---|
| gcacgagagt | cgtatctttg | cacccagcgc | ccgtaggaaa | ccgctggcct | ggctaactca | 60 |
| gatgcgggcg | gccgtcgatt | cgagaggtaa | ccgatcgccc | gccgacaatg | ggttacccac | 120 |
| cgagactgat | tgccgcgcag | ccgccttcga | cgtgtaagcg | ccggttcgtg | catgcccgga | 180 |
| acggctgcac | tcacggacct | tctacgtagt | acgtgacgga | cttttacgca | ttatcgctga | 240 |
| cgatctttgc | ctcccaggac | tccagaatct | actcgtgcc | | | 279 |

<210> SEQ ID NO 130
<211> LENGTH: 1470
<212> TYPE: DNA
<213> ORGANISM: Mycobacterium tuberculosis
<220> FEATURE:
<223> OTHER INFORMATION: Tb372 cDNA

<400> SEQUENCE: 130

| | | | | | | |
|---|---|---|---|---|---|---|
| accgccaccc | gcagcccgga | atcaccgtcg | gtaacctgcg | aatacaattt | cttcatcgac | 60 |
| gacttcgcga | acagcgaacc | cgagcccacc | gcctgatagc | cttcttcctc | gatgttccaa | 120 |
| ccgccggcgg | cgtcgaacga | aacgatacga | cccgcgctct | gcgggtcaga | cgcatgaatg | 180 |
| tcgtagcccg | ccagcaacgg | caacgccagc | agacccgtgca | tcgcggccgc | cagattgcca | 240 |
| cgcaccataa | tcgccagccg | gttgattttg | ccggcaaacg | tcagcggcac | accctcgagc | 300 |
| ttctcgtagt | gctcaagttc | cacggcatac | agccgggcaa | actcaaccgc | gaccgcagcc | 360 |
| gtgccagcga | tgccggtagc | ggtgtagtca | tcggtgatat | acaccttgcg | cacatcacgc | 420 |
| ccagaaatca | tgttgccctg | cgtcgaacgc | cggtcacccg | ccatgacaac | accgccgggg | 480 |
| tatttcagcg | cgacaatggt | ggtgccgtgc | ggcagttgcg | catcgccgcc | tgcgagtggc | 540 |
| gcaccgccgc | tgatgcttgc | cggcagcaac | tccggcgcct | ggcggcgcag | gaagtcaagt | 600 |
| gaaagaagat | aggtctacag | cgggtgttcc | agagagtgaa | ttaatggaca | ggcgatcggg | 660 |
| caacggccag | gtcactgtcc | gccccttttgg | acgtatgcgc | ggacgaagtc | ctcggcgttc | 720 |
| tcctcgagga | cgtcgtcgat | ttcgtcgagc | agatcgtcgg | tctcctcggt | cagcttttcg | 780 |
| cgacgctcct | ggcccgcggc | ggtgctgccg | gcgatgtcgt | catcatcgcc | gccgccaccg | 840 |
| ccacgcttgg | tctgctcttg | cgccatcgcc | gcctcctgct | tcctcatggc | ctttcaaaag | 900 |
| gccgcgggtg | cgcgtcacac | gcccgctgtc | tttctctcac | ctaccggtca | acaccaacgt | 960 |
| ttcccggcct | aaccaggctt | agcgaggctc | agcggtcagt | tgctctacca | gctccacggc | 1020 |
| actgtccacc | gaatccagca | acgcaccaac | atgcgcctta | ctaccccgca | acggctccag | 1080 |
| cgtcgggatg | cgaaccagcg | agtcgccgcc | aggtcgaaga | tcaccgagtc | ccagctagcc | 1140 |
| gcggcgatat | cagccccgaa | ccggcgcagg | catttcgccg | cggaaatacg | cgcgggtgtc | 1200 |
| ggtcggcggt | tctccaccgc | actcagcacc | tggtgtttcg | gtgactaaac | gctttatcga | 1260 |
| gccgcgcgcg | accagccggt | tgtacaggcc | cttgtccagc | cggacatcgg | agtactgcag | 1320 |
| gttgacgagg | tgcagccggg | gcgccgacca | gtcaggttc | tcccgctgcc | ggaaaccgtc | 1380 |
| gagcagccgc | agtttggccg | gccagtccag | cagctccgcg | caatccatcg | ggtcacgctc | 1440 |
| gagctgatcc | agcacgtgtg | cccaggtttc | | | | 1470 |

<210> SEQ ID NO 131
<211> LENGTH: 1059
<212> TYPE: DNA
<213> ORGANISM: Mycobacterium tuberculosis
<220> FEATURE:
<223> OTHER INFORMATION: Tb372 cDNA

<400> SEQUENCE: 131

| | | | | | |
|---|---|---|---|---|---:|
| attcccatcg | ctccggcacc | tatcaccagg | tagtcggttt | cgatggtttt | cgccggccct | 60 |
| tgcgttggcc | tgggccacgg | gtcgttcatg | ggccctcctg | tgcggattgg | aatttgtgac | 120 |
| aacgaaatcg | ggcgatcggt | gagcaatcgt | cgccgatgca | agacacgctt | tcgctgccgc | 180 |
| ggcgtcaggt | ggagtttagg | ccagcgtaac | aacgtagacc | ggccactgac | caaaccccaa | 240 |
| acccacaaac | cctggacgca | tgcgggtctc | ggcgtcaaa | ttccgggtag | atatcgtata | 300 |
| ccgatatcgg | atgccgtagc | cttatcgagg | catgagacgc | ccgctagacc | cacgcgatat | 360 |
| tccagatgag | ctgcggcgac | ggctggggct | cttggatgcg | gtggtgatcg | ggcttgggtc | 420 |
| catgatcggt | gccggaatct | tgctcgtgc | cgaattcggc | acgagctcgt | gccgaattcg | 480 |
| gcacgagatt | ccaatcccca | gaaggtcgta | caagccgtca | atggcacttg | atcgttggat | 540 |
| cgatgatgaa | cgctctgctc | atgcctgccg | cctatctcaa | cggtcgtcga | ttccatgcat | 600 |
| tagccttggt | tctgcattgc | acgcgtaggg | cctacagtct | ggctgtcatg | cttggccgat | 660 |
| gtcaacagtt | tttttcatgc | taagcagatc | gtcagttttg | agttcgtgaa | gacggcatgt | 720 |
| tcacttgttg | tcgactacat | cgtctgcgca | catttgccct | cctgcaactg | cgctgcgaca | 780 |
| atgcgccaac | cgccgtgtag | ctcgtgccga | attcggcacg | aggatccacc | ggagatggcc | 840 |
| gacgactacg | acgaggcctg | gatgctcaac | accgtgttcg | actatcacaa | cgagaacgca | 900 |
| aaagaagagg | tcatccatct | cgtgcccgac | gtgaacaagg | agaggggcc | catcgaactc | 960 |
| gtaaccaagg | tagacaaaga | gggacatcag | actcgtctac | gatggggagc | cacgttttca | 1020 |
| tacaaggaac | atcctaagtt | ttgattcggg | aacatccta | | | 1059 |

<210> SEQ ID NO 132
<211> LENGTH: 153
<212> TYPE: DNA
<213> ORGANISM: Mycobacterium tuberculosis
<220> FEATURE:
<223> OTHER INFORMATION: Tb390R5C6 cDNA

<400> SEQUENCE: 132

| | | | | | |
|---|---|---|---|---|---:|
| gcacgaggca | ttggcgggca | tctgcataaa | cggtgacgta | tcagcacaaa | acagcggaga | 60 |
| gaacaacatg | cgatcagaac | gtctccggtg | gctggtagcc | gcagaaggtc | cgttcgcctc | 120 |
| ggtgtatttc | gacgactcgc | acgactcgtg | ccg | | | 153 |

<210> SEQ ID NO 133
<211> LENGTH: 387
<212> TYPE: DNA
<213> ORGANISM: Mycobacterium tuberculosis
<220> FEATURE:
<223> OTHER INFORMATION: Tb390R2C11 cDNA

<400> SEQUENCE: 133

| | | | | | |
|---|---|---|---|---|---:|
| ccgcgcggtc | gatcagcgag | ccaggcaaaa | actccgtcga | gcccgagtcg | atgatggtca | 60 |
| cccggcgcag | catctggcga | acgatcacct | cgatgtgctt | gtcgtggatc | gacacacctt | 120 |
| gggcgcggta | gacctcctgg | acctcgcgaa | ccaggtgtat | ctgcacctcg | cggggcccct | 180 |
| gcacccgcag | cacctcatgc | gggtcggccg | agccttccat | cagctgctgg | cccacctcga | 240 |
| cgtggtcgcc | atcggagagc | acccgttccg | aaccgtcttc | gtgcttgaac | acccgcagcc | 300 |
| gctgccgctt | ggagatcttg | tcgtagacca | cttcctcacc | gccgtcgtca | ggaacgatgg | 360 | tgatcttgta gaaccgctcg ccgtcct                                              387

<210> SEQ ID NO 134
<211> LENGTH: 389
<212> TYPE: DNA
<213> ORGANISM: Mycobacterium tuberculosis
<220> FEATURE:
<223> OTHER INFORMATION: Tb390R2C11 cDNA

<400> SEQUENCE: 134
gttcagcacg gctatccgat tgtgccgttc gcttcggtgg gtgctgaaca cggcatcgac    60
atcgtgctcg acaacgaatc cccactgctg caccggtcc agttcctcgc cgagaagctg   120
ctcggcacca agacggtcc ggcgctggtc cgtggtgtcg gactgacacc ggtaccgcgc   180
cccgaacggc agtattactg gttcggcgag ccaaccgaca ccacagagtt tatgggcag   240
caagccgacg ataacgccgc acgcagggtg cgcgagcgtg ccgccgccgc tatcgaacac   300
ggcatcgagc tgatgctggc cgagcgcgca gccgatccaa atcgatccct ggtcggacgg   360
ctcttgcgct cggacgccta aggcgcccc                                      389

<210> SEQ ID NO 135
<211> LENGTH: 480
<212> TYPE: DNA
<213> ORGANISM: Mycobacterium tuberculosis
<220> FEATURE:
<223> OTHER INFORMATION: Y1-26C1 5' cDNA
<221> NAME/KEY: modified_base
<222> LOCATION: (1)..(480)
<223> OTHER INFORMATION: n = g, a, c or t

<400> SEQUENCE: 135
cccgcggtcg gaatgatccc cgtctcgtcg cgcgcccatt tgatgctgtt gatgagctgt    60
ttggagaagc ccggttggcg taccggtgag ccggaatatc tgttggaagc gtcaccggat   120
gtncacatga antncttgn cccngtngcg gtnttggntg nggnaaacac gtgttgtnta   180
agccttgntg gnctcgnaag ngccgtngac gcctgtgtcg ccgaagataa tgagcacctg   240
acggttggcg ggatcgccgt tatcccaagg aattccgagg tcggtcccgg agatgccgaa   300
gcgttccagg gtcttgttgg ggctgtccgg tccggtcacc cactcggcga gggatgtggn   360
agccccggcg agcgtggcac caggatccgg cgccgccgcc ggagcagggt cggnngctgn   420
nctgnnttcc tnnngccnaa ttnnactccn ncnacaanct tgnnnccgac tcnnacccgn   480

<210> SEQ ID NO 136
<211> LENGTH: 587
<212> TYPE: DNA
<213> ORGANISM: Mycobacterium tuberculosis
<220> FEATURE:
<223> OTHER INFORMATION: Y1-86C11 5' cDNA
<221> NAME/KEY: modified_base
<222> LOCATION: (1)..(587)
<223> OTHER INFORMATION: n = g, a, c or t

<400> SEQUENCE: 136
gcacgaggct accggcgcgt cgcccgccat gccctggatg cacgcgtagc cacccgtnca    60
tncagcgggt cagccgccgc gtccgggctt aacgctatag cagctgcaaa caacccagcg   120
ccggcaatta ctttgatgtt gaaccgatga ccatngcctn cgngtncaat ctcntctctt   180
ngcgcgccnc tatttnngcc atanatttgg ttnnanncgn aacgctagac gtatcgagtt   240
ccttttcgac caccggctca attgtcagca tcctatgggg aacatgagcc ccgccgcacc   300
gggccgtttc caaatggtga cgtcacaacg gtgtcacaag ccagcgcaat gtccgcgta   360

```
gggacgcggc ggctgggatc ggtggggtga gcgcccggct tctcaaagcg aggggagccc        420
cgggactctt accggccgaa ggcggcgggt gtcactgatc taggctgacg gccagtggtt        480
gntnagccaa caaggatgac nacaaataan ccgagganag acangngacg gnccgananc        540
ctnanccggn nttgnncnaa nnnnacncac ttntaccgnn cttatgn                      587
```

<210> SEQ ID NO 137
<211> LENGTH: 1200
<212> TYPE: DNA
<213> ORGANISM: Mycobacterium tuberculosis
<220> FEATURE:
<223> OTHER INFORMATION: full-length hTcc#1 cDNA

<400> SEQUENCE: 137

```
caggcatgag cagagcgttc atcatcgatc caacgatcag tgccattgac ggcttgtacg         60
accttctggg gattggaata cccaaccaag ggggtatcct ttactcctca ctagagtact        120
tcgaaaaagc cctggaggag ctggcagcag cgtttccggg tgatggctgg ttaggttcgg        180
ccgcggacaa atacgccggc aaaaaccgca accacgtgaa ttttttccag gaactggcag        240
acctcgatcg tcagctcatc agcctgatcc acgaccaggc caacgcggtc cagacgaccc        300
gcgacatcct ggagggcgcc aagaaaggtc tcgagttcgt gcgcccggtg gctgtggacc        360
tgacctacat cccggtcgtc gggcacgccc tatcggccgc cttccaggcg ccgttttgcg        420
cgggcgcgat ggccgtagtg ggcggcgcgc ttgcctactt ggtcgtgaaa acgctgatca        480
acgcgactca actcctcaaa ttgcttgcca aattggcgga gttggtcgcg ccgccattg         540 cggacatcat ttcggatgtg gcggacatca tcaagggcac cctcggagaa gtgtgggagt        600
tcatcacaaa cgcgctcaac ggcctgaaag gctttggga caagctcacg gggtgggtga        660
ccggactgtt ctctcgaggg tggtcgaacc tggagtcctt ctttgcgggc gtccccggct        720
tgaccggcgc gaccagcggc ttgtcgcaag tgactggctt gttcggtgcg gccggtctgt        780
ccgcatcgtc gggcttggct cacgcggata gcctggcgag ctcagccagc ttgcccgccc        840
tggccggcat tggggcggg tccggttttg ggggcttgcc gagcctggct caggtccatg         900
ccgcctcaac tcggcaggcg ctacggcccc gagctgatgg cccggtcggc gccgctgccg        960
agcaggtcgg cggcagtcg cagctggtct ccgcgcaggg ttcccaaggt atgggcggac        1020
ccgtaggcat gggcggcatg caccctctt cgggggcgtc gaaagggacg acgacgaaga        1080
agtactcgga aggcgcggcg gcgggcactg aagacgccga gcgcgcgcca gtcgaagctg        1140
acgcgggcgg tgggcaaaag gtgctggtac gaaacgtcgt ctaacggcat ggcgagccaa        1200
```

<210> SEQ ID NO 138
<211> LENGTH: 392
<212> TYPE: PRT
<213> ORGANISM: Mycobacterium tuberculosis
<220> FEATURE:
<223> OTHER INFORMATION: hTcc#1

<400> SEQUENCE: 138

```
Met Ser Arg Ala Phe Ile Ile Asp Pro Thr Ile Ser Ala Ile Asp Gly
  1               5                  10                  15

Leu Tyr Asp Leu Leu Gly Ile Gly Ile Pro Asn Gln Gly Gly Ile Leu
             20                  25                  30

Tyr Ser Ser Leu Glu Tyr Phe Glu Lys Ala Leu Glu Glu Leu Ala Ala
         35                  40                  45

Ala Phe Pro Gly Asp Gly Trp Leu Gly Ser Ala Ala Asp Lys Tyr Ala
```

-continued

```
    50                  55                  60

Gly Lys Asn Arg Asn His Val Asn Phe Phe Gln Glu Leu Ala Asp Leu
 65                  70                  75                  80

Asp Arg Gln Leu Ile Ser Leu Ile His Asp Gln Ala Asn Ala Val Gln
                 85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240

Gly Ala Thr Ser Gly Leu Ser Gln Val Thr Gly Leu Phe Gly Ala Ala
                245                 250                 255

Gly Leu Ser Ala Ser Ser Gly Leu Ala His Ala Asp Ser Leu Ala Ser
            260                 265                 270

Ser Ala Ser Leu Pro Ala Leu Ala Gly Ile Gly Gly Gly Ser Gly Phe
        275                 280                 285

Gly Gly Leu Pro Ser Leu Ala Gln Val His Ala Ala Ser Thr Arg Gln
    290                 295                 300

Ala Leu Arg Pro Arg Ala Asp Gly Pro Val Gly Ala Ala Ala Glu Gln
305                 310                 315                 320

Val Gly Gly Gln Ser Gln Leu Val Ser Ala Gln Gly Ser Gln Gly Met
                325                 330                 335

Gly Gly Pro Val Gly Met Gly Gly Met His Pro Ser Ser Gly Ala Ser
            340                 345                 350

Lys Gly Thr Thr Thr Lys Lys Tyr Ser Glu Gly Ala Ala Ala Gly Thr
        355                 360                 365

Glu Asp Ala Glu Arg Ala Pro Val Glu Ala Asp Ala Gly Gly Gly Gln
    370                 375                 380

Lys Val Leu Val Arg Asn Val Val
385                 390

<210> SEQ ID NO 139
<211> LENGTH: 439
<212> TYPE: DNA
<213> ORGANISM: Mycobacterium tuberculosis
<220> FEATURE:
<223> OTHER INFORMATION: mTCC#1 cDNA

<400> SEQUENCE: 139
acgtttaccc atgccgtcgg tgcagagcaa cgccagacaa cacaaagtag tctaattccg      60
ttataaagca gacatttccg tggttatgta gaagatgtcg accgatcaga tgaagcgatc     120
```

-continued

```
cgcgtcaggt ggtatccgat gtcttttgtg accatccagc cggtggtctt ggcagccgcg    180 acggggact tgccgacgat cggtaccgcc gtgagtgctc ggaacacagc cgtctgtgcc     240
ccgacgacgg gggtgttacc ccctgctgcc aatgacgtgt cggtcctgac ggcggcccgg    300
ttcaccgcgc acaccaagca ctaccgagtg gtgagtaagc cggccgcgct ggtccatggc    360
atgttcgtgg ccctcccggc ggccaccgcc gatgcgtatg cgaccaccga ggccgtcaat    420
gtggtcgcga ccggttaag                                                439
```

<210> SEQ ID NO 140
<211> LENGTH: 1441
<212> TYPE: DNA
<213> ORGANISM: Mycobacterium tuberculosis
<220> FEATURE:
<223> OTHER INFORMATION: mTCC#2 cDNA

<400> SEQUENCE: 140

```
gaggttgctg gcaatggatt tcgggctttt acctccggaa gtgaattcaa gccgaatgta    60
ttccggtccg gggccggagt cgatgctagc cgccgcggcc gcctgggacg gtgtggccgc    120
ggagttgact tccgccgcgg tctcgtatgg atcggtggtg tcgacgctga tcgttgagcc    180
gtggatgggg ccggcggcgg ccgcgatggc ggccgcggca acgccgtatg tggggtggct    240
ggccgccacg gcgcgctgg cgaaggagac ggccacacag gcgagggcag cggcggaagc    300
gtttgggacg gcgttcgcga tgacggtgcc accatccctc gtcgcggcca accgcagccg    360
gttgatgtcg ctggtcgcgg cgaacattct ggggcaaaac agtgcggcga tcgcggctac    420
ccaggccgag tatgccgaaa tgtgggccca agacgctgcc gtgatgtaca gctatgaggg    480
ggcatctgcg gccgcgtcgg cgttgccgcc gttcactcca cccgtgcaag gcaccggccc    540
ggccgggccc gcggccgcag ccgcggcgac ccaagccgcc ggtgcgggcg ccgttgcgga    600
tgcacaggcg acactggccc agctgccccc ggggatcctg agcgacattc tgtccgcatt    660
ggccgccaac gctgatccgc tgacatcggg actgttgggg atcgcgtcga ccctcaaccc    720
gcaagtcgga tccgctcagc cgatagtgat ccccaccccg ataggggaat tggacgtgat    780
cgcgctctac attgcatcca tcgcgaccgg cagcattgcg ctcgcgatca cgaacacggc    840
cagaccctgg cacatcggcc tatacgggaa cgccggcggg ctgggaccga cgcagggcca    900
tccactgagt tcggcgaccg acgagccgga gccgcactgg ggcccttcg ggggcgcggc    960 gccggtgtcc gcgggcgtcg gccacgcagc attagtcgga gcgttgtcgg tgccgcacag    1020
ctggaccacg gccgccccgg agatccagct cgccgttcag gcaacaccca ccttcagctc    1080
cagcgccggc gccgacccga cggccctaaa cgggatgccg gcaggcctgc tcagcgggat    1140
ggctttggcg agcctggccg cacgcggcac gacgggcggt ggcggcaccc gtagcggcac    1200
cagcactgac ggccaagagg acggccgcaa accccggta gttgtgatta gagagcagcc    1260
gccgcccgga aaccccccgc ggtaaaagtc cggcaaccgt tcgtcgccgc gcggaaaatg    1320
cctggtgagc gtggctatcc gacgggccgt tcacaccgct tgtagtagcg tacggctatg    1380
gacgacggtg tctggattct cggcggctat cagagcgatt ttgctcgcaa cctcagcaaa    1440
g                                                                   1441
```

<210> SEQ ID NO 141
<211> LENGTH: 99
<212> TYPE: PRT
<213> ORGANISM: Mycobacterium tuberculosis
<220> FEATURE:
<223> OTHER INFORMATION: mTCC#1

```
<400> SEQUENCE: 141

Met Ser Phe Val Thr Ile Gln Pro Val Leu Ala Ala Thr Gly
1               5                   10                  15

Asp Leu Pro Thr Ile Gly Thr Ala Val Ser Ala Arg Asn Thr Ala Val
            20                  25                  30

Cys Ala Pro Thr Thr Gly Val Leu Pro Ala Ala Asn Asp Val Ser
        35                  40                  45

Val Leu Thr Ala Ala Arg Phe Thr Ala His Thr Lys His Tyr Arg Val
    50                  55                  60

Val Ser Lys Pro Ala Ala Leu Val His Gly Met Phe Val Ala Leu Pro
65                  70                  75                  80

Ala Ala Thr Ala Asp Ala Tyr Ala Thr Thr Glu Ala Val Asn Val Val
                85                  90                  95

Ala Thr Gly

<210> SEQ ID NO 142
<211> LENGTH: 423
<212> TYPE: PRT
<213> ORGANISM: Mycobacterium tuberculosis
<220> FEATURE:
<223> OTHER INFORMATION: mTCC#2

<400> SEQUENCE: 142

Met Asp Phe Gly Leu Leu Pro Pro Glu Val Asn Ser Ser Arg Met Tyr
1               5                   10                  15

Ser Gly Pro Gly Pro Glu Ser Met Leu Ala Ala Ala Ala Trp Asp
            20                  25                  30

Gly Val Ala Ala Glu Leu Thr Ser Ala Ala Val Ser Tyr Gly Ser Val
        35                  40                  45

Val Ser Thr Leu Ile Val Glu Pro Trp Met Gly Pro Ala Ala Ala
    50                  55                  60

Met Ala Ala Ala Thr Pro Tyr Val Gly Trp Leu Ala Ala Thr Ala
65                  70                  75                  80

Ala Leu Ala Lys Glu Thr Ala Thr Gln Ala Arg Ala Ala Ala Glu Ala
                85                  90                  95

Phe Gly Thr Ala Phe Ala Met Thr Val Pro Pro Ser Leu Val Ala Ala
                100                 105                 110

Asn Arg Ser Arg Leu Met Ser Leu Val Ala Asn Ile Leu Gly Gln
        115                 120                 125

Asn Ser Ala Ala Ile Ala Ala Thr Gln Ala Glu Tyr Ala Glu Met Trp
    130                 135                 140

Ala Gln Asp Ala Ala Val Met Tyr Ser Tyr Glu Gly Ala Ser Ala Ala
145                 150                 155                 160

Ala Ser Ala Leu Pro Pro Phe Thr Pro Pro Val Gln Gly Thr Gly Pro
                165                 170                 175

Ala Gly Pro Ala Ala Ala Ala Ala Thr Gln Ala Ala Gly Ala Gly
                180                 185                 190

Ala Val Ala Asp Ala Gln Ala Thr Leu Ala Gln Leu Pro Pro Gly Ile
        195                 200                 205

Leu Ser Asp Ile Leu Ser Ala Leu Ala Ala Asn Ala Asp Pro Leu Thr
    210                 215                 220

Ser Gly Leu Leu Gly Ile Ala Ser Thr Leu Asn Pro Gln Val Gly Ser
225                 230                 235                 240

Ala Gln Pro Ile Val Ile Pro Thr Pro Ile Gly Glu Leu Asp Val Ile
```

-continued

```
                245                 250                 255
Ala Leu Tyr Ile Ala Ser Ile Ala Thr Gly Ser Ile Ala Leu Ala Ile
            260                 265                 270

Thr Asn Thr Ala Arg Pro Trp His Ile Gly Leu Tyr Gly Asn Ala Gly
        275                 280                 285

Gly Leu Gly Pro Thr Gln Gly His Pro Leu Ser Ser Ala Thr Asp Glu
    290                 295                 300

Pro Glu Pro His Trp Gly Pro Phe Gly Gly Ala Ala Pro Val Ser Ala
305                 310                 315                 320

Gly Val Gly His Ala Ala Leu Val Gly Ala Leu Ser Val Pro His Ser
                325                 330                 335

Trp Thr Thr Ala Ala Pro Glu Ile Gln Leu Ala Val Gln Ala Thr Pro
            340                 345                 350

Thr Phe Ser Ser Ser Ala Gly Ala Asp Pro Thr Ala Leu Asn Gly Met
        355                 360                 365

Pro Ala Gly Leu Leu Ser Gly Met Ala Leu Ala Ser Leu Ala Ala Arg
    370                 375                 380

Gly Thr Thr Gly Gly Gly Gly Thr Arg Ser Gly Thr Ser Thr Asp Gly
385                 390                 395                 400

Gln Glu Asp Gly Arg Lys Pro Pro Val Val Val Ile Arg Glu Gln Pro
                405                 410                 415

Pro Pro Gly Asn Pro Pro Arg
            420

<210> SEQ ID NO 143
<211> LENGTH: 97
<212> TYPE: PRT
<213> ORGANISM: Mycobacterium tuberculosis
<220> FEATURE:
<223> OTHER INFORMATION: Mtb9.8

<400> SEQUENCE: 143

Met Ser Leu Leu Asp Ala His Ile Pro Gln Leu Val Ala Ser Gln Ser
  1               5                  10                  15

Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
        35                  40                  45

Ala Ala Phe Gln Ala Ala His Ala Arg Phe Val Ala Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ser Thr Tyr Thr Gly
                85                  90                  95

Phe

<210> SEQ ID NO 144
<211> LENGTH: 99
<212> TYPE: PRT
<213> ORGANISM: Mycobacterium tuberculosis
<220> FEATURE:
<223> OTHER INFORMATION: Tb#470
<221> NAME/KEY: MOD_RES
<222> LOCATION: (1)..(99)
<223> OTHER INFORMATION: Xaa = any amino acid

<400> SEQUENCE: 144

Cys Arg Leu Cys Leu Asp Ser His Leu Arg Val Val Ala Leu Pro Ala
```

```
               1               5                  10                    15
Gly Gln Pro Gly Arg Leu Val Gln Ala Ile Gly Pro Ala Gln Glu Arg
                20                  25                  30

Asp Val Gly Gln Thr Arg Cys Thr Arg Thr Gly Leu Asp Xaa Val Ser
            35                  40                  45

Ala Leu Thr Ala Ala Gln Phe Ala Ala His Ala Gln Ile Tyr Gln Ala
        50                  55                  60

Val Ser Ala Gln Ala Ala Ala Ile His Glu Met Phe Val Asn Thr Leu
 65                  70                  75                  80

Gln Xaa Xaa Ser Gly Ser Tyr Ala Ala Thr Glu Ala Ala Asn Ala Ala
                85                  90                  95

Ala Ala Gly

<210> SEQ ID NO 145
<211> LENGTH: 1794
<212> TYPE: DNA
<213> ORGANISM: Artificial Sequence
<220> FEATURE:
<223> OTHER INFORMATION: Description of Artificial Sequence:mTTC#3-His
      (MTB57)
<221> NAME/KEY: CDS
<222> LOCATION: (1)..(1794)
<223> OTHER INFORMATION: mTTC#3-His (MTB57)

<400> SEQUENCE: 145 atg cat cac cat cac cat cac atg aat tat tcg gtg ttg ccg ccg gag      48
Met His His His His His His Met Asn Tyr Ser Val Leu Pro Pro Glu
 1               5                  10                  15 att aat tcg ttg cgg atg ttt acc ggt gcg ggg tct gcg ccg atg ctt      96
Ile Asn Ser Leu Arg Met Phe Thr Gly Ala Gly Ser Ala Pro Met Leu
            20                  25                  30 gcg gca tcg gtg gct tgg gat ggt ttg gcc gcg gag ttg gcg gtg gcg     144
Ala Ala Ser Val Ala Trp Asp Gly Leu Ala Ala Glu Leu Ala Val Ala
        35                  40                  45 gcg tcc tcg ttt ggg tcg gtg act tcg ggg ttg gcg ggt cag tcc tgg     192
Ala Ser Ser Phe Gly Ser Val Thr Ser Gly Leu Ala Gly Gln Ser Trp
    50                  55                  60 cag ggt gcg gcg gcg gcg gcg atg gcc gcg gcg gcg gcg ccg tat gcg     240
Gln Gly Ala Ala Ala Ala Ala Met Ala Ala Ala Ala Ala Pro Tyr Ala
65                  70                  75                  80 ggg tgg ttg gct gct gcg gcg gcg cgg gcc gct ggc gcg tcg gct cag     288
Gly Trp Leu Ala Ala Ala Ala Ala Arg Ala Ala Gly Ala Ser Ala Gln
                85                  90                  95 gcc aag gcg gtg gcc agt gcg ttt gag gcg gcg cgg gcg gcg acg gtg     336
Ala Lys Ala Val Ala Ser Ala Phe Glu Ala Ala Arg Ala Ala Thr Val
            100                 105                 110 cat ccg atg ctg gtg gcg gcc aac cgt aat gcg ttt gtg cag ttg gtg     384
His Pro Met Leu Val Ala Ala Asn Arg Asn Ala Phe Val Gln Leu Val
        115                 120                 125 ttg tcg aat ctg ttt ggg cag aat gcg ccg gcg atc gcg gcc gct gag     432
Leu Ser Asn Leu Phe Gly Gln Asn Ala Pro Ala Ile Ala Ala Ala Glu
    130                 135                 140 gcg atg tat gaa cag atg tgg gcc gcc gat gtg gcc gcg atg gtg ggc     480
Ala Met Tyr Glu Gln Met Trp Ala Ala Asp Val Ala Ala Met Val Gly
145                 150                 155                 160 tat cac ggc ggg gca tcg gcg gcc gcg cag ctg tcg tcg tgg tca         528
Tyr His Gly Gly Ala Ser Ala Ala Ala Gln Leu Ser Ser Trp Ser
                165                 170                 175 att ggt ctg cag cag gcg ttg cca gct gcg cca tcg gcg ctg gcc gcc     576
Ile Gly Leu Gln Gln Ala Leu Pro Ala Ala Pro Ser Ala Leu Ala Ala
```

```
                180              185              190
gcg atc ggc ctc ggc aac atc ggc gtc ggg aac ctg ggc ggc ggg aac     624
Ala Ile Gly Leu Gly Asn Ile Gly Val Gly Asn Leu Gly Gly Gly Asn
        195              200              205 acc ggt gac tac aat ctg ggc agc gga aat tcc ggc aac gcc aac gta     672
Thr Gly Asp Tyr Asn Leu Gly Ser Gly Asn Ser Gly Asn Ala Asn Val
        210              215              220 ggt agc gga aac tcc ggc aac gcc aat gtg ggc agc gga aat gac ggt     720
Gly Ser Gly Asn Ser Gly Asn Ala Asn Val Gly Ser Gly Asn Asp Gly
225              230              235              240 gcc acg aat ttg ggc agc gga aat atc ggc aac acc aat ctc ggc agc     768
Ala Thr Asn Leu Gly Ser Gly Asn Ile Gly Asn Thr Asn Leu Gly Ser
                245              250              255 gga aac gtt ggc aat gtc aat ctg ggc agc gga aac cga ggc ttt gga     816
Gly Asn Val Gly Asn Val Asn Leu Gly Ser Gly Asn Arg Gly Phe Gly
            260              265              270 aac ctc ggc aac gga aac ttt ggc agt ggg aac ctg ggc agt gga aac     864
Asn Leu Gly Asn Gly Asn Phe Gly Ser Gly Asn Leu Gly Ser Gly Asn
            275              280              285 acc gga agt acc aac ttc ggc ggc gga aat ctc ggt tcc ttc aac ttg     912
Thr Gly Ser Thr Asn Phe Gly Gly Gly Asn Leu Gly Ser Phe Asn Leu
        290              295              300 ggc agt gga aac atc ggc tcc tcc aac atc ggt ttc gga aac aac ggc     960
Gly Ser Gly Asn Ile Gly Ser Ser Asn Ile Gly Phe Gly Asn Asn Gly
305              310              315              320 gac aat aac ctc ggc ctc ggg aac aat ggc aac aac aac atc ggt ttt    1008
Asp Asn Asn Leu Gly Leu Gly Asn Asn Gly Asn Asn Asn Ile Gly Phe
                325              330              335 ggg ctc acc ggc gac aac ttg gtg ggc att ggc gcg ctg aac tcg ggc    1056
Gly Leu Thr Gly Asp Asn Leu Val Gly Ile Gly Ala Leu Asn Ser Gly
            340              345              350 atc ggg aat cta ggt ttc ggg aac tcg ggt aac aac aac atc ggt ttc    1104
Ile Gly Asn Leu Gly Phe Gly Asn Ser Gly Asn Asn Asn Ile Gly Phe
            355              360              365 ttc aac tct ggc aac aac aac gtg ggc ttc ttc aat tcg ggc aac aac    1152
Phe Asn Ser Gly Asn Asn Asn Val Gly Phe Phe Asn Ser Gly Asn Asn
        370              375              380 aac ttc ggc ttt gga aac gcg ggc gac atc aac acg ggc ttc gga aac    1200
Asn Phe Gly Phe Gly Asn Ala Gly Asp Ile Asn Thr Gly Phe Gly Asn
385              390              395              400 gcc ggc gac acc aac acg ggc ttc gga aac gcc ggc ttc ttc aat atg    1248
Ala Gly Asp Thr Asn Thr Gly Phe Gly Asn Ala Gly Phe Phe Asn Met
                405              410              415 ggc atc ggg aac gcg ggc aac gaa gac atg ggc gtc ggg aac ggc ggt    1296
Gly Ile Gly Asn Ala Gly Asn Glu Asp Met Gly Val Gly Asn Gly Gly
            420              425              430 tcc ttt aac gtg ggc gtt ggc aat gcg ggc aac caa agt gtg ggc ttt    1344
Ser Phe Asn Val Gly Val Gly Asn Ala Gly Asn Gln Ser Val Gly Phe
            435              440              445 ggc aac gcg ggc acc cta aac gtg ggc ttc gca aac gcg ggc agt atc    1392
Gly Asn Ala Gly Thr Leu Asn Val Gly Phe Ala Asn Ala Gly Ser Ile
        450              455              460 aat acg gga ttc gcg aac tcg ggc agc atc aat acg ggc ggt ttc gac    1440
Asn Thr Gly Phe Ala Asn Ser Gly Ser Ile Asn Thr Gly Gly Phe Asp
465              470              475              480 tcg ggc gac cgg aac acc ggg ttt gga agc tcg gtc gac caa tcc gtt    1488
Ser Gly Asp Arg Asn Thr Gly Phe Gly Ser Ser Val Asp Gln Ser Val
                485              490              495 tcg agc tcg ggc ttc ggc aac acc ggc atg aat tcc tca ggc ttc ttt    1536
```

```
Ser Ser Ser Gly Phe Gly Asn Thr Gly Met Asn Ser Ser Gly Phe Phe
            500                 505                 510 aac acg ggc aat gtt tcg gct ggc tat ggg aac aac ggt gac gtt cag      1584
Asn Thr Gly Asn Val Ser Ala Gly Tyr Gly Asn Asn Gly Asp Val Gln
        515                 520                 525 tcg ggc atc aat aac acc aac tcc ggc ggc ttc aac gtc ggc ttc tat      1632
Ser Gly Ile Asn Asn Thr Asn Ser Gly Gly Phe Asn Val Gly Phe Tyr
    530                 535                 540 aac tcg ggt gcc ggc acc gtg ggc atc gca aac tct ggc ctg cag acc      1680
Asn Ser Gly Ala Gly Thr Val Gly Ile Ala Asn Ser Gly Leu Gln Thr
545                 550                 555                 560 aca ggc att gcg aac tcg ggc acc ctc aac acg ggt gtg gcg aac acg      1728
Thr Gly Ile Ala Asn Ser Gly Thr Leu Asn Thr Gly Val Ala Asn Thr
                565                 570                 575 ggt gac cac agc tcg ggg ggc ttc aat cag ggc agt gac cag tcg ggc      1776
Gly Asp His Ser Ser Gly Gly Phe Asn Gln Gly Ser Asp Gln Ser Gly
            580                 585                 590 ttc ttc ggt cag ccc taa                                              1794
Phe Phe Gly Gln Pro
        595

<210> SEQ ID NO 146
<211> LENGTH: 597
<212> TYPE: PRT
<213> ORGANISM: Artificial Sequence
<220> FEATURE:
<223> OTHER INFORMATION: Description of Artificial Sequence:mTTC#3-His

<400> SEQUENCE: 146

Met His His His His His Met Asn Tyr Ser Val Leu Pro Pro Glu
  1               5                  10                  15

Ile Asn Ser Leu Arg Met Phe Thr Gly Ala Gly Ser Ala Pro Met Leu
            20                  25                  30

Ala Ala Ser Val Ala Trp Asp Gly Leu Ala Ala Glu Leu Ala Val Ala
        35                  40                  45

Ala Ser Ser Phe Gly Ser Val Thr Ser Gly Leu Ala Gly Gln Ser Trp
    50                  55                  60

Gln Gly Ala Ala Ala Ala Met Ala Ala Ala Ala Pro Tyr Ala
65                  70                  75                  80

Gly Trp Leu Ala Ala Ala Ala Arg Ala Ala Gly Ala Ser Ala Gln
                85                  90                  95

Ala Lys Ala Val Ala Ser Ala Phe Glu Ala Ala Arg Ala Ala Thr Val
            100                 105                 110

His Pro Met Leu Val Ala Ala Asn Arg Asn Ala Phe Val Gln Leu Val
        115                 120                 125

Leu Ser Asn Leu Phe Gly Gln Asn Ala Pro Ala Ile Ala Ala Ala Glu
    130                 135                 140

Ala Met Tyr Glu Gln Met Trp Ala Ala Asp Val Ala Ala Met Val Gly
145                 150                 155                 160

Tyr His Gly Gly Ala Ser Ala Ala Ala Gln Leu Ser Ser Trp Ser
                165                 170                 175

Ile Gly Leu Gln Gln Ala Leu Pro Ala Ala Pro Ser Ala Leu Ala Ala
            180                 185                 190

Ala Ile Gly Leu Gly Asn Ile Gly Val Gly Asn Leu Gly Gly Gly Asn
        195                 200                 205

Thr Gly Asp Tyr Asn Leu Gly Ser Gly Asn Ser Gly Asn Ala Asn Val
    210                 215                 220
```

-continued

```
Gly Ser Gly Asn Ser Gly Asn Ala Asn Val Gly Ser Gly Asn Asp Gly
225                 230                 235                 240

Ala Thr Asn Leu Gly Ser Gly Asn Ile Gly Asn Thr Asn Leu Gly Ser
            245                 250                 255

Gly Asn Val Gly Asn Val Asn Leu Gly Ser Gly Asn Arg Gly Phe Gly
        260                 265                 270

Asn Leu Gly Asn Gly Asn Phe Gly Ser Gly Asn Leu Gly Ser Gly Asn
    275                 280                 285

Thr Gly Ser Thr Asn Phe Gly Gly Asn Leu Gly Ser Phe Asn Leu
290                 295                 300

Gly Ser Gly Asn Ile Gly Ser Ser Asn Ile Gly Phe Gly Asn Asn Gly
305                 310                 315                 320

Asp Asn Asn Leu Gly Leu Gly Asn Asn Gly Asn Asn Ile Gly Phe
                325                 330                 335

Gly Leu Thr Gly Asp Asn Leu Val Gly Ile Gly Ala Leu Asn Ser Gly
                340                 345                 350

Ile Gly Asn Leu Gly Phe Gly Asn Ser Gly Asn Asn Ile Gly Phe
            355                 360                 365

Phe Asn Ser Gly Asn Asn Val Gly Phe Phe Asn Ser Gly Asn Asn
    370                 375                 380

Asn Phe Gly Phe Gly Asn Ala Gly Asp Ile Asn Thr Gly Phe Gly Asn
385                 390                 395                 400

Ala Gly Asp Thr Asn Thr Gly Phe Gly Asn Ala Gly Phe Phe Asn Met
                405                 410                 415

Gly Ile Gly Asn Ala Gly Asn Glu Asp Met Gly Val Gly Asn Gly Gly
                420                 425                 430

Ser Phe Asn Val Gly Val Gly Asn Ala Gly Asn Gln Ser Val Gly Phe
            435                 440                 445

Gly Asn Ala Gly Thr Leu Asn Val Gly Phe Ala Asn Ala Gly Ser Ile
450                 455                 460

Asn Thr Gly Phe Ala Asn Ser Gly Ser Ile Asn Thr Gly Gly Phe Asp
465                 470                 475                 480

Ser Gly Asp Arg Asn Thr Gly Phe Gly Ser Ser Val Asp Gln Ser Val
                485                 490                 495

Ser Ser Ser Gly Phe Gly Asn Thr Gly Met Asn Ser Ser Gly Phe Phe
            500                 505                 510

Asn Thr Gly Asn Val Ser Ala Gly Tyr Gly Asn Asn Gly Asp Val Gln
            515                 520                 525

Ser Gly Ile Asn Asn Thr Asn Ser Gly Gly Phe Asn Val Gly Phe Tyr
530                 535                 540

Asn Ser Gly Ala Gly Thr Val Gly Ile Ala Asn Ser Gly Leu Gln Thr
545                 550                 555                 560

Thr Gly Ile Ala Asn Ser Gly Thr Leu Asn Thr Gly Val Ala Asn Thr
                565                 570                 575

Gly Asp His Ser Ser Gly Gly Phe Asn Gln Gly Ser Asp Gln Ser Gly
                580                 585                 590

Phe Phe Gly Gln Pro
            595
```

<210> SEQ ID NO 147
<211> LENGTH: 51
<212> TYPE: DNA
<213> ORGANISM: Artificial Sequence
<220> FEATURE:
<223> OTHER INFORMATION: Description of Artificial Sequence:mTTC#3

(MTB57) 5' PCR amplification primer

<400> SEQUENCE: 147
caattacata tgcatcacca tcaccatcac atgaattatt cggtgttgcc g        51

<210> SEQ ID NO 148
<211> LENGTH: 33
<212> TYPE: DNA
<213> ORGANISM: Artificial Sequence
<220> FEATURE:
<223> OTHER INFORMATION: Description of Artificial Sequence:mTTC#3
    (MTB57) 3' PCR amplification primer

<400> SEQUENCE: 148
caattaaagc ttttagggct gaccgaagaa gcc        33

<210> SEQ ID NO 149
<211> LENGTH: 421
<212> TYPE: DNA
<213> ORGANISM: Artificial Sequence
<220> FEATURE:
<223> OTHER INFORMATION: Description of Artificial Sequence:5' P1 lambda
    phage insert

<400> SEQUENCE: 149
ggatccgaat tctgcacgag ggkygacgac gamctttgca cacgagcgat ggcaaccctc        60
acgtccgcgc aaaccccgcg cgaggccgta gagcaattcg tcgagctgat ggtcgacgat       120
ccggtgcgcg ggcgcgtgct gttgctggcg ccggcggtag aaccggccct gacccggtcg       180
ggcgcggagt ggatgcccaa cttcatcgag ttgctgcaac gcaagttgtc ccgcatcgtt       240
gatccagttc tgcagaaact ggtcgccacc agcttgatcg gcgctcttac cggtctgttc       300
accgcatatc tgaacggacg gctgggagcc acccgcaagc aattcatcga ctactgcgtc       360
aacatgttgc tcagcaccgc cgcacctacg caccgcaccg cgagcgggga gaatccgaac       420
a       421

<210> SEQ ID NO 150
<211> LENGTH: 675
<212> TYPE: DNA
<213> ORGANISM: Artificial Sequence
<220> FEATURE:
<223> OTHER INFORMATION: Description of Artificial Sequence:P2 lambda
    phage insert

<400> SEQUENCE: 150
gatccgaatt cggcacgagt cgaggccacc gcttccatgg ccaggcccac atyttgatcg        60
gcgtggtggc cacgcccggt gtgaagtgct gttggccgtg atgtcggatt acagtctcgg       120
cgtgcccgac gagacaggcc ttggtgctga cgcggcgcgc gcgtgaagtg gcgctgacac       180
agcacattgg ggtatccgcg gagaccgatc gggccgtcgt ccccaagctg cgccaggcct       240
atgacagcct ggtgtgcggt cgccgccggc ttggcgccat ggagccgag atcgagaacg       300 cggtggccca tcagcgcgcg ctgggccttg acacccggc cggtgcccgt aacttctccc       360
ggtttctcgc caccaaagca cacgacatca cgcgagtgct ggcagcaacc gccgcggaat       420
cccaggccgg cgcggcgcgg ttgcgatccc tggcttcgtc ctatcaggct gtgggatttg       480
gccccaaacc ccaggagccg cctccggatc cagtgccatt tccgccctac cagccgaagg       540
tgtgggcggc gtgccgggcg cgtggccaag acccggacaa ggtcgtcagg acgttccatc       600
acgcgccgat gagcgcgaga ttccgctcgc ttactcgtgc cgaattsgga tctgatatcg       660

```
ccatggcctt gtcgt                                                    675
```

<210> SEQ ID NO 151
<211> LENGTH: 276
<212> TYPE: DNA
<213> ORGANISM: Artificial Sequence
<220> FEATURE:
<223> OTHER INFORMATION: Description of Artificial Sequence:3' P3 lambda
      phage insert

<400> SEQUENCE: 151

```
tgatcggtca atgcgcagta ctggtgacct agcgccgccg cggtggccat catctcctcg    60
atcggcgcgg acccgtccga ccagttcgaa tgcagatgca gatccccgcg caatgcggca   120
cggatcgccc ctccaccgag atcctcagcg tcagcgcgta attcagccag caggtccggc   180
tcgcggccag accaggcctg ggcgatgact ttcgcggttt tgggaccgat acccgccagc   240
gactgccagc tgttggcctg gccgtgccgc tgccgc                             276
```

<210> SEQ ID NO 152
<211> LENGTH: 456
<212> TYPE: DNA
<213> ORGANISM: Artificial Sequence
<220> FEATURE:
<223> OTHER INFORMATION: Description of Artificial Sequence:P4 lambda
      phage insert

<400> SEQUENCE: 152

```
ggatccgaat tctgcacgag gangaagtca tactgccgtc atacacnttt gtctytaccg    60
ccaacgcctt cgtgttgcgc ggtggtgtgc cagtctttgt cgatattcgg cccgacacgc   120
tcaacattga tgaaactcgc atcgtagacg ccatcacccc gcgaaccaag gccatcgtcc   180
ccgttcacta tgccggcgtg gcctgcgaga tggacgcgat catgaagatc gccacgcacc   240
acaacctggc ggtggtcgaa gacgcggccc aaggcgcgat ggcgtcgtat cgtgggcggg   300
cgctcggcag catcggcgac ctgggagcgc tctcatttca cgagaccaag aatgtgattt   360
ccggcgaagg cggcgccctg cttgtcaact cataagactt cctgctccgg gcagakattc   420
tcagggaaaa gggcaccaat mrcagccngc ttcctt                             456
```

<210> SEQ ID NO 153
<211> LENGTH: 341
<212> TYPE: DNA
<213> ORGANISM: Artificial Sequence
<220> FEATURE:
<223> OTHER INFORMATION: Description of Artificial Sequence:P6 lambda
      phage insert

<400> SEQUENCE: 153

```
gatatcggat cggaattcgg cacgaggtgc ccntgggggg acaactggtg cacaagaggt    60
tcgtccgtcc cggtcctntc gtatagggac aggtttcctc aagtttctga cgcgcgcggc   120
ggatagagac cgaactgtct cacgacgttc taaacccagc tcgcgtgccg ctttaatggg   180
cgaacagccc aacccttggg acctgctcca gccccaggat gcgacgagcc gacatcgagg   240
tgccaaacca tcccgtcgat atggactctt ggggaagatc agcctgttat ccccggggta   300
cctttatcc gttgagcgac accccttcca ctcgggggtg c                        341
```

<210> SEQ ID NO 154
<211> LENGTH: 396
<212> TYPE: DNA
<213> ORGANISM: Artificial Sequence
<220> FEATURE:

-continued

<223> OTHER INFORMATION: Description of Artificial Sequence:P7 lambda
      phage insert

<400> SEQUENCE: 154

| gatccgaatt cagagcggcg acccgtgctc caagctcctt cagcgtcgtc acgggctcat | 60 |
| cctatccggc agatcagcag gcggttcctc cgcaaagtgc ggctgcaacc taccgacttc | 120 |
| gtgcgcggcg aggaacgcgc ccctgggggg tatccgcccg cgtcagacaa cagtgcctcg | 180 |
| gtctgatcgg taataggcga ccgcctcgag gtccacatcc gccacctgct cgaaacgtca | 240 |
| ggtcttgggg tgcggggtgt accggacggt atgcgcccag atcgtgccgt ctcggaatac | 300 |
| gaaagtatcg actccgtcgt cgactcggct gaccgcggaa ttcgcggtcc actccaggaa | 360 |
| cagtatgtcg ccctcgaaga tttgggtctt taagtc | 396 |

<210> SEQ ID NO 155
<211> LENGTH: 172
<212> TYPE: DNA
<213> ORGANISM: Artificial Sequence
<220> FEATURE:
<223> OTHER INFORMATION: Description of Artificial Sequence:P8 lambda
      phage insert

<400> SEQUENCE: 155

| ggatccgaat tcggcacgag gagtatcagc agaggtcgga gaaggtgctg accgaataca | 60 |
| acaacaaggc agccctggaa ccggtaaacc cgccgaagcc tcccccgcc atcaagatcg | 120 |
| acccgccccc gcctccgcaa gagcagggat tgatccctgg cttcctgatg cc | 172 |

<210> SEQ ID NO 156
<211> LENGTH: 92
<212> TYPE: DNA
<213> ORGANISM: Artificial Sequence
<220> FEATURE:
<223> OTHER INFORMATION: Description of Artificial Sequence:P9 lambda
      phage insert

<400> SEQUENCE: 156

| ggatccgaat tcggcacgag ccagaacctc gcckgccccg ggcggcagng acaccaactg | 60 |
| gscaccacgc cgcggatcgg cmgagcagcg cc | 92 |

<210> SEQ ID NO 157
<211> LENGTH: 609
<212> TYPE: DNA
<213> ORGANISM: Artificial Sequence
<220> FEATURE:
<223> OTHER INFORMATION: Description of Artificial Sequence:5' P10
      lambda phage insert

<400> SEQUENCE: 157

| gatccgaatt cggcacgaga agaatntgac ccnncnccng tggctgatgc gagagcttnc | 60 |
| ttntttcttc cccccantgg ttggacgggg tcgtcacagc gggcattcta agtcccgcgg | 120 |
| gccacaaaag gcagtgccgc ggaacttctt ggcccaaacg ggcacccggc tacgtgcgca | 180 |
| ccgcgaccgt cgacaactgg tcggcgagcc ggtccgggga atccaccatc gagaacgtcc | 240 |
| gtgctccctc gattacctcg aaacgggcgc gcgggatggt cgcggcgagc cgttgaccgt | 300 |
| tctcgagtgc gaagaacacg tcatccgccg accacgcgat gagcgccggc ttgtcgaatt | 360 |
| caggcagccg ggcggcgact gcggtggtga cttcggtgcg cagcgatagc gagagctgac | 420 |
| gcaggtcttc ggcgatggcc gggttggata gcgccgacg aacccaggcc cgggtgagat | 480 |
| ggtcgatgtt gtggtgcgac aaaccggcat acgcgcggtt tacgcgcggc cggtgcccgc | 540 |

-continued

```
atcacctgga tcgcggcccg aacagggtg gccgatttcg cggncaggat cacctgnttt    600
gaggatcgg                                                           609
```

<210> SEQ ID NO 158
<211> LENGTH: 301
<212> TYPE: DNA
<213> ORGANISM: Artificial Sequence
<220> FEATURE:
<223> OTHER INFORMATION: Description of Artificial Sequence:5' P11
      lambda phage insert

<400> SEQUENCE: 158

```
ggatccgaat tcggcacgag tgcggtgcct atctgcgttg ccagtacct cgcggacctg    60 gcgagtgcgg acgcgcaggc tatcgaagtg ggcctaaaga cggcggacgt ggcgcccgtt   120
gccgtacgac ctgcagcggc gccgccgttg cgtgagtctg ccgcggtgcg accggaggcc   180
aggctggtgt cggcggtggc gccagctccc gcgggcacgt cggcgtcggt gctggcttcg   240
gatcggggtg ccggcgtgtt gggtttgcc gggaccgctg gcaaggantc cnttgggcgt    300
c                                                                   301
```

<210> SEQ ID NO 159
<211> LENGTH: 261
<212> TYPE: DNA
<213> ORGANISM: Artificial Sequence
<220> FEATURE:
<223> OTHER INFORMATION: Description of Artificial Sequence:3' P12
      lambda phage insert

<400> SEQUENCE: 159

```
ggctgctgcg cgcactcgcg ggtctgctgg acgagtggac gccggtgatc gccggcgccg   60
aactgggcga gcaccctac acgccgatca cgccggagtc gatccggcgg gccgcgcagc   120
tcggcgacga cctaccggtg gcgtggaagc accgcagcga gcgctacacc gagaagctgg   180 ccaccccga caccagcgtc gccgacctgg tcggcgacgt cgacccgatc aaggttgccg   240
agggccgcag cctcggggat c                                             261
```

<210> SEQ ID NO 160
<211> LENGTH: 1404
<212> TYPE: DNA
<213> ORGANISM: Mycobacterium tuberculosis
<220> FEATURE:
<223> OTHER INFORMATION: MO-1 (unknown protein from cosmid MTCI237)
<221> NAME/KEY: CDS
<222> LOCATION: (43)..(1404)
<223> OTHER INFORMATION: MO-1

<400> SEQUENCE: 160

```
tgagattggc agaccggtga gcaccggata cagccacgca aa gtt cgt cac cac     54
                                              Val Arg His His
                                                1 gag ggc cac gta gca gca gac gac gat cag ccc cag tgt gcg tcg ttc   102
Glu Gly His Val Ala Ala Asp Asp Asp Gln Pro Gln Cys Ala Ser Phe
  5                  10                  15                  20 gga gcc ctg acc ggg gtg ata gag gat atc gcc gag aac cag cga aat   150
Gly Ala Leu Thr Gly Val Ile Glu Asp Ile Ala Glu Asn Gln Arg Asn
             25                  30                  35 gcc cat cac cag aaa tgg cgc cat ggt cgc tgc gta gaa gaa gta cat   198
Ala His His Gln Lys Trp Arg His Gly Arg Cys Val Glu Glu Val His
         40                  45                  50 ctg ccg gtc gat gtc ggc gaa cca cgg cag cca acc ggc gca gta gcc   246
```

```
                                                                -continued

Leu Pro Val Asp Val Gly Glu Pro Arg Gln Pro Thr Gly Ala Val Ala
         55                  60                  65 gac cag gac cac cgc ata acg cca gtc ccg gcg cac aaa cat acg cca    294
Asp Gln Asp His Arg Ile Thr Pro Val Pro Ala His Lys His Thr Pro
         70                  75                  80 ccc cgc gta tgc cag gac tgg cac cgc cag cca cat cgc ggg cgt        342
Pro Arg Val Cys Gln Asp Trp His Arg Gln Pro Pro His Arg Gly Arg
 85                  90                  95                 100 gcc gac cag cat ctc ggc ctt gac gca cga ctg tgc gcc gca gcc tgc    390
Ala Asp Gln His Leu Gly Leu Asp Ala Arg Leu Cys Ala Ala Ala Cys
                    105                 110                 115 aac gtc ttg ctg gtc gat ggc gta cag cac cgg ccg caa cga cat ggg    438
Asn Val Leu Leu Val Asp Gly Val Gln His Arg Pro Gln Arg His Gly
                120                 125                 130 cca ggt cca cgg ttt gga ttc cca agg gtg gta gtt gcc tgc gga att    486
Pro Gly Pro Arg Phe Gly Phe Pro Arg Val Val Val Ala Cys Gly Ile
            135                 140                 145 cgt cag gcc cgc gtg gaa gtg gaa cgc ttt ggc ggt gta gtg cca gag    534
Arg Gln Ala Arg Val Glu Val Glu Arg Phe Gly Gly Val Val Pro Glu
        150                 155                 160 cga gcg cac ggc gtc ggg cag cgg aac aac cga gtt gcg acc gac cgc    582
Arg Ala His Gly Val Gly Gln Arg Asn Asn Arg Val Ala Thr Asp Arg
165                 170                 175                 180 ttg acc gac cgc atg ccg atc gat cgc ggt ctc gga cgc gaa cca cgg    630
Leu Thr Asp Arg Met Pro Ile Asp Arg Gly Leu Gly Arg Glu Pro Arg
                    185                 190                 195 agc gta ggt ggc cag ata gac cgc gaa cgg gat caa ccc cag cgc ata    678
Ser Val Gly Gly Gln Ile Asp Arg Glu Arg Asp Gln Pro Gln Arg Ile
                200                 205                 210 ccc gct ggg aag cac gtc acg ccg cac tgt ccc cag cca cgg tct ttg    726
Pro Ala Gly Lys His Val Thr Pro His Cys Pro Gln Pro Arg Ser Leu
            215                 220                 225 cac ttg gta ctg acg tcg cgc cgc cac gtc gaa cgc cag cgc cat cgc    774
His Leu Val Leu Thr Ser Arg Arg His Val Glu Arg Gln Arg His Arg
        230                 235                 240 gcc gaa gaa cag cac gaa gta cac gcc gga cca ctt ggt ggc gca agc    822
Ala Glu Glu Gln His Glu Val His Ala Gly Pro Leu Gly Gly Ala Ser
245                 250                 255                 260 caa tcc cag cag cac ccc ggc gcc gaa ccg cca cca gcg cac acc cac    870
Gln Ser Gln Gln His Pro Gly Ala Glu Pro Pro Pro Ala His Thr His
                    265                 270                 275 ccg cgg tcc cca cac ggt ggc ggc gct gcg gcc ggc cag cag agc gat    918
Pro Arg Ser Pro His Gly Gly Gly Ala Ala Ala Gly Gln Gln Ser Asp
                280                 285                 290 gtg cat ccg ttc gcg aac ctg atc gcg gtc gac gat gag cgc gcc gaa    966
Val His Pro Phe Ala Asn Leu Ile Ala Val Asp Asp Glu Arg Ala Glu
            295                 300                 305 cgc cgc gac gac gaa gaa cgt cag gaa gcc gtc cag cag cgc ggt ccg   1014
Arg Arg Asp Asp Glu Glu Arg Gln Glu Ala Val Gln Gln Arg Gly Pro
        310                 315                 320 cgc ggt gac gaa gct gac ccc gtc gca gat cag cag cac ccc ggc gat   1062
Arg Gly Asp Glu Ala Asp Pro Val Ala Asp Gln Gln His Pro Gly Asp
325                 330                 335                 340 ggc gcc gac caa tgt cga ccg gct gat ccg ccg cac gat ccg cac cac   1110
Gly Ala Asp Gln Cys Arg Pro Ala Asp Pro Pro His Asp Pro His His
                    345                 350                 355 cag cgc cac cag gac cac acc cag cag ggc gcc ggt gaa ccg cca gcc   1158
Gln Arg His Gln Asp His Thr Gln Gln Gly Ala Gly Glu Pro Pro Ala
                360                 365                 370
```

```
gaa tcc gtt gta acc gaa gat ggc ctc ccc gat cgc gat cag ctg ctt    1206
Glu Ser Val Val Thr Glu Asp Gly Leu Pro Asp Arg Asp Gln Leu Leu
        375                 380                 385 acc gac cgg cgg gtg aac cac cag gcc gta ccc ggg gtt gtc ttc cac    1254
Thr Asp Arg Arg Val Asn His Gln Ala Val Pro Gly Val Val Phe His
    390                 395                 400 ccc atg gtt gtt cag cac ctg cca ggc ctg ggg tgc gta atg ctt ctc    1302
Pro Met Val Val Gln His Leu Pro Gly Leu Gly Cys Val Met Leu Leu
405                 410                 415                 420 gtc gaa gat ggg ggt gcc ggc atc ggt cag cga gcc cag gtt cag gaa    1350
Val Glu Asp Gly Gly Ala Gly Ile Gly Gln Arg Ala Gln Val Gln Glu
                425                 430                 435 ccg ggt cac cgt ggc cag cag cgt gat cag gcc ggt cac gat cca gcc    1398
Pro Gly His Arg Gly Gln Gln Arg Asp Gln Ala Gly His Asp Pro Ala
            440                 445                 450 gcg taa                                                             1404
Ala
```

<210> SEQ ID NO 161
<211> LENGTH: 453
<212> TYPE: PRT
<213> ORGANISM: Mycobacterium tuberculosis
<223> OTHER INFORMATION: MO-1 (unknown protein from cosmid MTCI237)

<400> SEQUENCE: 161

```
Val Arg His His Glu Gly His Val Ala Ala Asp Asp Gln Pro Gln
 1               5                  10                  15

Cys Ala Ser Phe Gly Ala Leu Thr Gly Val Ile Glu Asp Ile Ala Glu
                20                  25                  30

Asn Gln Arg Asn Ala His His Gln Lys Trp Arg His Gly Arg Cys Val
            35                  40                  45

Glu Glu Val His Leu Pro Val Asp Val Gly Glu Pro Arg Gln Pro Thr
        50                  55                  60

Gly Ala Val Ala Asp Gln Asp His Arg Ile Thr Pro Val Pro Ala His
65                  70                  75                  80

Lys His Thr Pro Pro Arg Val Cys Gln Asp Trp His Arg Gln Pro Pro
                85                  90                  95

His Arg Gly Arg Ala Asp Gln His Leu Gly Leu Asp Ala Arg Leu Cys
            100                 105                 110

Ala Ala Ala Cys Asn Val Leu Leu Val Asp Gly Val Gln His Arg Pro
        115                 120                 125

Gln Arg His Gly Pro Gly Pro Arg Phe Gly Phe Pro Arg Val Val Val
    130                 135                 140

Ala Cys Gly Ile Arg Gln Ala Arg Val Glu Val Glu Arg Phe Gly Gly
145                 150                 155                 160

Val Val Pro Glu Arg Ala His Gly Val Gly Gln Arg Asn Asn Arg Val
                165                 170                 175

Ala Thr Asp Arg Leu Thr Asp Arg Met Pro Ile Asp Arg Gly Leu Gly
            180                 185                 190

Arg Glu Pro Arg Ser Val Gly Gly Gln Ile Asp Arg Glu Arg Asp Gln
        195                 200                 205

Pro Gln Arg Ile Pro Ala Gly Lys His Val Thr Pro His Cys Pro Gln
    210                 215                 220

Pro Arg Ser Leu His Leu Val Leu Thr Ser Arg Arg His Val Glu Arg
225                 230                 235                 240

Gln Arg His Arg Ala Glu Glu Gln His Glu Val His Ala Gly Pro Leu
                245                 250                 255
```

```
Gly Gly Ala Ser Gln Ser Gln Gln His Pro Gly Ala Glu Pro Pro Pro
            260                 265                 270

Ala His Thr His Pro Arg Ser Pro His Gly Gly Gly Ala Ala Ala Gly
            275                 280                 285

Gln Gln Ser Asp Val His Pro Phe Ala Asn Leu Ile Ala Val Asp Asp
            290                 295                 300

Glu Arg Ala Glu Arg Arg Asp Asp Glu Arg Gln Glu Ala Val Gln
305                 310                 315                 320

Gln Arg Gly Pro Arg Gly Asp Glu Ala Asp Pro Val Ala Asp Gln Gln
                325                 330                 335

His Pro Gly Asp Gly Ala Asp Gln Cys Arg Pro Ala Asp Pro Pro His
            340                 345                 350

Asp Pro His His Gln Arg His Gln Asp His Thr Gln Gln Gly Ala Gly
            355                 360                 365

Glu Pro Pro Ala Glu Ser Val Val Thr Glu Asp Gly Leu Pro Asp Arg
            370                 375                 380

Asp Gln Leu Leu Thr Asp Arg Arg Val Asn His Gln Ala Val Pro Gly
385                 390                 395                 400

Val Val Phe His Pro Met Val Val Gln His Leu Pro Gly Leu Gly Cys
                405                 410                 415

Val Met Leu Leu Val Glu Asp Gly Gly Ala Gly Ile Gly Gln Arg Ala
            420                 425                 430

Gln Val Gln Glu Pro Gly His Arg Gly Gln Gln Arg Asp Gln Ala Gly
            435                 440                 445

His Asp Pro Ala Ala
            450

<210> SEQ ID NO 162
<211> LENGTH: 1863
<212> TYPE: DNA
<213> ORGANISM: Mycobacterium tuberculosis
<220> FEATURE:
<223> OTHER INFORMATION: MO-2 (aspartokinase)
<221> NAME/KEY: CDS
<222> LOCATION: (1)..(1266)
<223> OTHER INFORMATION: MO-2

<400> SEQUENCE: 162 gtg gcg ctc gtc gtg cag aag tac ggc gga tcc tcg gtg gcc gac gcc    48
Val Ala Leu Val Val Gln Lys Tyr Gly Gly Ser Ser Val Ala Asp Ala
  1               5                  10                  15 gaa cgg att cgc cgc gtc gcc gaa cgc atc gtc gcc acc aag aag caa    96
Glu Arg Ile Arg Arg Val Ala Glu Arg Ile Val Ala Thr Lys Lys Gln
             20                  25                  30 ggc aat gac gtc gtc gtc gtc tct gcc atg ggg gat acc acc gac       144
Gly Asn Asp Val Val Val Val Ser Ala Met Gly Asp Thr Thr Asp
         35                  40                  45 gac ctg ctg gat ctg gct cag cag gtg tgc ccg gcg ccg ccg cct cgg    192
Asp Leu Leu Asp Leu Ala Gln Gln Val Cys Pro Ala Pro Pro Pro Arg
     50                  55                  60 gag ctg gac atg ctg ctt acc gcc ggt gaa cgc atc tcg aat gcg ttg    240
Glu Leu Asp Met Leu Leu Thr Ala Gly Glu Arg Ile Ser Asn Ala Leu
 65                  70                  75                  80 gtg gcc atg gcc atc gag tcg ctc ggc gcg cat gcc cgg tcg ttc acc    288
Val Ala Met Ala Ile Glu Ser Leu Gly Ala His Ala Arg Ser Phe Thr
                 85                  90                  95 ggt tcg cag gcc ggg gtg atc acc acc ggc acc cac ggc aac gcc aag    336
Gly Ser Gln Ala Gly Val Ile Thr Thr Gly Thr His Gly Asn Ala Lys
```

-continued

```
                100                    105                    110
atc atc gac gtc acg ccg ggg cgg ctg caa acc gcc ctt gag gag ggg    384
Ile Ile Asp Val Thr Pro Gly Arg Leu Gln Thr Ala Leu Glu Glu Gly
            115                    120                    125 cgg gtc gtt ttg gtg gcc gga ttc caa ggg gtc agc cag gac acc aag    432
Arg Val Val Leu Val Ala Gly Phe Gln Gly Val Ser Gln Asp Thr Lys
    130                    135                    140 gat gtc acg acg ttg ggc cgc ggc ggc tcg gac acc acc gcc gtc gcc    480
Asp Val Thr Thr Leu Gly Arg Gly Gly Ser Asp Thr Thr Ala Val Ala
145                    150                    155                    160 atg gcc gcc gcg ctg ggt gcc gat gtc tgt gag atc tac acc gac gtg    528
Met Ala Ala Ala Leu Gly Ala Asp Val Cys Glu Ile Tyr Thr Asp Val
                165                    170                    175 gac ggc atc ttc agc gcc gac ccg cgc atc gtg cgc aac gcc cga aag    576
Asp Gly Ile Phe Ser Ala Asp Pro Arg Ile Val Arg Asn Ala Arg Lys
            180                    185                    190 ctc gac acc gtg acc ttc gag gaa atg ctc gag atg gcg gcc tgc ggc    624
Leu Asp Thr Val Thr Phe Glu Glu Met Leu Glu Met Ala Ala Cys Gly
    195                    200                    205 gcc aag gtg ctg atg ctg cgc tgc gtg gaa tac gct cgc cgc cat aat    672
Ala Lys Val Leu Met Leu Arg Cys Val Glu Tyr Ala Arg Arg His Asn
210                    215                    220 att ccg gtg cac gtc cgg tcg tcg tac tcg gac aga ccg ggc acc gtc    720
Ile Pro Val His Val Arg Ser Ser Tyr Ser Asp Arg Pro Gly Thr Val
225                    230                    235                    240 gtt gtc gga tcg atc aag gac gta ccc atg gaa gac ccc atc ctg acc    768
Val Val Gly Ser Ile Lys Asp Val Pro Met Glu Asp Pro Ile Leu Thr
                245                    250                    255 gga gtc gcg cac gac cgc agc gag gcc aag gtg acc atc gtc ggg ctg    816
Gly Val Ala His Asp Arg Ser Glu Ala Lys Val Thr Ile Val Gly Leu
            260                    265                    270 ccc gac atc ccc ggg tat gcg gcc aag gtg ttt agg gcg gtg gcc gac    864
Pro Asp Ile Pro Gly Tyr Ala Ala Lys Val Phe Arg Ala Val Ala Asp
    275                    280                    285 gcc gac gtc aac atc gac atg gtg ctg cag aac gtc tcc aag gtc gag    912
Ala Asp Val Asn Ile Asp Met Val Leu Gln Asn Val Ser Lys Val Glu
290                    295                    300 gac ggc aag acc gac atc acc ttc acc tgc tcc cgc gac gtc ggg ccc    960
Asp Gly Lys Thr Asp Ile Thr Phe Thr Cys Ser Arg Asp Val Gly Pro
305                    310                    315                    320 gcc gcc gtg gaa aaa ctg gac tcg ctc aga aac gag atc ggc ttc tca   1008
Ala Ala Val Glu Lys Leu Asp Ser Leu Arg Asn Glu Ile Gly Phe Ser
                325                    330                    335 cag ctg ctg tac gac gac cac atc ggc aag gta tcg ctg atc ggt gcc   1056
Gln Leu Leu Tyr Asp Asp His Ile Gly Lys Val Ser Leu Ile Gly Ala
            340                    345                    350 ggc atg cgc agc cac ccc ggg gtc acc gcg acg ttc tgt gag gcg ctg   1104
Gly Met Arg Ser His Pro Gly Val Thr Ala Thr Phe Cys Glu Ala Leu
    355                    360                    365 gcg gcg gtg ggg gtc aac atc gag ctg atc tcc acc tcg gag atc agg   1152
Ala Ala Val Gly Val Asn Ile Glu Leu Ile Ser Thr Ser Glu Ile Arg
370                    375                    380 atc tcg gtg ttg tgc cgc gac acc gaa ctg gac aag gcc gtg gtc gcg   1200
Ile Ser Val Leu Cys Arg Asp Thr Glu Leu Asp Lys Ala Val Val Ala
385                    390                    395                    400 ctg cat gaa gcg ttc ggg ctc ggc ggc gac gag gag gcc acg gtg tac   1248
Leu His Glu Ala Phe Gly Leu Gly Gly Asp Glu Glu Ala Thr Val Tyr
                405                    410                    415 gcg ggg acg gga cgg tag atgggcctgt caataggggat cgtgggggcc          1296
Ala Gly Thr Gly Arg
```

-continued

```
Ala Gly Thr Gly Arg
            420
```

| accggtcagg tgggtcaggt catgcgcacg ttgctcgacg agcgggattt cccggcgagc | 1356 |
|---|---|
| gcggtgcggt tcttcgcgtc ggcccgatcg cagggccgca agctggcctt ccgcggccag | 1416 |
| gagatcgaag tggaagacgc cgagacggcc gacccgagcg ggctggatat cgcgttgttc | 1476 |
| tccgccggct cggccatgtc gaaggtgcag gcgccccgct ttgcggcggc cggagtcacg | 1536 |
| gtgatcgaca actcgtcggc gtggcgtaag gaccccgacg tgccgttggt ggtgtccgag | 1596 |
| gtgaactttg aacgcgacgc gcaccgccgg cccaaggctc gtgccgctcg tgccgaattc | 1656 |
| ggcacgagcc gacgtggtcg gcaacgtcct ggatcgcggg cagctggttg ttgaggatga | 1716 |
| atccgtccac caggtggtag gagccgaacg aagattccac cgtcgtcgtc aacgtggccg | 1776 |
| cattgccgta cgaatcgacg acgctgaggt ggctggtgcc atgctcaggc actggcgggg | 1836 |
| cgacggccgt cggtgcgccg aagtccc | 1863 |

```
<210> SEQ ID NO 163
<211> LENGTH: 421
<212> TYPE: PRT
<213> ORGANISM: Mycobacterium tuberculosis
<223> OTHER INFORMATION: MO-2 (aspartokinase)

<400> SEQUENCE: 163

Val Ala Leu Val Val Gln Lys Tyr Gly Gly Ser Ser Val Ala Asp Ala
 1               5                  10                  15

Glu Arg Ile Arg Arg Val Ala Glu Arg Ile Val Ala Thr Lys Lys Gln
            20                  25                  30

Gly Asn Asp Val Val Val Val Ser Ala Met Gly Asp Thr Thr Asp
        35                  40                  45

Asp Leu Leu Asp Leu Ala Gln Gln Val Cys Pro Ala Pro Pro Arg
    50                  55                  60

Glu Leu Asp Met Leu Leu Thr Ala Gly Glu Arg Ile Ser Asn Ala Leu
65                  70                  75                  80

Val Ala Met Ala Ile Glu Ser Leu Gly Ala His Ala Arg Ser Phe Thr
                85                  90                  95

Gly Ser Gln Ala Gly Val Ile Thr Thr Gly Thr His Gly Asn Ala Lys
            100                 105                 110

Ile Ile Asp Val Thr Pro Gly Arg Leu Gln Thr Ala Leu Glu Glu Gly
        115                 120                 125

Arg Val Val Leu Val Ala Gly Phe Gln Gly Val Ser Gln Asp Thr Lys
    130                 135                 140

Asp Val Thr Thr Leu Gly Arg Gly Gly Ser Asp Thr Thr Ala Val Ala
145                 150                 155                 160

Met Ala Ala Ala Leu Gly Ala Asp Val Cys Glu Ile Tyr Thr Asp Val
                165                 170                 175

Asp Gly Ile Phe Ser Ala Asp Pro Arg Ile Val Arg Asn Ala Arg Lys
            180                 185                 190

Leu Asp Thr Val Thr Phe Glu Glu Met Leu Glu Met Ala Ala Cys Gly
        195                 200                 205

Ala Lys Val Leu Met Leu Arg Cys Val Glu Tyr Ala Arg Arg His Asn
    210                 215                 220

Ile Pro Val His Val Arg Ser Ser Tyr Ser Asp Arg Pro Gly Thr Val
225                 230                 235                 240

Val Val Gly Ser Ile Lys Asp Val Pro Met Glu Asp Pro Ile Leu Thr
                245                 250                 255
```

```
Gly Val Ala His Asp Arg Ser Glu Ala Lys Val Thr Ile Val Gly Leu
            260                 265                 270

Pro Asp Ile Pro Gly Tyr Ala Ala Lys Val Phe Arg Ala Val Ala Asp
        275                 280                 285

Ala Asp Val Asn Ile Asp Met Val Leu Gln Asn Val Ser Lys Val Glu
    290                 295                 300

Asp Gly Lys Thr Asp Ile Thr Phe Thr Cys Ser Arg Asp Val Gly Pro
305                 310                 315                 320

Ala Ala Val Glu Lys Leu Asp Ser Leu Arg Asn Glu Ile Gly Phe Ser
                325                 330                 335

Gln Leu Leu Tyr Asp Asp His Ile Gly Lys Val Ser Leu Ile Gly Ala
            340                 345                 350

Gly Met Arg Ser His Pro Gly Val Thr Ala Thr Phe Cys Glu Ala Leu
        355                 360                 365

Ala Ala Val Gly Val Asn Ile Glu Leu Ile Ser Thr Ser Glu Ile Arg
    370                 375                 380

Ile Ser Val Leu Cys Arg Asp Thr Glu Leu Asp Lys Ala Val Val Ala
385                 390                 395                 400

Leu His Glu Ala Phe Gly Leu Gly Gly Asp Glu Ala Thr Val Tyr
                405                 410                 415

Ala Gly Thr Gly Arg
            420

<210> SEQ ID NO 164
<211> LENGTH: 1379
<212> TYPE: DNA
<213> ORGANISM: Mycobacterium tuberculosis
<220> FEATURE:
<223> OTHER INFORMATION: full-length TbH4/XP-1 (MTB48) open reading
      frame

<400> SEQUENCE: 164
atgacgcagt cgcagaccgt gacggtggat cagcaagaga ttttgaacag ggccaacgag      60
gtggaggccc cgatggcgga cccaccgact gatgtcccca tcacaccgtg cgaactcacg     120
gcggctaaaa acgccgccca acagctggta ttgtccgccg acaacatgcg ggaatacctg     180
gcggccggtg ccaaagagcg gcagcgtctg cgacctcgc tgcgcaacgc ggccaaggcg     240 tatgcgagg ttgatgagga ggctgcgacc gcgctggaca acgacggcga aggaacgtgc     300
aggcagaatc ggccggggcc gtcggagggg acagttcggc cgaactaacc gatacgccga     360
gggtggccac ggccggtgaa cccaacttca tggatctcaa agaagcggca aggaagctcg     420
aaacgggcga ccaaggcgca tcgctcgcgc actttgcgga tgggtggaac actttcaacc     480
tgacgctgca aggcgacgtc aagcggttcc ggggggtttga caactgggaa ggcgatgcgg     540
ctaccgcttg cgaggcttcg ctcgatcaac aacggcaatg gatactccac atggccaaat     600
tgagcgctgc gatggccaag caggctcaat atgtcgcgca gctgcacgtg tgggctaggc     660
gggaacatcc gacttatgaa gacatagtcg ggctcgaacg gctttacgcg gaaaacccctt     720 cggcccgcga ccaaattctc ccggtgtacg cggagtatca gcagaggtcg gagaaggtgc     780
tgaccgaata caacaacaag gcagccctgg aaccggtaaa cccgccgaag cctcccccccg     840 ccatcaagat cgacccgccc ccgcctccgc aagagcaggg attgatccct ggcttcctga     900
tgccgccgtc tgacggctcc ggtgtgactc ccggtaccgg gatgccagcc gcaccgatgg     960
ttccgcctac cggatcgccg ggtggtggcc tcccggctga cacggcggcg cagctgacgt    1020
```

```
cggctgggcg ggaagccgca gcgctgtcgg gcgacgtggc ggtcaaagcg gcatcgctcg    1080
gtggcggtgg aggcggcggg gtgccgtcgg cgccgttggg atccgcgatc ggggcgccg     1140 aatcggtgcg gcccgctggc gctggtgaca ttgccggctt aggccaggga agggccggcg    1200
gcggcgccgc gctgggcggc ggtggcatgg gaatgccgat gggtgccgcg catcagggac    1260 aaggggcgc caagtccaag ggttctcagc aggaagacga ggcgctctac accgaggatc     1320
gggcatggac cgaggccgtc attggtaacc gtcggcgcca ggacagtaag gagtcgaag     1379
```